United States Patent
Van De Winkel et al.

(10) Patent No.: US 10,752,695 B2
(45) Date of Patent: Aug. 25, 2020

(54) STABLE IGG4 ANTIBODIES

(71) Applicant: GENMAB A/S, Copenhagen V (DK)

(72) Inventors: Jan Van De Winkel, Zeist (NL); Tom Vink, Alphen aan den Rijn (NL); Janine Schuurman, Diemen (NL); Paul Parren, Odijk (NL); Rob Aalberse, Duivendrecht (NL); Marijn Van Der Neut Kolfschoten, Amsterdam (NL)

(73) Assignee: Genmab A/S, Copenhagen V (DK)

( * ) Notice: Subject to any disclaimer, the term of this patent is extended or adjusted under 35 U.S.C. 154(b) by 365 days.

(21) Appl. No.: 15/197,496

(22) Filed: Jun. 29, 2016

(65) Prior Publication Data

US 2017/0029521 A1 Feb. 2, 2017

Related U.S. Application Data

(60) Continuation of application No. 13/912,581, filed on Jun. 7, 2013, now abandoned, which is a division of application No. 12/602,439, filed as application No. PCT/DK2008/050129 on May 30, 2008, now abandoned.

(30) Foreign Application Priority Data

| May 31, 2007 | (DK) | 2007 00792 |
| May 31, 2007 | (DK) | 2007 00793 |
| Jul. 6, 2007 | (DK) | 2007 01002 |

(51) Int. Cl.
| C07K 16/00 | (2006.01) |
| C12P 21/08 | (2006.01) |
| C07K 16/28 | (2006.01) |
| A61K 51/10 | (2006.01) |
| A61K 47/68 | (2017.01) |
| C07K 16/16 | (2006.01) |
| C07K 16/18 | (2006.01) |
| C07K 1/00 | (2006.01) |
| A61K 39/00 | (2006.01) |

(52) U.S. Cl.
CPC ...... *C07K 16/2887* (2013.01); *A61K 47/6803* (2017.08); *A61K 47/6813* (2017.08); *A61K 47/6835* (2017.08); *A61K 47/6839* (2017.08); *A61K 47/6845* (2017.08); *A61K 47/6849* (2017.08); *A61K 51/10* (2013.01); *A61K 51/103* (2013.01); *A61K 51/1006* (2013.01); *A61K 51/1021* (2013.01); *A61K 51/1027* (2013.01); *A61K 51/1039* (2013.01); *C07K 16/00* (2013.01); *C07K 16/16* (2013.01); *C07K 16/18* (2013.01); *C07K 16/28* (2013.01); *C07K 16/2863* (2013.01); *A61K 2039/505* (2013.01); *C07K 2317/21* (2013.01); *C07K 2317/24* (2013.01); *C07K 2317/31* (2013.01); *C07K 2317/526* (2013.01); *C07K 2317/53* (2013.01); *C07K 2317/55* (2013.01); *C07K 2317/94* (2013.01)

(58) Field of Classification Search
None
See application file for complete search history.

(56) References Cited

U.S. PATENT DOCUMENTS

| 5,648,260 A | 7/1997 | Winter et al. |
| 6,737,056 B1 | 5/2004 | Presta |
| 9,150,663 B2 * | 10/2015 | Labrijn .............. C07K 16/1063 |
| 2006/0074225 A1 * | 4/2006 | Chamberlain ......... C07K 16/00 530/387.1 |
| 2007/0105199 A1 | 5/2007 | Yan |
| 2008/0063635 A1 | 3/2008 | Takahashi et al. |

FOREIGN PATENT DOCUMENTS

| EP | 1 139 464 A1 | 2/2004 |
| EP | 1 810 979 A1 | 7/2007 |
| EP | 1 870 459 A1 | 12/2007 |
| WO | WO 88/07089 A1 | 9/1988 |
| WO | WO 99/55369 A1 | 11/1999 |
| WO | WO 02/086186 A1 | 11/2002 |
| WO | WO 03/074679 A2 | 9/2003 |
| WO | WO 2005/063816 A2 | 7/2005 |
| WO | WO 2006/033386 A1 | 3/2006 |
| WO | WO 2006/106905 A1 | 10/2006 |

OTHER PUBLICATIONS

NCBI Blast® Protein Sequence Alignment 1; Nov. 30, 2012; SEQ ID No. 40 of U.S. Appl. No. 12/602,439, to prior art IgG4 constant in SEQ ID No. 44 of U.S. Patent Publication No. 2008/0063635; 2 pages.
NCB1 Blast® Protein Sequence Alignment 2; Nov. 30, 2012; SEQ ID No. 40 of U.S. Appl. No. 12/602,439. to SEQ ID No. 21 of U.S. Appl. No. 12/602,404; pp. 1-2.
Aalberse, R.C. et al.; "The Apparent Monovalency of Human IgG4 is Due to Bispecificity" *Int Arch Allergy Immunology*; 1999; vol. 118; pp. 187-189.
Aalberse, R.C. et al.; "IgG4 breaking the rules", *Immunology*; 2002; vol. 105, No. 1; pp. 9-19.
Amit, A.G. et al.; "Tree-Dimensional Structure of an Antigen-Antibody Complex at 2.8 Å Resolution"; *Science*; 1986: vol. 233: pp. 747-753.

(Continued)

*Primary Examiner* — Chun W Dahle
(74) *Attorney, Agent, or Firm* — Finnegan, Henderson, Farabow, Garrett & Dunner, LLP

(57) ABSTRACT

The present invention relates to novel stabilized IgG4 antibodies, to methods of producing such antibodies and to uses of such antibodies as a medicament. In a main aspect, the invention relates to a stabilized IgG4 antibody, comprising a heavy chain and a light chain, wherein said heavy chain comprises a human IgG4 constant region having a substitution of the Arg residue at position (409), the Phe residue at position (405) or the Lys residue at position (370).

11 Claims, 23 Drawing Sheets

Specification includes a Sequence Listing.

(56) References Cited

OTHER PUBLICATIONS

Angal, S. et al.; "A single amino acid substitution abolishes the heterogeneity of chimeric mouse/humane (IgG4) antibody"; *Molecular Immunology*; Jan. 1, 1993; vol. 30, No. 1; pp. 105-108.

Bloom, J.W. et al.; "Intrachain disulfide bond in the core hinge region of human IgG4"; *Protein Science*; Feb. 1997; vol. 6, No. 2; pp. 407-415.

Bonnin, E. et al., "Generation of functional scFv intrabodies for triggering anti-tumor immunity"; *Methods*; 2004; vol. 34, Issue 2; pp. 225-232.

Brekke et al.; *Immunologist*, vol. 2; pp. 125-130, 1994.

Brusco, A. et al.; "Molecular characterization of Immunoglobulin G4 gene isoallotypes" *European Journal of Immunogenectics*; 1998; vol. 25: pp. 349-355.

Ciccimarra, F. et al.; "Localization of the IgG Effector Site for Monocyte Receptors"; *Proc. Nat. Acad. Sci. USA*; Jun. 1975; vol. 72. No. 6; pp. 2081-2083.

Correia, I.R.; "Stability of IG Isotypes in serum", *mAbs*; May/Jun. 2010; vol. 2, No. 3; pp. 221-232.

Dall'Acqua, W. et al.; "Contribution of Domain Interface Residues to the Stability of Antibody $C_H3$ Domain Homodimers"; *Biochemistry*; 1998, vol. 37, No. 28; pp. 9266-9273.

Dall'Acqua, W. et al.; "A Mutational Analysis of Binding Interactions in an Antigen-Antibody Protein-Protein Complex"; *Biochemistry*; 1996; vol. 37, No. 22; pp. 7981-7991.

Dall'Acqua, W. et al.; "Modulation of the Effector Functions of a Human IgG1 through Engineering of Its Hinge Region"; *The Journal of Immunology*; 2006; vol. 177, No. 2; pp. 1129-1138.

Deng, L. et al.; "Detection and quantification of the human IgG4 half-molecule, HL, from unpurified cell-culture supernatants"; *Biotechnology and Applied Biochemistry*; Dec. 1, 2004; vol. 40, No. 3, pp. 261-269.

European Patent No. 2164873 (Application No. 08748828.4), filed. May 30. 2008, by Genmab/A/S: Summons to attend oral proceedings, with accompanying communication, Jul. 15, 2014; 8 pages.

European Patent No. 2164873 (Application No. 08748628.4), filed May 30, 2006, by Genmab/A/S: Notice of Opposition by EIP Limited, Jun. 29, 2016; 23 pages.

Goldenberg, D. et al.; "Cancer imaging and therapy with bispecific antibody pretargeting"; *Update Cancel Ther.*; Mar. 2007; vol. 2, No. 1; pp. 19-31.

Hammarström, L. et al.; "The Use of Intravenous IgG as Prophylaxis and for Treatment of Infections"; *Infection*; 1990; vol. 18, No. 5; pp. 314-324.

Haringman, J. et al.; "A randomized controlled trial with an anti-CCL2 (anti-monocyte chemotactic protein 1) monoclonal antibody in patients with rheumatoid arthritis": *Arthritis and Rheumatism*; Aug. 2006; vol. 54, No. 8; pp. 2387-2392.

Horgan, C. et al.; "Studies on antigen binding by intact and hinge-deleted chimeric antibodies"; *The Journal of Immunology*; June 15, 1993; vol. 150, No. 12; pp. 5400-5407.

Huck, S. et al.; "Sequence of a human immunoglobulin gamma 3 heavy chain constant region gene: comparison with the other Cγ genes"; *Nucl. Acids Res.*; Jan. 1, 1986; Vo. 14, No. 4; pp. 1779-1789.

International Search Report dated Oct. 29, 2008; for International Application No. PCT/DK2008/050129; 4 pages.

Written Opinion dated Oct. 29, 2008; for International Application No. PCT/DK2008/050129; 5 pages.

Isaacs, J.D. et al.; "A therapeutic human IgG4 monoclonal antibody that depletes target cells in humans"; *Clin. Exp. Immunol.*; 1996; vol. 106; pp. 427-433.

Japanese Office Action for Japanese Patent Application No. 2014-016803 dated Mar. 11, 2015; 9 pages.

Labrijn, A. et al.; "Therapeutic IgG4 antibodies engage in Fab-arm exchange with endogenous human IgG4 in vivo"; *Nature Biotechnology*; Aug. 2009; vol. 27, No. 8; pp. 767-771.

Rispens, T. et al.; "Dynamics of Inter-heavy Chain Interactios in Human Immunoglobulin G (IgG) Subclasses Studied by Kinetic Fab Arm Exchange"*J. Biol. Chem.*; Feb. 28, 2014; vol. 289, No. 9; pp. 6098-6109.

Schuurman, J. et al.; "Normal human imunoglobulin G4 is bispecific: it has two different antigen-combining sites"; *Immunology*; 1999; vol. 97; pp. 693-698.

Schuurman, J. et al.; "The inter-heavy chain disulfide bonds of IgG4 are in equillbrium with intra-chain disulfide bonds"; *Mol. Immunol.*; 2001; vol. 38; pp. 1-8.

Scinicariello, F. et al.; "Rhesus macaque antibody molecules; sequences and heterogeneity of alpha and gamma constant regions"; *Immunology*; 2004; vol. 111; pp. 66-74.

Sheridan, C.; "Pharma consolidates its grip on post-antibody landscape"; *Nature Biotechnology*; Apr. 2007; vol. 25, No. 4, pp. 365-366.vol. 25, No. 4; pp. 365-366.

Shields, R.L. et al.; "High Resolution Mapping of the Binding Site on Human IgG1 for FcγRI, FcγRII, FcγRIII, and FcRn and Design of IgG1 Variants with Improved Binding to the FcγR"; *J. Biol. Chem.*; Mar. 2, 2001; vol. 276, No. 9; pp. 6591-6604.

Vajdos, F. et al.; "Comprehensive Functional Maps of the Antigen-binding Site of an Anti-ErbB2 Antibody Obtained with Shotgun Scanning Mutagenesis" *J. Mol. Biol.*: vol. 320; pp. 415-428.

Van Der Neut Kolfschoten, M. et al.; "Anti-Inflammatory Activity of Human IgG4 Antibodies by Dynamic Fab Arm Exchange"; *Science*; 2007; vol. 317; pp. 1554-1557.

Van Der Zee, J. et al.; "Serologic Aspects of IgG4 Antibodies, II. IgG4 Antibodies Form Small, Nonprecipitating Immune Complexes Due to Functional Monovalency"; *J. Immunol.*; Dec. 1, 1986; vol. 137, No. 11; pp. 3566-3571.

Zuckier et al.; "Chimeric Human-Mouse IgG Antibodies with Shuffled Coonstant Region Exons Demonstrate that Multiple Domains Contribute to in Vivo Half-Life"; *Cancer*; 1998; vol. 58; pp. 3905-3906.

\* cited by examiner

```
ED         3         3         3                 3         3         3         3         3         4
           0         1         2                 3         4         5         6         7         8         9         0
           1234567890123456789012 3456 78901 234567 8901234567890123456789 012345 6 7890123456789 01234 56 7890123456789 0
2F8-G1     RVVSVLTVLHQDWLNGKEYKCKVSNKALPAPI-EKTI-SKAKG-QPREPQVYTLPPSRDE---LTKNQVSLTCLVKGFYPSDIAV---EWESN-GQ---PENNYKTTPPVLDS
2F8-G4     RVVSVLTVLHQDWLNGKEYKCKVSNKGLPSSI-EKTI-SKAKG-QPREPQVYTLPPSQEE---MTKNQVSLTCLVKGFYPSDIAV---EWESN-GQ---PENNYKTTPPVLDS
KABAT      3         3         3                 3         3         3         4         4         4         4         4
           2         3         4                 5         6         7         0         1         2         3         4
           0123456789012345678901234567890123456789012345678901234567890123456789012345678901234567890123456789012345678
                                                                                                    A

EU         4         4         4         4
           0         1         2         3
           1 234567890123456789012345678901234567890123456
2F8-G1     --D---GSFFLYSKLTVDKSRWQQGNVFSCSVMHEALHNHYTQKSLSLSPGK
2F8-G4     --D---GSFFLYSRLTVDKSRWQEGNVFSCSVMHEALHNHYTQKSLSLSLGK
KABAT      4         4         4         5
           5         6         7         0
           9012345678901234567890123456789012345678901234567 8
```

SEQUENCE LISTING

<160> NUMBER OF SEQ ID NOS: 52

<210> SEQ ID NO 1

```
<211> LENGTH: 36
<212> TYPE: DNA
<213> ORGANISM: artificial
<220> FEATURE:
<223> OTHER INFORMATION: primer

<400> SEQUENCE: 1
agccaccgta cgtttgattt ccagcttggt gcctcc                                  36

<210> SEQ ID NO 2
<211> LENGTH: 44
<212> TYPE: DNA
<213> ORGANISM: artificial
<220> FEATURE:
<223> OTHER INFORMATION: primer

<400> SEQUENCE: 2
gatgcaagct tgccgccacc atggagtcac agattcaggc attt                          44

<210> SEQ ID NO 3
<211> LENGTH: 42
<212> TYPE: DNA
<213> ORGANISM: artificial
<220> FEATURE:
<223> OTHER INFORMATION: primer

<400> SEQUENCE: 3
cgatgggccc ttggtgctgg ctgaggagac ggtgactgag gt                            42

<210> SEQ ID NO 4
<211> LENGTH: 44
<212> TYPE: DNA
<213> ORGANISM: artificial
<220> FEATURE:
<223> OTHER INFORMATION: primer

<400> SEQUENCE: 4
gatgcaagct tgccgccacc atgaaatgca gctgggttat cttc                          44

<210> SEQ ID NO 5
<211> LENGTH: 36
<212> TYPE: DNA
<213> ORGANISM: artificial
<220> FEATURE:
<223> OTHER INFORMATION: primer

<400> SEQUENCE: 5
agccaccgta cgttttattt ccaactttgt ccccga                                  36

<210> SEQ ID NO 6
<211> LENGTH: 44
<212> TYPE: DNA
<213> ORGANISM: artificial
<220> FEATURE:
<223> OTHER INFORMATION: primer

<400> SEQUENCE: 6
gatgcaagct tgccgccacc atggaatcac agactcaggt cctc                          44

<210> SEQ ID NO 7
<211> LENGTH: 42
<212> TYPE: DNA
<213> ORGANISM: artificial
<220> FEATURE:
<223> OTHER INFORMATION: primer

<400> SEQUENCE: 7
```
cgatgggccc ttggtgctgg ctgcagagaa agtgaccaga gt                          42

<210> SEQ ID NO 8
<211> LENGTH: 44
<212> TYPE: DNA
<213> ORGANISM: artificial
<220> FEATURE:
<223> OTHER INFORMATION: primer

<400> SEQUENCE: 8
gatgcaagct tgccgccacc atgggatgga gctatatcat cctc                        44

<210> SEQ ID NO 9
<211> LENGTH: 32
<212> TYPE: DNA
<213> ORGANISM: artificial
<220> FEATURE:
<223> OTHER INFORMATION: primer

<400> SEQUENCE: 9
tgagaattcg gtgggtgctt tatttccatg ct                                     32

<210> SEQ ID NO 10
<211> LENGTH: 33
<212> TYPE: DNA
<213> ORGANISM: artificial
<220> FEATURE:
<223> OTHER INFORMATION: primer

<400> SEQUENCE: 10
gtagaagctt accatcgcgg atagacaaga acc                                    33

<210> SEQ ID NO 11
<211> LENGTH: 26
<212> TYPE: DNA
<213> ORGANISM: artificial
<220> FEATURE:
<223> OTHER INFORMATION: primer

<400> SEQUENCE: 11
tgttaactgc tcactggatg gtggga                                            26

<210> SEQ ID NO 12
<211> LENGTH: 27
<212> TYPE: DNA
<213> ORGANISM: artificial
<220> FEATURE:
<223> OTHER INFORMATION: primer

<400> SEQUENCE: 12
tccctgggca caatttctt gtccacc                                            27

<210> SEQ ID NO 13
<211> LENGTH: 31
<212> TYPE: DNA
<213> ORGANISM: artificial
<220> FEATURE:
<223> OTHER INFORMATION: primer

<400> SEQUENCE: 13
tgaaagcttc taatacgact cactataggg c                                      31

<210> SEQ ID NO 14
<211> LENGTH: 54
<212> TYPE: DNA

<213> ORGANISM: artificial
<220> FEATURE:
<223> OTHER INFORMATION: primer

<400> SEQUENCE: 14
tgaaagcttc taatacgact cactataggg caagcagtgg tatcaacgca gagt        54

<210> SEQ ID NO 15
<211> LENGTH: 137
<212> TYPE: PRT
<213> ORGANISM: artificial
<220> FEATURE:
<223> OTHER INFORMATION: variable region sequence of antibody

<400> SEQUENCE: 15

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
        35                  40                  45

Lys Asp Thr Tyr Ile His Trp Val Lys Gln Arg Pro Glu Gln Gly Leu
    50                  55                  60

Glu Trp Val Gly Arg Ile Asp Pro Ala Thr Gly Asn Thr Arg Tyr Asp
65                  70                  75                  80

Pro Lys Phe Gln Gly Lys Ala Thr Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Ser Phe Arg Pro Gly Tyr Ala Leu Asp Tyr Trp Gly
        115                 120                 125

Gln Gly Thr Ser Val Thr Val Ser Ser
    130                 135

<210> SEQ ID NO 16
<211> LENGTH: 127
<212> TYPE: PRT
<213> ORGANISM: artificial
<220> FEATURE:
<223> OTHER INFORMATION: variable region sequence of antibody

<400> SEQUENCE: 16

Met Glu Ser Gln Ile Gln Ala Phe Val Phe Val Phe Leu Trp Leu Ser
1               5                   10                  15

Gly Val Asp Gly Asp Ile Val Met Thr Gln Ser His Lys Phe Met Ser
            20                  25                  30

Thr Ser Val Gly Asp Arg Val Ser Phe Thr Cys Lys Ala Ser Gln Asp
        35                  40                  45

Val Phe Thr Ala Val Ala Trp Tyr Gln Gln Lys Pro Gly Gln Ser Pro
    50                  55                  60

Lys Leu Leu Ile Tyr Trp Ala Ser Thr Arg Arg Thr Gly Val Pro Asp
65                  70                  75                  80

Arg Phe Thr Gly Ser Gly Ser Gly Thr Asp Tyr Thr Leu Thr Ile Ser
                85                  90                  95

Ser Val Gln Ala Glu Asp Leu Ala Leu Tyr Tyr Cys Gln Gln His Phe
            100                 105                 110

Ser Thr Pro Pro Thr Phe Gly Gly Gly Thr Lys Leu Glu Ile Lys
        115                 120                 125

<210> SEQ ID NO 17
<211> LENGTH: 138
<212> TYPE: PRT
<213> ORGANISM: artificial
<220> FEATURE:
<223> OTHER INFORMATION: variable region sequence of antibody

<400> SEQUENCE: 17

Met Gly Trp Ser Tyr Ile Ile Leu Phe Leu Val Ala Thr Ala Thr Asp
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Ser Phe
        35                  40                  45

Thr Ser Tyr Trp Met His Trp Leu Lys Gln Arg Pro Gly Gln Gly Leu
    50                  55                  60

Glu Trp Ile Gly Glu Ile Asn Pro Asn Asn Gly Arg Thr Tyr Tyr Asn
65                  70                  75                  80

Glu Lys Phe Lys Thr Lys Ala Thr Leu Thr Val Asp Lys Ser Ser Ser
                85                  90                  95

Thr Ala Tyr Met Gln Leu Asn Ser Leu Thr Ser Glu Asp Ser Ala Val
            100                 105                 110

Tyr Tyr Cys Ala Arg Arg Leu Thr Met Val Glu Ser Phe Ala Tyr Trp
        115                 120                 125

Gly Gln Gly Thr Leu Val Thr Phe Ser Ala
    130                 135

<210> SEQ ID NO 18
<211> LENGTH: 133
<212> TYPE: PRT
<213> ORGANISM: artificial
<220> FEATURE:
<223> OTHER INFORMATION: variable region sequence of antibody

<400> SEQUENCE: 18

Met Glu Ser Gln Thr Gln Val Leu Met Ser Leu Leu Phe Trp Val Ser
1               5                   10                  15

Gly Thr Cys Gly Asp Ile Val Met Thr Gln Ser Pro Ser Ser Leu Thr
            20                  25                  30

Val Thr Ala Gly Glu Lys Val Thr Met Ser Cys Lys Ser Ser Gln Ser
        35                  40                  45

Leu Leu Asn Ser Gly Asn Gln Lys Asn Tyr Leu Thr Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Ser Leu Thr Ile Ser Ser Val Gln Ala Glu Asp Leu Ala Ile Tyr
            100                 105                 110

Tyr Cys Gln Asn Asp Tyr Ser Tyr Pro Phe Thr Phe Gly Ser Gly Thr
        115                 120                 125

Lys Leu Glu Ile Lys
    130

<210> SEQ ID NO 19
<211> LENGTH: 45
<212> TYPE: DNA
<213> ORGANISM: artificial

<220> FEATURE:
<223> OTHER INFORMATION: primer

<400> SEQUENCE: 19
cttgtgacaa aactcacacc tgcccatcgt gcccaggtaa gccag    45

<210> SEQ ID NO 20
<211> LENGTH: 45
<212> TYPE: DNA
<213> ORGANISM: artificial
<220> FEATURE:
<223> OTHER INFORMATION: primer

<400> SEQUENCE: 20
ctggcttacc tgggcacgat gggcaggtgt gagttttgtc acaag    45

<210> SEQ ID NO 21
<211> LENGTH: 43
<212> TYPE: DNA
<213> ORGANISM: artificial
<220> FEATURE:
<223> OTHER INFORMATION: primer

<400> SEQUENCE: 21
cccccatgcc caccatgccc aggtaagcca acccaggcct cgc    43

<210> SEQ ID NO 22
<211> LENGTH: 43
<212> TYPE: DNA
<213> ORGANISM: artificial
<220> FEATURE:
<223> OTHER INFORMATION: primer

<400> SEQUENCE: 22
gcgaggcctg ggttggctta cctgggcatg gtgggcatgg ggg    43

<210> SEQ ID NO 23
<211> LENGTH: 45
<212> TYPE: DNA
<213> ORGANISM: artificial
<220> FEATURE:
<223> OTHER INFORMATION: primer

<400> SEQUENCE: 23
cttgtgacaa aactcacacc tgcccatcgt gcccaggtaa gccag    45

<210> SEQ ID NO 24
<211> LENGTH: 45
<212> TYPE: DNA
<213> ORGANISM: artificial
<220> FEATURE:
<223> OTHER INFORMATION: primer

<400> SEQUENCE: 24
ctggcttacc tgggcacgat gggcaggtgt gagttttgtc acaag    45

<210> SEQ ID NO 25
<211> LENGTH: 45
<212> TYPE: DNA
<213> ORGANISM: artificial
<220> FEATURE:
<223> OTHER INFORMATION: primer

<400> SEQUENCE: 25
ccttcttcct ctatagcagg ctcaccgtag acaagagcag gtggc    45

<210> SEQ ID NO 26
<211> LENGTH: 45
<212> TYPE: DNA
<213> ORGANISM: artificial
<220> FEATURE:
<223> OTHER INFORMATION: primer

<400> SEQUENCE: 26
gccacctgct cttgtctacg gtgagcctgc tatagaggaa gaagg          45

<210> SEQ ID NO 27
<211> LENGTH: 45
<212> TYPE: DNA
<213> ORGANISM: artificial
<220> FEATURE:
<223> OTHER INFORMATION: primer

<400> SEQUENCE: 27
ggctccttct tcctctacag caagctaacc gtagacaaga gcagg          45

<210> SEQ ID NO 28
<211> LENGTH: 45
<212> TYPE: DNA
<213> ORGANISM: artificial
<220> FEATURE:
<223> OTHER INFORMATION: primer

<400> SEQUENCE: 28
cctgctcttg tctacggtta gcttgctgta gaggaagaag gagcc          45

<210> SEQ ID NO 29
<211> LENGTH: 20
<212> TYPE: DNA
<213> ORGANISM: artificial
<220> FEATURE:
<223> OTHER INFORMATION: primer

<400> SEQUENCE: 29
tctcctcagc cagcaccaag          20

<210> SEQ ID NO 30
<211> LENGTH: 23
<212> TYPE: DNA
<213> ORGANISM: artificial
<220> FEATURE:
<223> OTHER INFORMATION: primer

<400> SEQUENCE: 30
gtttgtctgc agccagcacc aag          23

<210> SEQ ID NO 31
<211> LENGTH: 25
<212> TYPE: DNA
<213> ORGANISM: artificial
<220> FEATURE:
<223> OTHER INFORMATION: primer

<400> SEQUENCE: 31
catctccaaa gccaaaggtg ggacc          25

<210> SEQ ID NO 32
<211> LENGTH: 25
<212> TYPE: DNA
<213> ORGANISM: artificial
<220> FEATURE:
<223> OTHER INFORMATION: primer

```
<400> SEQUENCE: 32
ggtcccacct ttggctttgg agatg                                          25

<210> SEQ ID NO 33
<211> LENGTH: 24
<212> TYPE: DNA
<213> ORGANISM: artificial
<220> FEATURE:
<223> OTHER INFORMATION: primer

<400> SEQUENCE: 33
cgacggctcc ttcttcctct acag                                           24

<210> SEQ ID NO 34
<211> LENGTH: 24
<212> TYPE: DNA
<213> ORGANISM: artificial
<220> FEATURE:
<223> OTHER INFORMATION: primer

<400> SEQUENCE: 34
ctgtagagga agaaggagcc gtcg                                           24

<210> SEQ ID NO 35
<211> LENGTH: 23
<212> TYPE: DNA
<213> ORGANISM: artificial
<220> FEATURE:
<223> OTHER INFORMATION: primer

<400> SEQUENCE: 35
caagagccat atccgggagg acc                                            23

<210> SEQ ID NO 36
<211> LENGTH: 23
<212> TYPE: DNA
<213> ORGANISM: artificial
<220> FEATURE:
<223> OTHER INFORMATION: primer

<400> SEQUENCE: 36
ggtcctcccg gatatggctc ttg                                            23

<210> SEQ ID NO 37
<211> LENGTH: 20
<212> TYPE: DNA
<213> ORGANISM: artificial
<220> FEATURE:
<223> OTHER INFORMATION: primer

<400> SEQUENCE: 37
gtcagaggta actcccgttg                                                20

<210> SEQ ID NO 38
<211> LENGTH: 20
<212> TYPE: DNA
<213> ORGANISM: artificial
<220> FEATURE:
<223> OTHER INFORMATION: primer

<400> SEQUENCE: 38
gttgtggttt gtccaaactc                                                20

<210> SEQ ID NO 39
```

<211> LENGTH: 327
<212> TYPE: PRT
<213> ORGANISM: homo sapiens

<400> SEQUENCE: 39

| Ala | Ser | Thr | Lys | Gly | Pro | Ser | Val | Phe | Pro | Leu | Ala | Pro | Cys | Ser | Arg |
|---|---|---|---|---|---|---|---|---|---|---|---|---|---|---|---|
| 1 | | | | 5 | | | | | 10 | | | | | 15 | |

| Ser | Thr | Ser | Glu | Ser | Thr | Ala | Ala | Leu | Gly | Cys | Leu | Val | Lys | Asp | Tyr |
| | | | 20 | | | | | 25 | | | | | 30 | | |

| Phe | Pro | Glu | Pro | Val | Thr | Val | Ser | Trp | Asn | Ser | Gly | Ala | Leu | Thr | Ser |
| | | | 35 | | | | | 40 | | | | | 45 | | |

| Gly | Val | His | Thr | Phe | Pro | Ala | Val | Leu | Gln | Ser | Ser | Gly | Leu | Tyr | Ser |
| | 50 | | | | | 55 | | | | | 60 | | | | |

| Leu | Ser | Ser | Val | Val | Thr | Val | Pro | Ser | Ser | Ser | Leu | Gly | Thr | Lys | Thr |
| 65 | | | | | 70 | | | | | 75 | | | | | 80 |

| Tyr | Thr | Cys | Asn | Val | Asp | His | Lys | Pro | Ser | Asn | Thr | Lys | Val | Asp | Lys |
| | | | | 85 | | | | | 90 | | | | | 95 | |

| Arg | Val | Glu | Ser | Lys | Tyr | Gly | Pro | Pro | Cys | Pro | Ser | Cys | Pro | Ala | Pro |
| | | | 100 | | | | | 105 | | | | | 110 | | |

| Glu | Phe | Leu | Gly | Gly | Pro | Ser | Val | Phe | Leu | Phe | Pro | Pro | Lys | Pro | Lys |
| | | | 115 | | | | | 120 | | | | | 125 | | |

| Asp | Thr | Leu | Met | Ile | Ser | Arg | Thr | Pro | Glu | Val | Thr | Cys | Val | Val | Val |
| | 130 | | | | | 135 | | | | | 140 | | | | |

| Asp | Val | Ser | Gln | Glu | Asp | Pro | Glu | Val | Gln | Phe | Asn | Trp | Tyr | Val | Asp |
| 145 | | | | | 150 | | | | | 155 | | | | | 160 |

| Gly | Val | Glu | Val | His | Asn | Ala | Lys | Thr | Lys | Pro | Arg | Glu | Glu | Gln | Phe |
| | | | | 165 | | | | | 170 | | | | | 175 | |

| Asn | Ser | Thr | Tyr | Arg | Val | Val | Ser | Val | Leu | Thr | Val | Leu | His | Gln | Asp |
| | | | 180 | | | | | 185 | | | | | 190 | | |

| Trp | Leu | Asn | Gly | Lys | Glu | Tyr | Lys | Cys | Lys | Val | Ser | Asn | Lys | Gly | Leu |
| | | | 195 | | | | | 200 | | | | | 205 | | |

| Pro | Ser | Ser | Ile | Glu | Lys | Thr | Ile | Ser | Lys | Ala | Lys | Gly | Gln | Pro | Arg |
| | 210 | | | | | 215 | | | | | 220 | | | | |

| Glu | Pro | Gln | Val | Tyr | Thr | Leu | Pro | Pro | Ser | Gln | Glu | Glu | Met | Thr | Lys |
| 225 | | | | | 230 | | | | | 235 | | | | | 240 |

| Asn | Gln | Val | Ser | Leu | Thr | Cys | Leu | Val | Lys | Gly | Phe | Tyr | Pro | Ser | Asp |
| | | | | 245 | | | | | 250 | | | | | 255 | |

| Ile | Ala | Val | Glu | Trp | Glu | Ser | Asn | Gly | Gln | Pro | Glu | Asn | Asn | Tyr | Lys |
| | | | 260 | | | | | 265 | | | | | 270 | | |

| Thr | Thr | Pro | Pro | Val | Leu | Asp | Ser | Asp | Gly | Ser | Phe | Phe | Leu | Tyr | Ser |
| | | | 275 | | | | | 280 | | | | | 285 | | |

| Arg | Leu | Thr | Val | Asp | Lys | Ser | Arg | Trp | Gln | Glu | Gly | Asn | Val | Phe | Ser |
| | 290 | | | | | 295 | | | | | 300 | | | | |

| Cys | Ser | Val | Met | His | Glu | Ala | Leu | His | Asn | His | Tyr | Thr | Gln | Lys | Ser |
| 305 | | | | | 310 | | | | | 315 | | | | | 320 |

| Leu | Ser | Leu | Ser | Leu | Gly | Lys |
| | | | | 325 | | |

<210> SEQ ID NO 40
<211> LENGTH: 327
<212> TYPE: PRT
<213> ORGANISM: homo sapiens

<400> SEQUENCE: 40

| Ala | Ser | Thr | Lys | Gly | Pro | Ser | Val | Phe | Pro | Leu | Ala | Pro | Cys | Ser | Arg |
|---|---|---|---|---|---|---|---|---|---|---|---|---|---|---|---|
| 1 | | | | 5 | | | | | 10 | | | | | 15 | |

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Ser Cys Pro Ala Pro
        100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 41
<211> LENGTH: 327
<212> TYPE: PRT
<213> ORGANISM: homo sapiens

<400> SEQUENCE: 41

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
```

```
                50                  55                  60
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Val His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 42
<211> LENGTH: 48
<212> TYPE: DNA
<213> ORGANISM: artificial
<220> FEATURE:
<223> OTHER INFORMATION: primer

<400> SEQUENCE: 42
ccagtgctgg acagcgacgg aagcttcgcc ctgtacagca ggctgacc            48

<210> SEQ ID NO 43
<211> LENGTH: 48
<212> TYPE: DNA
<213> ORGANISM: artificial
<220> FEATURE:
<223> OTHER INFORMATION: primer

<400> SEQUENCE: 43
ggtcagcctg ctgtacaggg cgaagcttcc gtcgctgtcc agcactgg             48

<210> SEQ ID NO 44
```

<211> LENGTH: 51
<212> TYPE: DNA
<213> ORGANISM: artificial
<220> FEATURE:
<223> OTHER INFORMATION: primer

<400> SEQUENCE: 44
ccagtgctgg acagcgacgg atccttctta ctgtacagca ggctgaccgt g                51

<210> SEQ ID NO 45
<211> LENGTH: 51
<212> TYPE: DNA
<213> ORGANISM: artificial
<220> FEATURE:
<223> OTHER INFORMATION: primer

<400> SEQUENCE: 45
cacggtcagc ctgctgtaca gtaagaagga tccgtcgctg tccagcactg g                51

<210> SEQ ID NO 46
<211> LENGTH: 46
<212> TYPE: DNA
<213> ORGANISM: artificial
<220> FEATURE:
<223> OTHER INFORMATION: primer

<400> SEQUENCE: 46
gctccttctt cctgtacagc gcgttaaccg tggacaagtc caggtg                       46

<210> SEQ ID NO 47
<211> LENGTH: 46
<212> TYPE: DNA
<213> ORGANISM: artificial
<220> FEATURE:
<223> OTHER INFORMATION: primer

<400> SEQUENCE: 47
cacctggact tgtccacggt taacgcgctg tacaggaaga aggagc                       46

<210> SEQ ID NO 48
<211> LENGTH: 45
<212> TYPE: DNA
<213> ORGANISM: artificial
<220> FEATURE:
<223> OTHER INFORMATION: primer

<400> SEQUENCE: 48
ctccttcttc ctgtacagca agcttaccgt ggacaagtcc aggtg                        45

<210> SEQ ID NO 49
<211> LENGTH: 45
<212> TYPE: DNA
<213> ORGANISM: artificial
<220> FEATURE:
<223> OTHER INFORMATION: primer

<400> SEQUENCE: 49
cacctggact tgtccacggt aagcttgctg tacaggaaga aggag                        45

<210> SEQ ID NO 50
<211> LENGTH: 4
<212> TYPE: PRT
<213> ORGANISM: homo sapiens

<400> SEQUENCE: 50

Cys Pro Pro Cys

```
<210> SEQ ID NO 51
<211> LENGTH: 4
<212> TYPE: PRT
<213> ORGANISM: homo sapiens

<400> SEQUENCE: 51

Cys Pro Ser Cys
1

<210> SEQ ID NO 52
<211> LENGTH: 4
<212> TYPE: PRT
<213> ORGANISM: homo sapiens

<400> SEQUENCE: 52

Cys Pro Arg Cys
1
```

US 10,752,695 B2

STABLE IGG4 ANTIBODIES

RELATED APPLICATIONS

This is a continuation of U.S. application Ser. No. 13/912,581 filed Jun. 7, 2013, which is a Division of U.S. application Ser. No. 12/602,439 filed Jul. 1, 2010, which is a National Stage Entry of PCT/DK2008/050129 filed May 30, 2008, and claims the benefit of priority of Denmark Patent Application No. PA 2007 00792 filed May 31, 2007, Denmark Patent Application No. PA 2007 00793 filed May 31, 2007, and Denmark Patent Application No. PA 2007 01002 filed Jul. 6, 2007, all of which are incorporated herein by reference in their entirety.

All patents, patent applications and other publications cited herein are hereby incorporated by reference in their entirety.

FIELD OF THE INVENTION

The present invention relates to novel stabilized IgG4 antibodies, to methods of producing such antibodies and to uses of such antibodies as a medicament.

BACKGROUND OF THE INVENTION

Antibodies are being used as therapeutic agents for a number of diseases and disorders, including cancer and autoimmune diseases. Antibodies are immunoglobulins that recognize specific antigens and mediate their effects via several mechanisms, including inhibition of ligand-receptor interactions, inhibition of receptor activation, mediation of receptor internalization and activation of effector functions, such as complement-dependent cytotoxicity (CDC) and antibody-dependent cellular cytotoxicity (ADCC). There are five classes of immunoglobulins: IgG, IgA, IgM, IgD and IgE. The IgG class is further divided into subclasses IgG1, IgG2, IgG3 and IgG4.

Human IgG4 molecules are heterogeneous and exist in various molecular forms, which differ by the absence or presence of inter-heavy chain disulphide bonds located in the hinge region. Thus, IgG4 molecules exist in forms in which either both or none of the inter-heavy chain disulphide bonds have been formed, a process which is in equilibrium (Schuurman et al. (2001) Mol Immunol 38:1; Bloom et al (1997) Protein Sci 6:407). The form lacking inter-heavy chain disulphide bonds consists of one heavy chain and one light chain, and is termed "half-molecule" or "Fab arm" herein. The heterogeneity of IgG4s is believed to be related to the core sequence of the IgG4 hinge region which, instead of Cys-Pro-Pro-Cys (SEQ ID NO:50), as in IgG1 and IgG2, consists of Cys-Pro-Ser-Cys (SEQ ID NO:51), which is believed to be a more flexible structure. Data that support the role of the core hinge sequence in this heterogeneity of IgG4 have been reported by Angal et al. (1993) Mol Immunol 30:105. In this study, it was shown that by replacement of a Ser residue in the hinge region to a Pro residue, thus changing the core hinge sequence to Cys-Pro-Pro-Cys (SEQ ID NO:50) (which is identical to that of IgG1 and IgG2), the presence of IgG4 half molecules was abolished.

It has been known for several years that IgG4 antibodies, unlike other IgG subclasses, behave as monovalent molecules in interactions with antigen. It was found that serum-derived human IgG4 cannot precipitate purified antigen, because it cannot crosslink. While such serum-derived IgG4 is functionally monovalent (Aalberse et al. (1983) 3 Immunol 130:722; van der Zee et al. (1986) 3 Immunol 137:3566), recombinantly produced, isolated IgG4, in contrast, is behaving bivalently in interactions with antigens (Schuurman et al (1999) Immunology 97:693). Furthermore, IgG4 antibodies with bispecific reactivity were shown to exist in sera from allergic patients expressing large amounts of IgG4 antibodies against two different antigens (Schuurman et al (1999) Immunology 97:693; Aalberse and Schuurman (2002) Immunology 105:9; Aalberse et al (1999) Int Arch Allergy Immunol 118:187). On basis of these observations, it was hypothesized that IgG4 antibodies can exchange 'half-molecules', an activity termed Fab arm exchange herein.

Several different allotypes of human IgG4 have been found to exist. One of these allotypes contains a Leu residue at position 309 and a Lys residue at position 409, which in other allotypes is an Arg residue (Brusco et al (1998) Eur 3 Immunogen 25:349). In WO2006/033386, it has been shown that an IgG4 antibody could be rendered more stable at low pH by introduction of an Arg to Lys mutation at position 409 into an antibody context that also contained mutations of the hinge region, including the above mentioned mutation of the core sequence to Cys-Pro-Pro-Cys (SEQ ID NO:50).

IgG4 antibodies have a poor ability to induce complement and cell activation because of a low affinity for C1q and Fc-receptors. This makes IgG4 the preferred isotype for development of immunotherapies in which recruitment of host effector functions is not desired.

However, for any therapeutic use of an antibody, a high degree of in vivo stability of the antibody is desired.

SUMMARY OF THE INVENTION

It is demonstrated in the present patent application that administration of two recombinant monoclonal IgG4 antibodies having different antigen-binding specificities to a mouse leads to in vivo formation of bispecific antibodies. The phenomenon can be reproduced in vitro by incubating IgG4 antibodies with cells or under reducing conditions. It was shown that IgG4 antibodies having different antigen-binding specificities engage in Fab arm exchange which is stochastic and in which all IgG4 molecules seem to participate. Thus IgG4 antibodies form bispecific antibodies without concomitant formation of aggregates.

IgG4 antibodies therefore have unusual properties which are undesirable in vivo: IgG4 antibodies are unstable, dynamic, molecules which engage in Fab arm exchange. An administered therapeutic IgG4 antibody may exchange with endogenous IgG4 antibodies with undesired specificities. The random nature of this process introduces unpredictability which is highly undesirable for human immunotherapy.

The present invention relates to stabilized forms of IgG4 antibodies that have a reduced ability to undergo Fab-arm exchange. It has surprisingly been found that substitution of the Arg residue at position 409 or the Phe residue at position 405 in human IgG4 can prevent Fab arm exchange, and thus stabilize IgG4, even in the absence of a mutation of the core hinge region sequence to Cys-Pro-Pro-Cys (SEQ ID NO:50). This was unexpected, because it was believed that elimination of the flexibility of the hinge region via a change of the core hinge sequence to Cys-Pro-Pro-Cys (SEQ ID NO:50) was a requirement for prevention of half-molecule exchange.

Accordingly, in a main aspect, the invention relates to a stabilized IgG4 antibody for use as a medicament, comprising a heavy chain and a light chain, wherein said heavy chain comprises a human IgG4 constant region having a substitution of the Arg residue at position 409, the Phe residue at position 405 or the Lys residue at position 370, wherein said antibody optionally comprises one or more further substitutions, deletions and/or insertions, with the proviso that if the antibody has a residue selected from the group consisting of: Lys, Ala, Thr, Met and Leu at the position corresponding to 409, then the antibody does not comprise a Cys-Pro-Pro-Cys sequence (SEQ ID NO:50) in the hinge region.

The substitutions at positions 409, 405 and 370 can be present individually or in any combination.

In a main embodiment, the invention relates to an isolated stabilized IgG4 antibody for use as a medicament, comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions, but does not comprise a Cys-Pro-Pro-Cys sequence (SEQ ID NO:50) in the hinge region.

In several embodiments, the antibodies used in the invention have the advantage that they contain a minimal number of sequence changes in the constant region as compared to naturally occurring IgG4. This reduces the risk of immunogenicity when the antibody is used for human therapy.

In one particular embodiment, the constant region of the stabilized IgG4 antibody of the invention is even identical to that of the above mentioned Lys409 allotype described by Brusco et al. (1998) Eur 3 Immunogen 25:349. Thus, in that particular embodiment, the constant region of the antibody is identical to antibodies found naturally in humans.

BRIEF DESCRIPTION OF THE FIGURES

FIG. 3A: Groups (n=5) of SCID mice were injected with chimeric antibody mixtures: 100 μg IgG1-Betv1/100 μg IgG1-Feld1 (squares), 100 μg IgG4-Betv1/100 μg IgG4-Feld1 (circles), or 100 μg IgG4-Betv1/100 μg IgG4-Feld1+2,000 μg irrelevant recombinant IgG4 (IgG4-EGFR; triangles). Generation of bispecific antibodies was followed in time by assessing the bispecific activity to Bet v 1 and Fel d 1 in plasma. The fraction of bispecific IgG relative to the total IgG-Bet v 1 concentration was expressed as percentage. The arrow with asterisk indicates the bispecific reactivity level expected in mice receiving IgG4-Betv1/IgG4-Feld1 in the presence of excess irrelevant IgG4 (4%), the arrow without asterisk that in mice receiving IgG4-Betv1/IgG4-Feld1 mixture (50%). Error bars represent SEM. FIG. 3B: Monospecific cross-linking activity was tested by assessing cross-linking of radiolabeled Fel d 1 to Fel d 1-coupled Sepharose in mouse plasma. Monospecific reactivity was expressed as the ratio between the amount of radiolabeled Fel d 1 bound by cross-linking and total IgG-Feld1 in order to correct for the clearance of IgG. Error bars represent SEM.

Exchange of IgG4 and IgG1 was evaluated by incubating chimeric IgG mixtures in whole blood, blood cells, plasma and serum for 24 h at 37° C., after which bispecific activity in the heterologous cross-linking assay (Fel d 1-Bet v 1) was measured. Blood was obtained from two donors: donor A (black bars) and donor B (grey bars). Bispecific activities were determined in mixtures supplemented with chimeric IgG4 (FIG. 5A), chimeric IgG1 (FIG. 5B) or without the addition of IgG (FIG. 5C). All presented data were measured after 24 h of incubation at 37° C.

Figure 6:
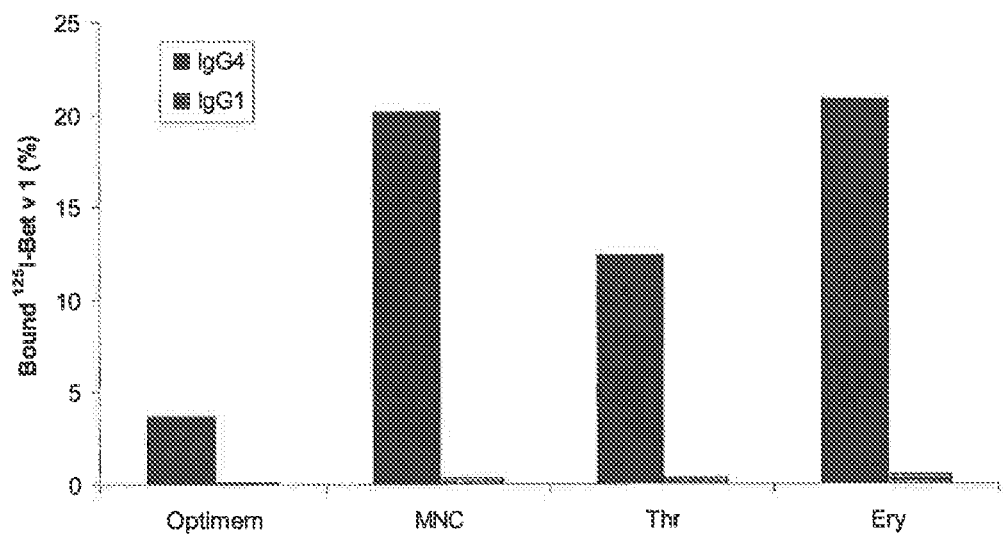

FIG. 6. Fab arm exchange of IgG by human blood cells

Fab arm exchange of IgG4 (black bars) and IgG1 (grey bars) was evaluated by incubating chimeric IgG mixtures with mononuclear cells (MNC), thrombocytes (Thr) and erythrocytes (Ery) for 48 h at 37° C., after which bispecific activity in the heterologous cross-linking assay (Fel d 1-Bet v 1) was measured. As a control, the antibody mixtures were also incubated in serum free culture medium (SFC). Bispecificity is expressed as percentage $^{125}$I-Bet v 1 bound relative to amount added.

Figure 7:
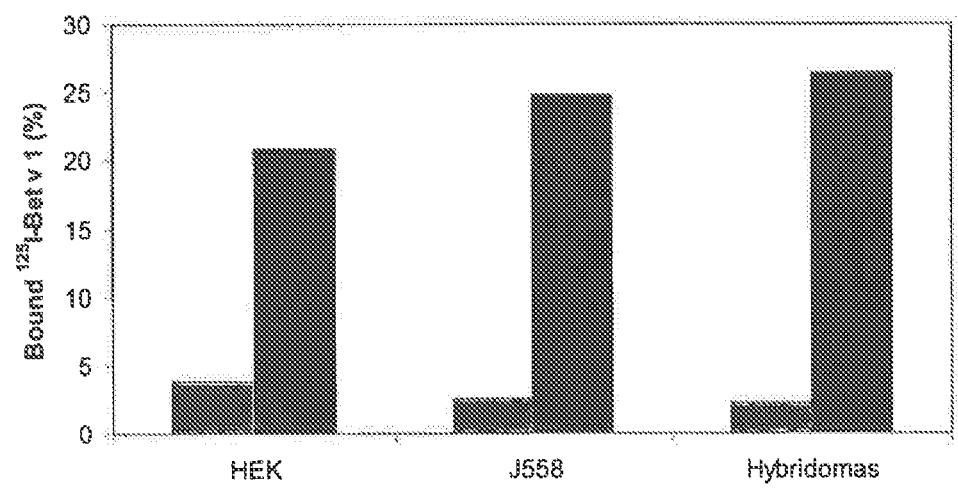

FIG. 7. Fab arm exchange of IgG4 by HEK and murine cell lines Fab arm exchange of IgG4 half molecules was evaluated by incubating a chimeric IgG4 mixture with HEK cells, murine B cells (J558) or hybridoma cells at 37° C. Bispecific activity in the heterologous cross-linking assay (Fel d 1-Bet v 1) was measured in samples of 1 μl drawn at t=0 h (gray bars) and at t=24 h (black bars). Bispecificity is expressed as percentage $^{125}$I-Bet v 1 bound relative to amount added.

Figure 8:
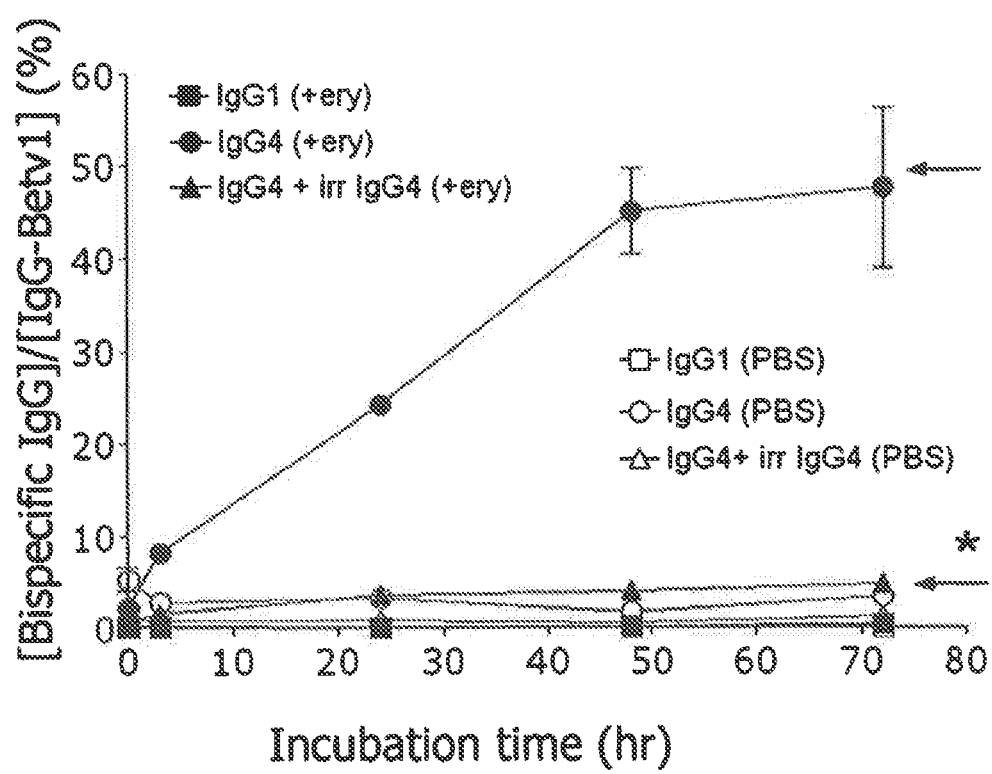

FIG. 8. Erythrocyte-mediated Fab arm exchange of IgG4 Incubation of IgG4-Betv1/IgG4-Feld1 mixtures with freshly purified erythrocytes (ery, closed symbols) resulted in the generation of bispecific antibodies, whereas no bispecificity was observed for the mixture of the IgG1 isotypes. As control, antibody mixtures were incubated in PBS without erythrocytes (open symbols). The arrow indicates the maximal expected percentage of bispecific IgG (50%). Error bars represent range of duplicate measurements.

Figure 9A:
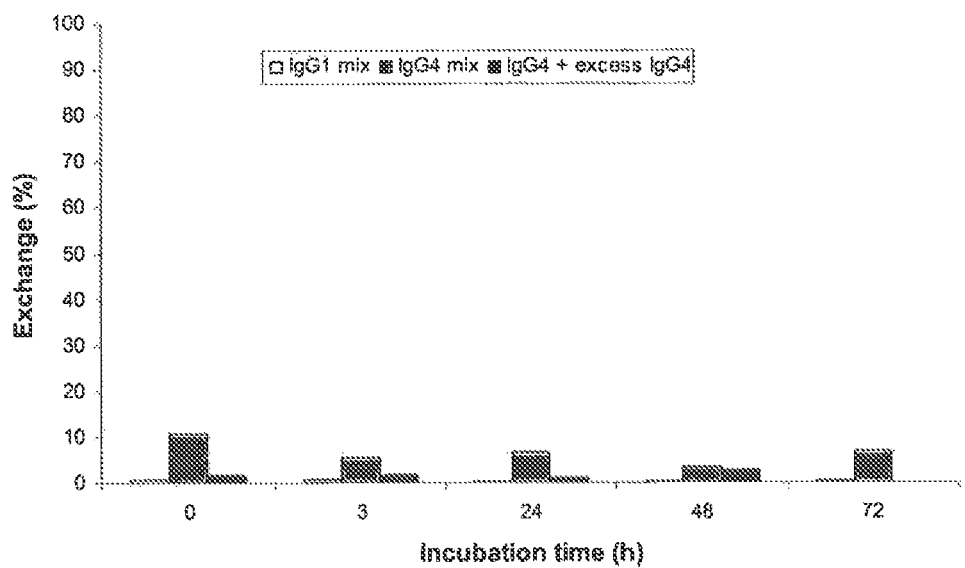
Figure 9B:
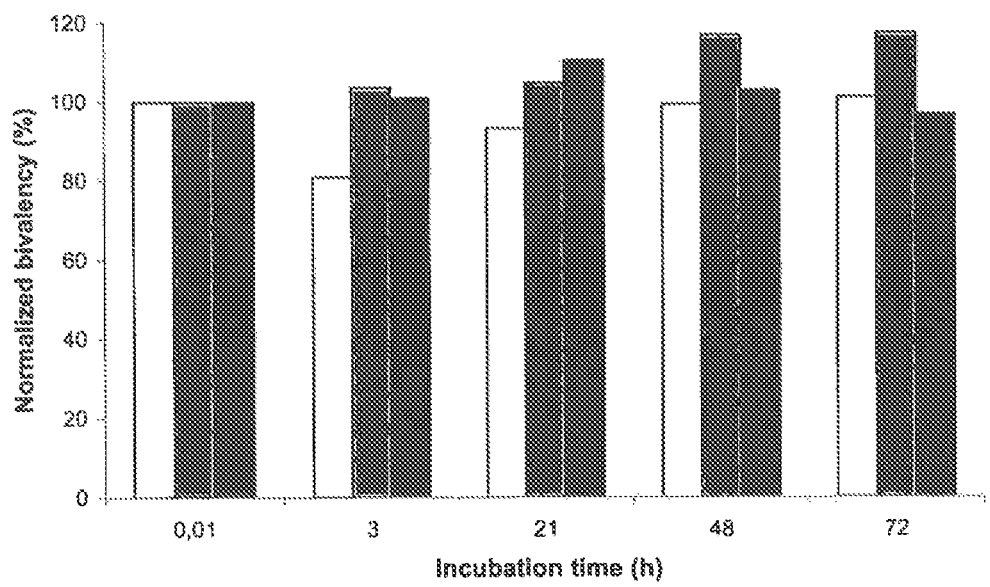

FIGS. 9A and 9B. Absence of Fab arm exchange of IgG4 in PBS

Fab arm exchange in PBS of IgG1 (white bars), IgG4 (grey bars) and IgG4 in the presence of excess irrelevant IgG4 (black bars) was evaluated by measuring bispecific activity, bivalency and antigen binding. FIG. 9A: The exchange of IgG Fab arms was calculated from the concentration of bispecific IgG (as determined in the heterologous cross-linking assay) and the maximal expected concentration of bispecific IgG if the exchange of IgG half molecules is random and complete. The Fab arm exchange is expressed as percentage of the maximal exchange, being 100%. FIG. 9B: Fel d 1 bivalency in time is depicted, which was measured in the homologous cross-linking assay. The concentration of bivalent IgG was normalized by setting the concentration of bivalent IgG at t=0 at 100%.

Figure 10:
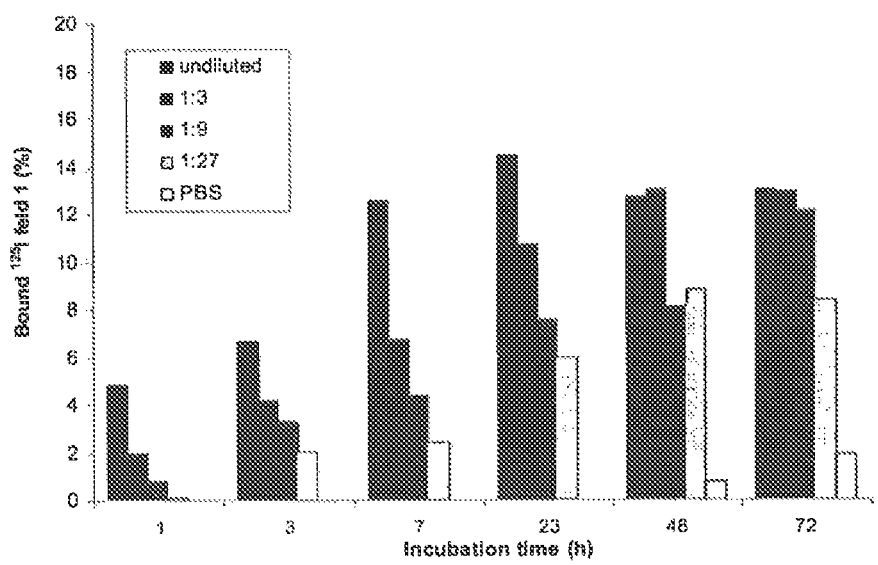

FIG. 10. Fab arm exchange of IgG4 by erythrocyte lysate

Fab arm exchange of IgG4 was evaluated by incubating a chimeric IgG4 mixture in lysate from erythrocytes at 37° C. IgG4 was incubated with increasing dilutions of lysate. Bispecific activity in the heterologous cross-linking assay (Bet v 1-Fel d 1) was measured in samples drawn at indicated time points. Bispecificity is expressed as percentage $^{125}$I-Bet v 1 bound relative to amount added.

Figure 11:
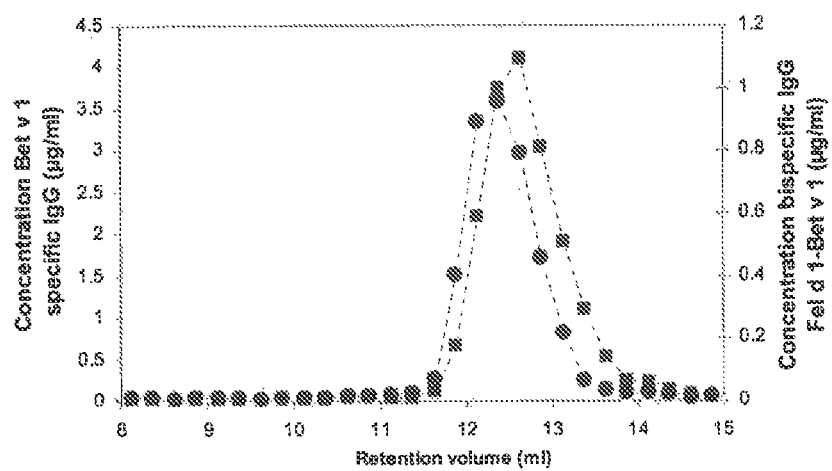

FIG. 11. SEC analysis of bispecific activity induced by erythrocyte lysate

IgG4 was incubated with freshly prepared erythrocyte lysate at 37° C. for 24 h and subsequently fractionated on a Superdex200 column, which was run at 0.5 ml/min on an ÄKTA HPLC unit (Amersham Biosciences, Uppsala, Sweden). In the fractions the concentration of Bet v 1 specific IgG (■) was measured in the antigen binding test and the concentration of bispecific IgG Fel d 1-Bet v 1 (●) was determined in the Bet v 1-Fel d 1 cross-linking assay. Calibration of this column has revealed that monomeric, dimeric and aggregated IgG elute at 12.1, 10.3 and 8.3 ml, respectively (data not shown).

Figure 12:
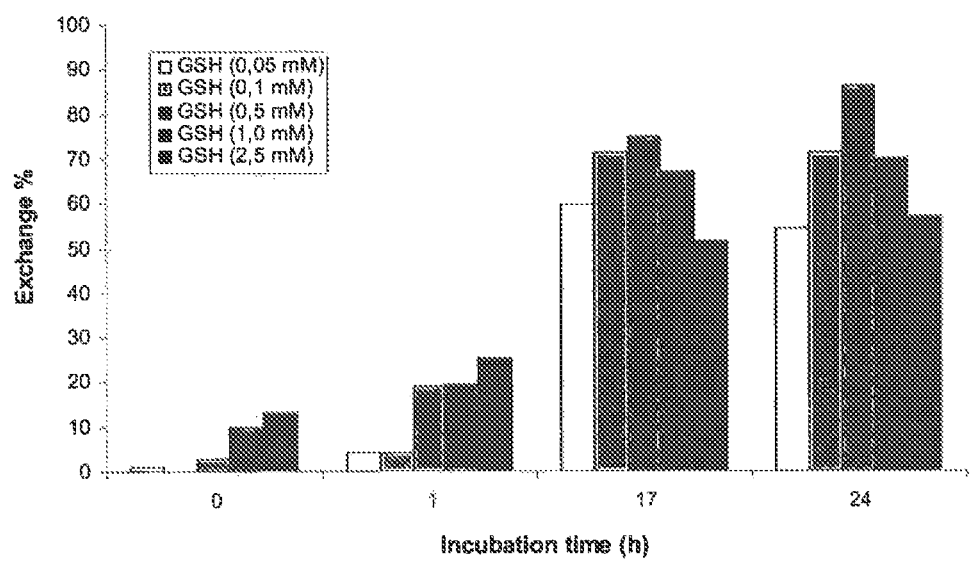

FIG. 12. GSH mediated Fab arm exchange of IgG4

GSH mediated exchange of IgG4 Fab arms was evaluated by incubating IgG4 in the presence of increasing concentrations of GSH in PBS/Azide. At indicated time points samples were drawn in which antigen binding and bispecific activity was measured. The exchange of IgG4 Fab arms was calculated from the measured concentration of bispecific IgG (as determined in the heterologous cross-linking assay) and the maximal expected concentration of bispecific IgG4 if the exchange of IgG4 Fab arms is random and complete. The exchange was expressed as percentage of the maximal exchange, set at 100%.

Figure 13:
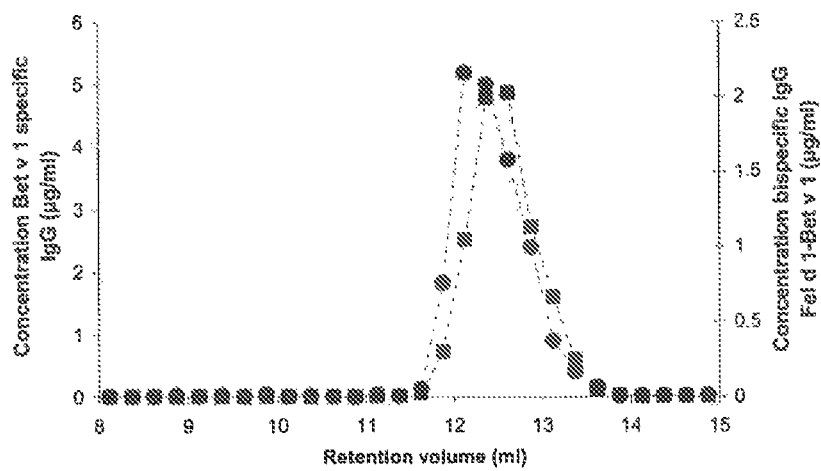

FIG. 13. SEC of GSH mediated Fab arm exchange of IgG4 half molecules

IgG4 was incubated with GSH (0.5 mM) and subsequently fractionated on a Superdex200 column, which was run at 0.5 ml/min on an ÄKTA HPLC unit (Amersham Biosciences, Uppsala, Sweden). In the fractions the concentration of Bet v 1 specific IgG (■) was measured in the antigen binding test and the concentration of bispecific IgG Fel d 1-Bet v 1 (●) was determined in the Bet v 1-Fel d 1 cross-linking assay. Calibration of this column has revealed that monomeric, dimeric and aggregated IgG elute at 12.1, 10.3 and 8.3 ml, respectively (data not shown).

Figure 14:
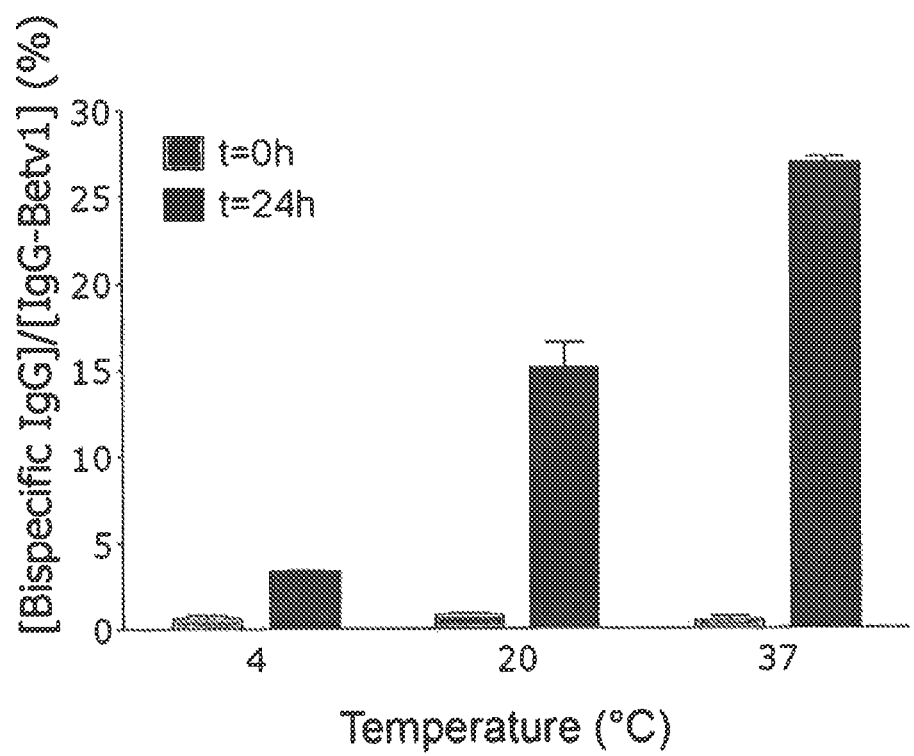

FIG. 14. Temperature dependence of GSH mediated Fab arm exchange of IgG4. IgG4-Betv1 and IgG4-Feld1 mixtures were incubated in PBS with GSH at indicated temperatures. At t=0 h (gray bars) and t=24 h (black bars) concentrations of bispecific IgG4 were assessed. From these data the fraction of bispecific IgG relative to the IgG4 Betv1 concentration was calculated and expressed as percentage. Error bars represent range of duplicate measurements.

Figure 15:
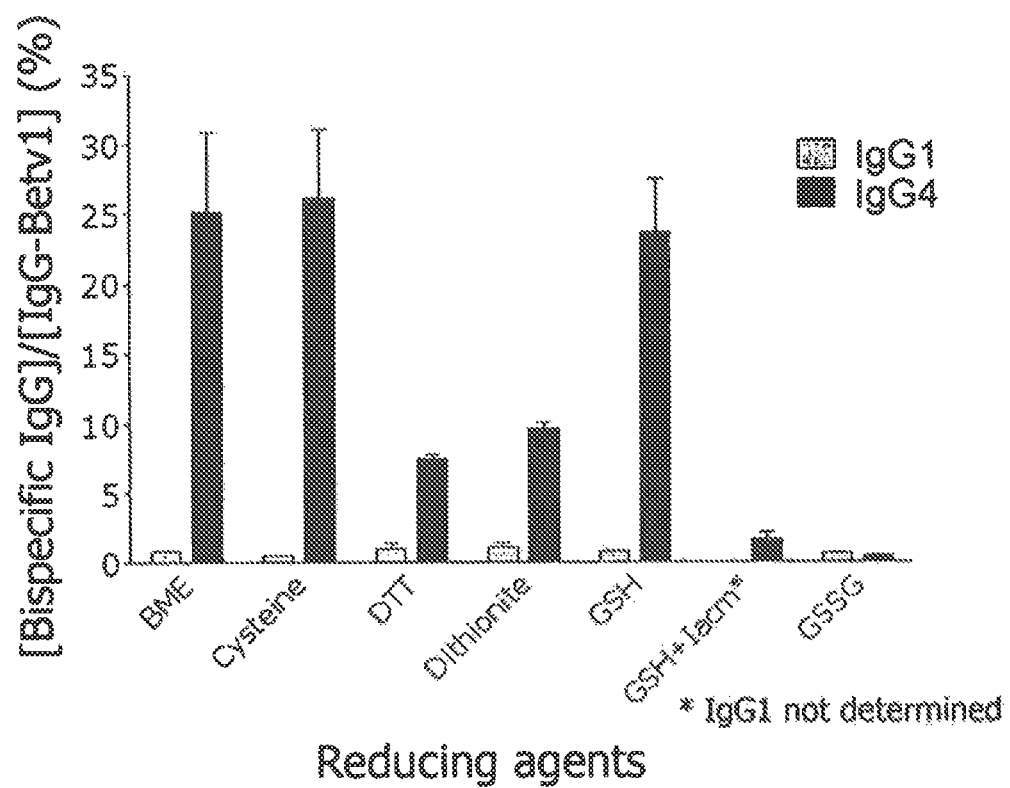

FIG. 15. IgG4 Fab arm exchange mediated by a panel of reducing agents. IgG4-Betv1 and IgG4-Feld1 in PBS were incubated in the presence of different agents (all reducing, except GSSG) for 24 h at 37° C. The concentration of Bet v 1 specific IgG was measured in the antigen binding assay and the concentration of bispecific IgG was measured in the heterologous cross-linking assay (Fel d 1-Bet v 1). The percentage of bispecific IgG relative to the IgG-Betv1 concentration was calculated. Standard error bars represent SEM calculated from three measurements.

FIGS. 16A-F. Fab arm exchange of fully human IgG4 antibodies using GSH

Figure 16A:
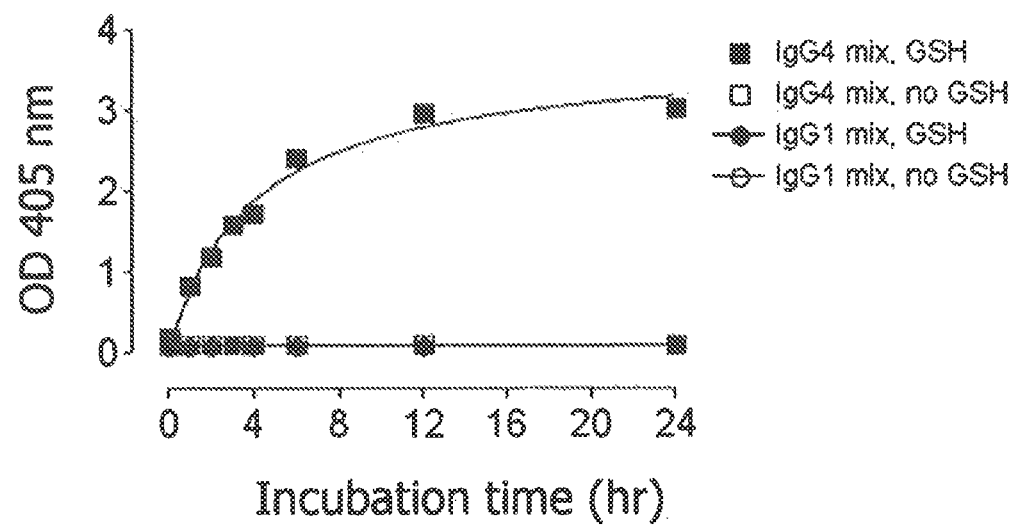

FIG. 16A: IgG4-CD20/IgG4-EGFr or IgG1-CD20/IgG1-EGFr mixtures were incubated at 37° C. with or without 0.5 mM GSH. Samples were taken at indicated time points. The formation of bispecific antibodies was measured in a sandwich ELISA. Y-axis indicates the optical density at 405 nm as a measurement of the formation of bispecific CD20/EGFR antibodies.

Figure 16B:
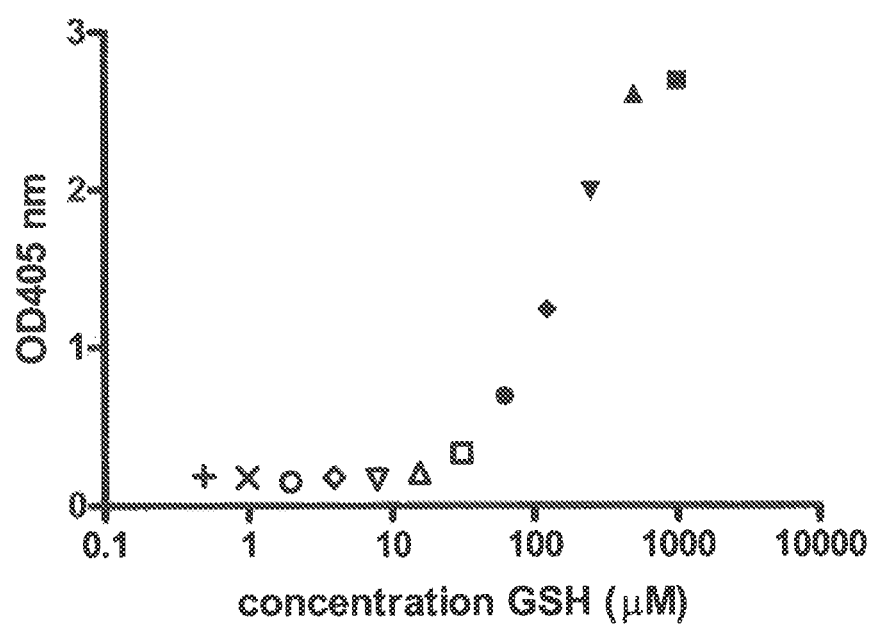

FIG. 16B: GSH-dose dependent Fab arm exchange of IgG4. A mixture of IgG4-CD20 and IgG4-EGFr was incubated for 24 h at 37° C. with concentrations of GSH as indicated. The formation of bispecific antibodies was measured in a sandwich ELISA. The optical density at 405 nm is plotted on the Y-axis as a measurement of the formation of bispecific CD20/EGFR antibodies.

Figure 16C:
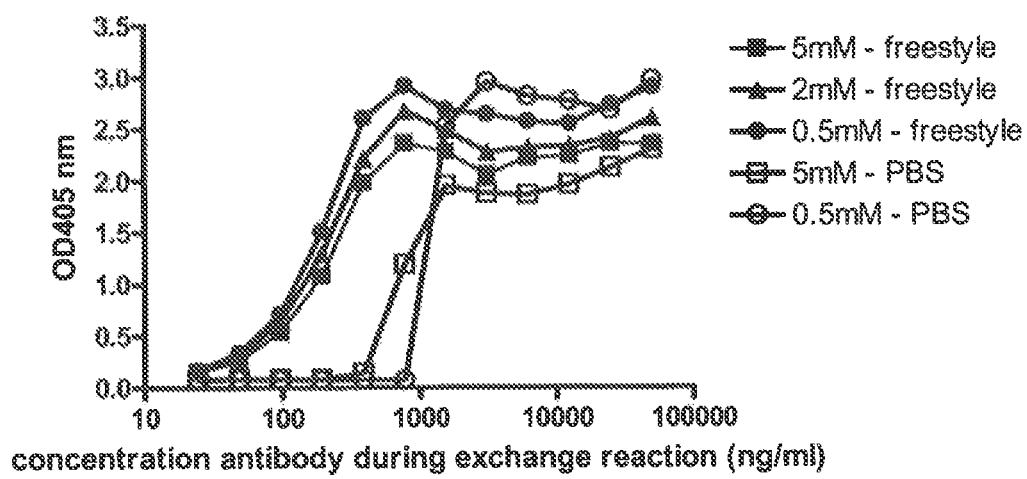

FIG. 16C: GSH-mediated exchange of IgG4 Fab arms is influenced by the components used in the reaction, and occurs in culture medium (Freestyle 293) at lower GSH concentrations.

Figure 16D:
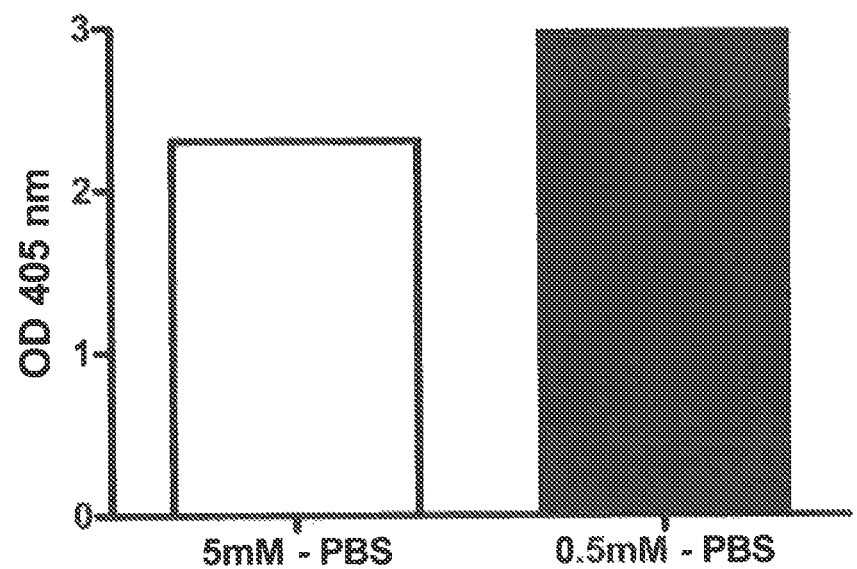

FIG. 16D: GSH-mediated Fab arm exchange of IgG4 is higher at 0.5 mM GSH than at 5 mM GSH.

Figure 16E:
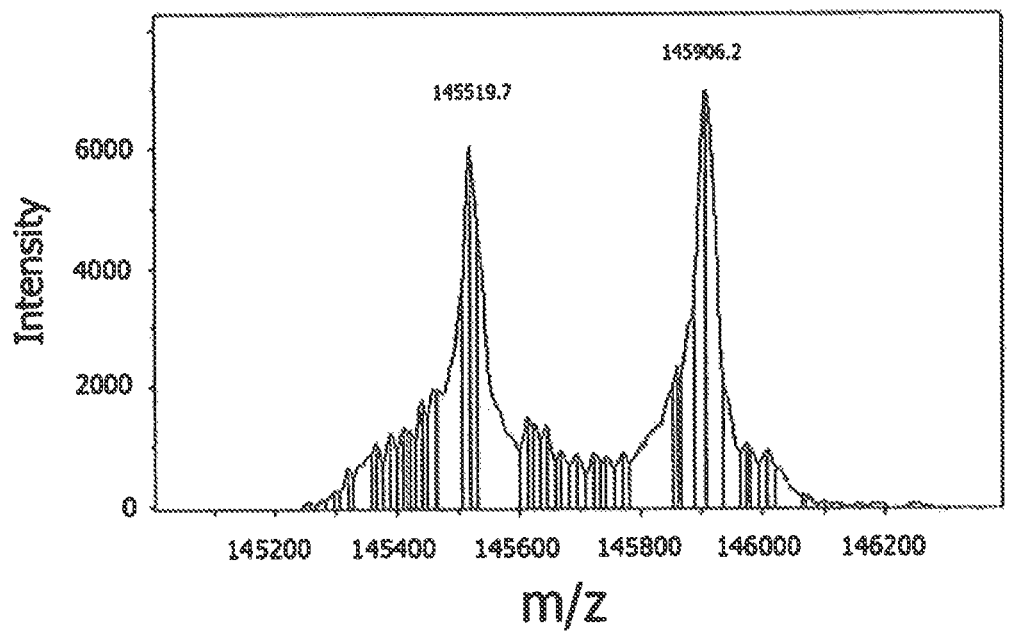
Figure 16F:
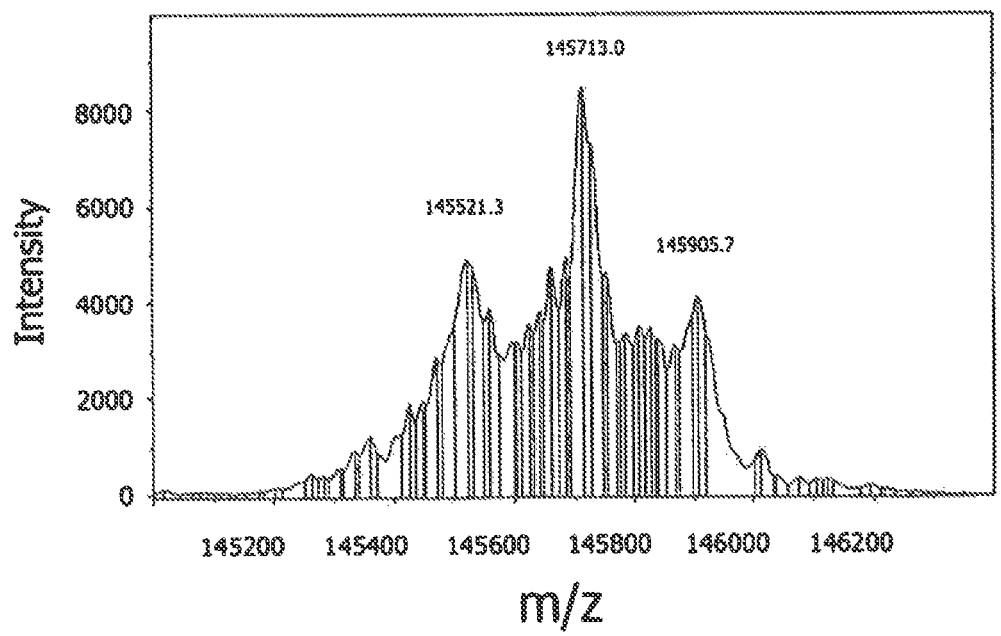

FIGS. 16E-F: Detection of Fab arm exchange between IgG4-EGFR and IgG4-CD20 by ESI-TOF mass spectrometry. An IgG4 mixture was incubated for 24 hours in the absence (FIG. 16E) or presence (FIG. 16F) of 0.5 mM GSH, after which the antibodies were deglycosylated with PNGase F and the molecular weights of the resulting antibodies were determined by ESI-TOF mass spectrometry. Shown are the deconvoluted ESI-TOF spectra. Data are representative of 2 experiments.

Figure 17:
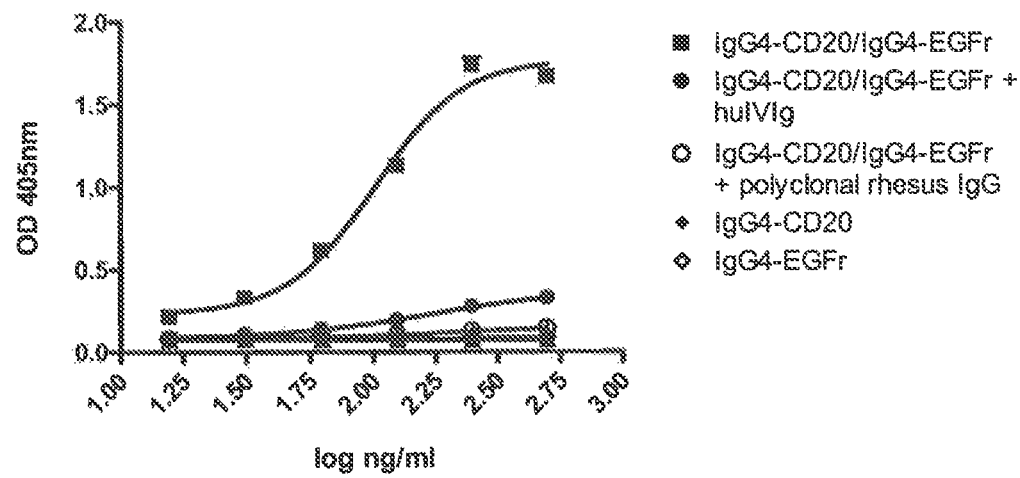

FIG. 17. Rhesus monkey IVIg participates in Fab arm exchange of recombinant human IgG4 antibodies. Mixtures of two recombinant human IgG4 antibodies (IgG4-CD20 and IgG4-EGFr) were incubated with GSH for 24 h at 37° C., in the presence or absence of rhesus monkey or human IVIg. The formation of bispecific antibodies through Fab arm exchange was measured in a sandwich ELISA.

Figure 18:
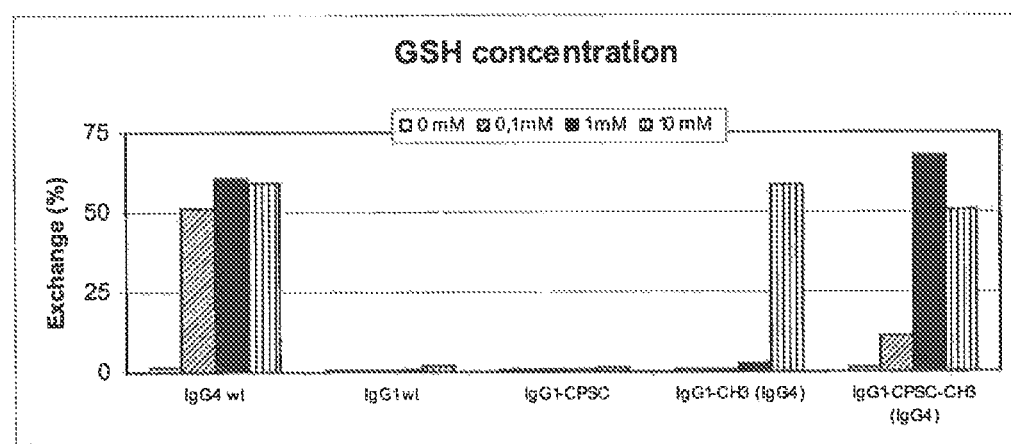

FIG. 18. GSH mediated Fab arm exchange of IgG1 mutants

The effect of GSH concentration on the Fab arm exchange from different IgG1 mutants was tested using 0, 0.1, 1 and 10 mM GSH. All references to CPSC in FIG. 18 refer to SEQ ID NO:51. Fab arm exchange was tested using the following mixtures:

IgG4 anti-feld1 wt with IgG4 anti-betv1 wt (indicated as IgG4 wt in FIG. 18)
IgG1 anti-feld1 wt with IgG4 anti-betv1 wt (indicated as IgG1 wt)
IgG1 anti-feld1 CPSC with IgG1 anti-betv1 CPSC (indicated as IgG1-CPSC)
IgG1 anti-feld1 CH3(IgG4) with IgG1 anti-betv1 CH3 (IgG4) (indicated as IgG1-CH3 (IgG4))
IgG1 anti-feld1 CPSC/CH3(IgG4) with anti-betv1 IgG1 CPSC/CH3(IgG4) (indicated as IgG1-CPSC-CH3 (IgG4))

Figure 19:
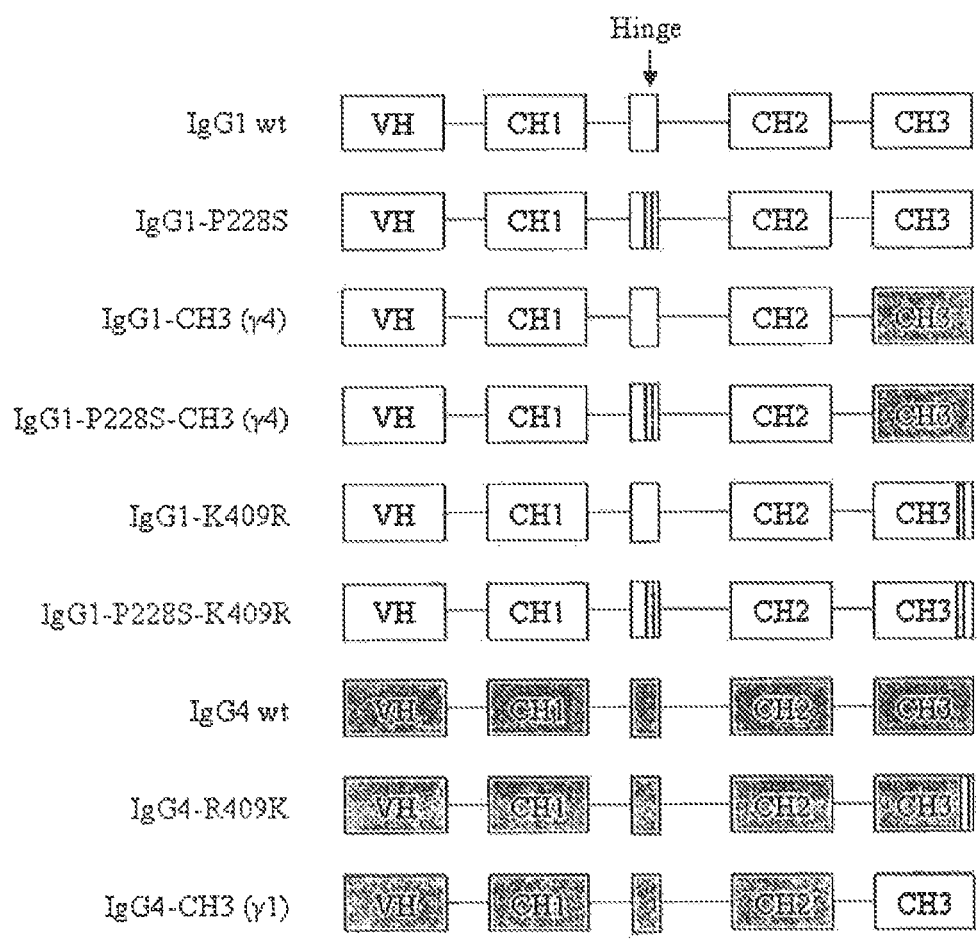

FIG. 19. Schematic representation of constructs for IgG1 and IgG4 containing mutations in the core hinge and/or CH3 domain.

Figure 20:
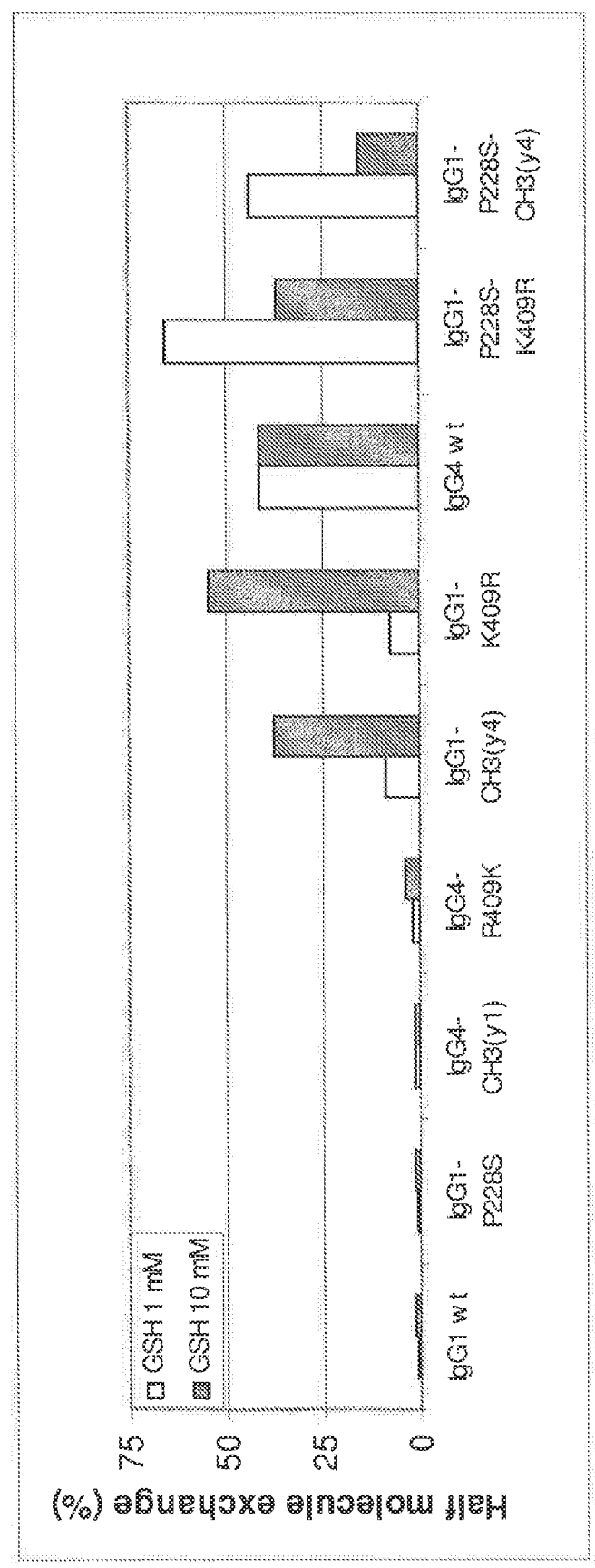

FIG. 20. Fab arm exchange of IgG1 and IgG4 hinge region or CH3 domain mutants.

Figure 21:
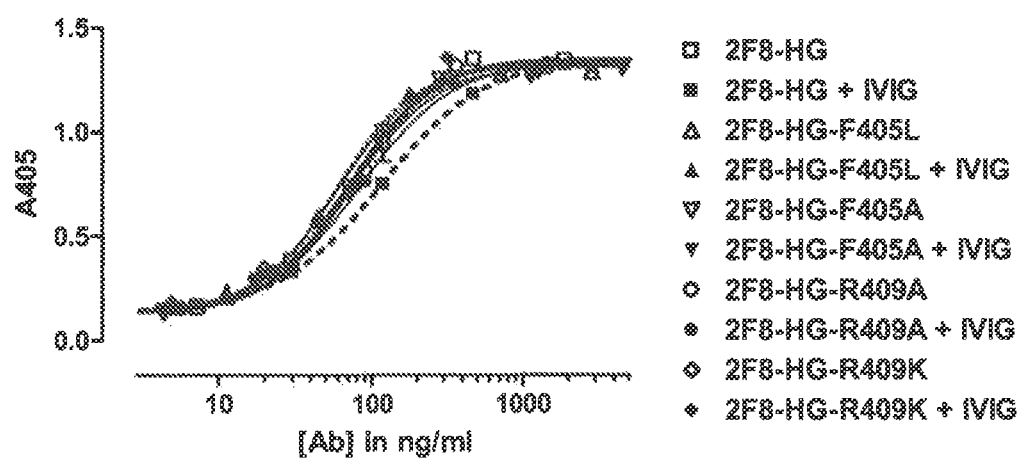

FIG. 21. Binding of hingeless IgG4 antibody 2F8-HG and CH3 mutants 2F8-HG-F405L, 2F8-HG-F405A, 2F8-HG- R409A and 2F8-HG-R409K to EGFr. Binding was tested in an EGFR ELISA in the presence and absence of polyclonal human IgG (IVIG).

Figure 22:
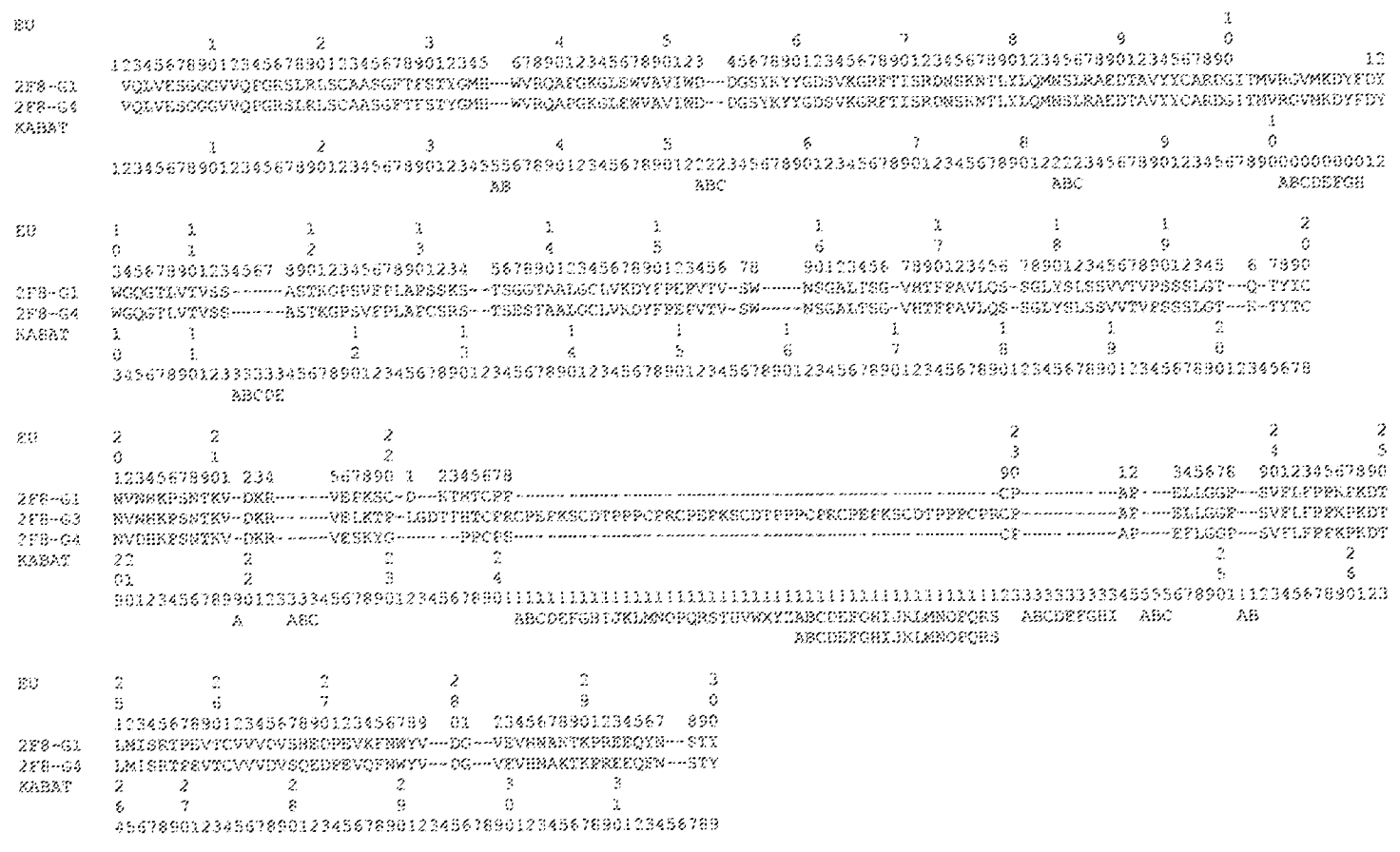

FIG. 22. Sequence alignment of anti-EGFr antibody 2F8 in a IgG1, IgG4 and (partial) IgG3 backbone. Amino acid numbering according to Kabat and according to the EU-index are depicted (both described in Kabat et al., Sequences of Proteins of Immunological Interest, 5th Ed. Public Health Service, National Institutes of Health, Bethesda, Md. (1991)).

Figure 23:
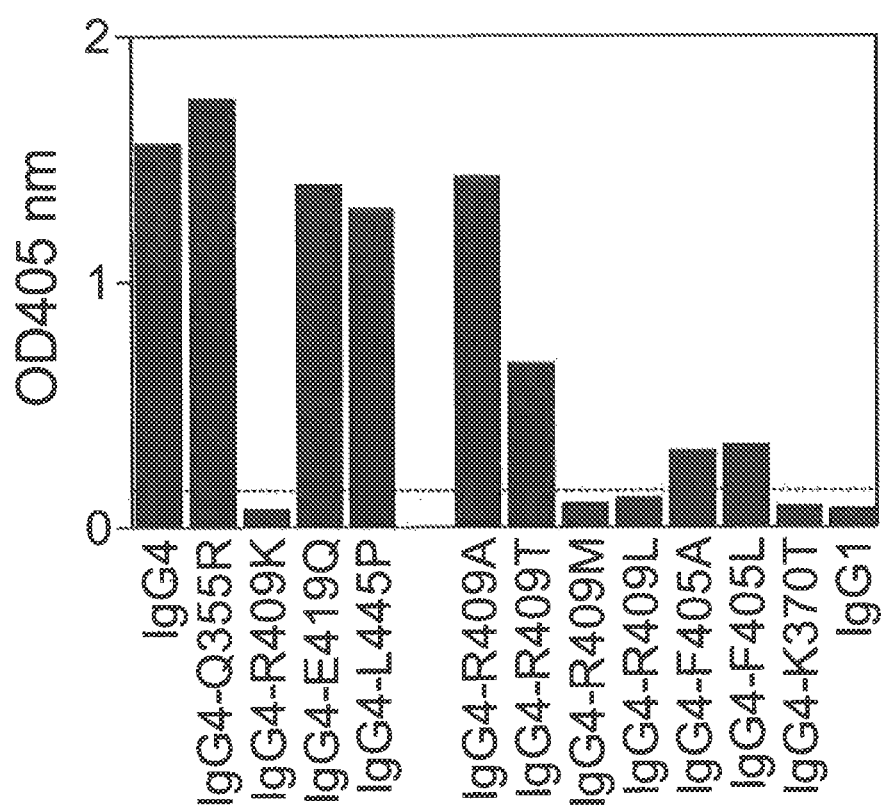

FIG. 23. Fab arm exchange of CH3 domain mutants of human IgG4 antibodies. Mixtures of two recombinant human IgG4 antibodies (IgG4-CD20 and IgG4-EGFr) and CH3 domain mutants thereof were incubated with 0.5 mM GSH for 24 h at 37° C. The formation of bispecific antibodies through Fab arm exchange was measured in a sandwich ELISA.

Figure 24:
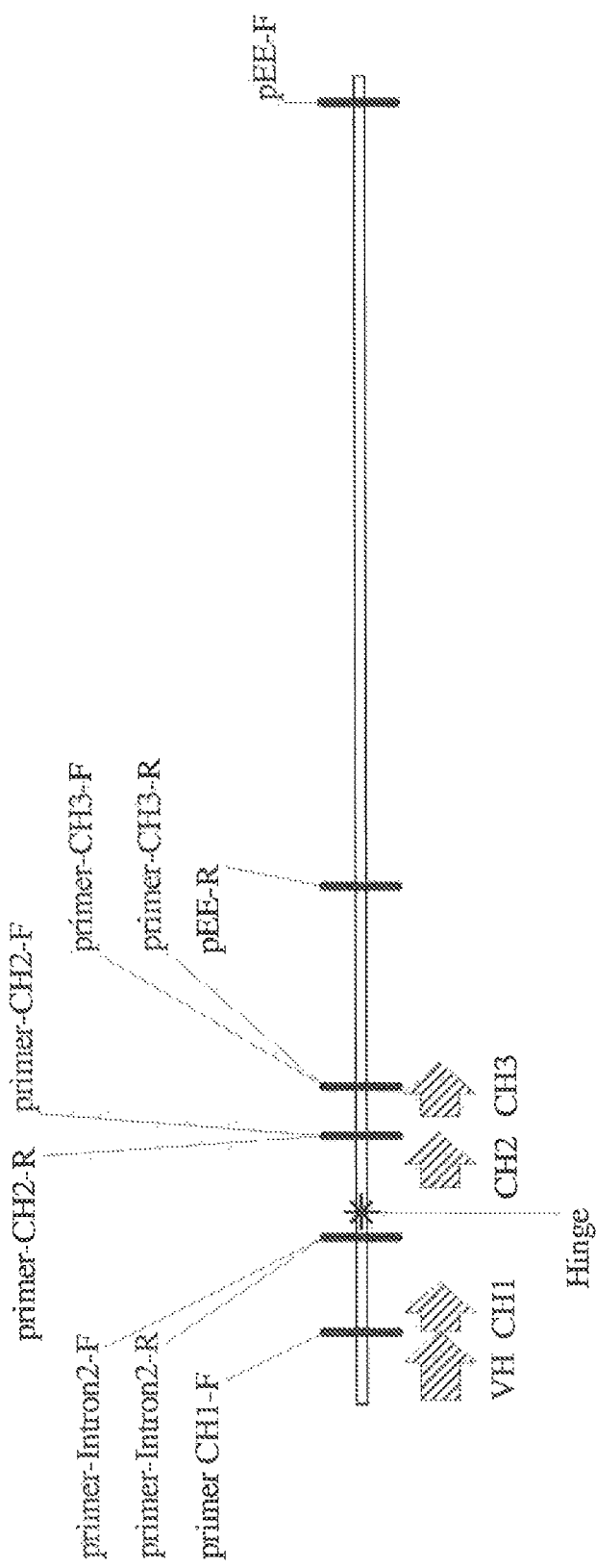

FIG. 24. Shows the location of primers used for the preparation of DNA constructs.

DETAILED DESCRIPTION OF THE INVENTION

Definitions

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$ or VH) and a heavy chain constant region. The heavy chain constant region typically is comprised of three domains, $C_H1$, $C_H2$, and $C_H3$. Each light chain typically is comprised of a light chain variable region (abbreviated herein as $V_L$ or VL) and a light chain constant region. The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk 3. Mol. Biol. 196, 901-917 (1987)).

Often, the numbering of amino acid residues is performed by the method described in Kabat et al., Sequences of Proteins of Immunological Interest, 5th Ed. Public Health Service, National Institutes of Health, Bethesda, Md. (1991). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of $V_H$ CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

Alternatively, the numbering of amino acid residues is performed by the EU-index also described in Kabat et al., Sequences of Proteins of Immunological Interest, 5th Ed. Public Health Service, National Institutes of Health, Bethesda, Md. (1991). This numbering is often used in literature dealing with the Fc part of human immunoglobulin G molecules and is also used throughout this application.

FIG. 22 gives an overview of both numbering methods and shows an alignment of different antibody isotypes based on anti-EGFR antibody 2F8.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an Fc-mediated effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. As indicated above, the term antibody herein, unless otherwise stated or clearly contradicted by context, includes fragments of an antibody that comprise a mutated or wildtype core hinge region and retain the ability to specifically bind to the antigen.

It has been shown that the antigen-binding function of an antibody may be performed by fragments of a full-length antibody. Although such fragments are generally included within the meaning of antibody, they collectively and each independently are unique features of the present invention, exhibiting different biological properties and utility. It also should be understood that the term antibody, unless specified otherwise, also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "chimeric antibody" refers to an antibody that contains one or more regions from one antibody and one or more regions from one or more other antibodies. The term "chimeric antibody" includes divalent and polyvalent antibodies. Chimeric antibodies are produced by recombinant processes well known in the art (see for instance Cabilly et al., PNAS USA 81, 3273-3277 (1984), Morrison et al., PNAS USA 81, 6851-6855 (1984), Boulianne et al., Nature 312, 643-646 (1984), EP125023, Neuberger et al., Nature 314, 268-270 (1985), EP171496, EP173494, WO86/01533, EP184187, Sahagan et al., 3. Immunol. 137, 1066-1074 (1986), WO87/02671, Liu et al., PNAS USA 84, 3439-3443 (1987), Sun et al., PNAS USA 84, 214-218 (1987), Better et al., Science 240, 1041-1043 (1988) and Harlow et al., Antibodies: A Laboratory Manual, Cold Spring Harbor Laboratory Press, Cold Spring Harbor, N.Y., (1988)).

A "humanized antibody" is an antibody that is derived from a non-human species, in which certain amino acids in the framework and constant domains of the heavy and light chains have been mutated so as to avoid or abrogate an immune response in humans. Humanized forms of non-human (for instance murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. A humanized antibody typically also will comprise at least a portion of an immunoglobulin constant region (Fc), typically that of a human immunoglobulin. For further details, see Jones et al., Nature 321, 522-525 (1986), Riechmann et al., Nature 332, 323-329 (1988) and Presta, Curr. Op. Struct. Biol. 2, 593-596 (1992).

An "isolated antibody" as used herein, is intended to refer to an antibody which is substantially free of other antibodies having different antigenic specificities. An isolated antibody that specifically binds to an epitope, isoform or variant of a particular human target antigen may, however, have cross-reactivity to other related antigens, for instance from other species (such as species homologs). Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal nonhuman animal, such as a transgenic mouse, having a genome comprising a human heavy chain transgene and a light chain transgene, fused to an immortalized cell.

As used herein, the term "binding" in the context of the binding of an antibody to a predetermined antigen typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte, and binds to the predetermined antigen with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold.

The term "$k_d$" (sec$^{-1}$), as used herein, refers to the dissociation rate constant of a particular antibody-antigen interaction. Said value is also referred to as the $k_{off}$ value.

The term "$k_a$" (M$^{-1}$×sec$^{-1}$), as used herein, refers to the association rate constant of a particular antibody-antigen interaction.

The term "$K_D$" (M), as used herein, refers to the dissociation equilibrium constant of a particular antibody-antigen interaction.

The term "$K_A$" (M$^{-1}$), as used herein, refers to the association equilibrium constant of a particular antibody-antigen interaction and is obtained by dividing the $k_a$ by the $k_d$.

As used herein, "isotype" refers to the immunoglobulin (sub)class, for instance IgG1, IgG2, IgG3, IgG4, IgD, IgA, IgE, or IgM, that is encoded by heavy chain constant region genes.

As used herein, a human antibody is "derived from" a particular germline sequence if the antibody is obtained from a system using human immunoglobulin sequences, for instance by immunizing a transgenic mouse carrying human immunoglobulin genes or by screening a human immunoglobulin gene library, and wherein the selected human antibody is at least 90%, such as at least 95%, for instance at least 96%, such as at least 97%, for instance at least 98%, or such as at least 99% identical in amino acid sequence to the amino acid sequence encoded by the germline immunoglobulin gene. Typically, outside the heavy chain CDR3, a human antibody derived from a particular human germline sequence will display no more than 20 amino acid differences, e.g. no more than 10 amino acid differences, such as no more than 5, for instance no more than 4, 3, 2, or 1 amino acid difference from the amino acid sequence encoded by the germline immunoglobulin gene.

The term "bispecific antibody" is intended to include any antibody, which has two different binding specificities, i.e. the antibody binds two different epitopes, which may be located on the same target antigen or, more commonly, on different target antigens.

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, polymorphonuclear cells, such as neutrophils, granulocytes, mast cells, and basophils. Some effector cells express specific Fc receptors and carry out specific immune functions. In some embodiments, an effector cell is capable of inducing antibody-dependent cellular cytotoxicity (ADCC), such as a natural killer cell, capable of inducing ADCC. For example, monocytes, macrophages, which express FcR are involved in specific killing of target cells and presenting antigens to other components of the immune system, or binding to cells that present antigens. In some embodiments, an effector cell may phagocytose a target antigen or target cell. The expression of a particular FcR on an effector cell may be regulated by humoral factors such as cytokines. For example, expression of FcγRI has been found to be up-regulated by interferon γ (IFN-γ) and/or G-CSF. This enhanced expression increases the cytotoxic activity of FcγRI-bearing cells against targets. An effector cell can phagocytose or lyse a target antigen or a target cell.

"Treatment" refers to the administration of an effective amount of a therapeutically active compound of the present invention with the purpose of easing, ameliorating, arresting or eradicating (curing) symptoms or disease states.

An "effective amount" refers to an amount effective, at dosages and for periods of time necessary, to achieve a desired therapeutic result. A therapeutically effective amount of an antibody may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

The terms "half-molecule exchange" and "Fab arm exchange" are used interchangeably herein and refer to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules) while their Fc domain structure remains unchanged. As shown herein, Fab arm exchange occurs naturally in vivo and can be induced in vitro by purified blood cells or reducing agents such as reduced glutathione.

Further Aspects and Embodiments of the Invention

As described above, in a first main aspect, the invention relates to a stabilized IgG4 antibody for use as a medicament, comprising a heavy chain and a light chain, wherein said heavy chain comprises a human IgG4 constant region having a substitution of the Arg residue at position 409, the Phe residue at position 405 or the Lys residue at position 370, wherein said antibody optionally comprises one or more further substitutions, deletions and/or insertions, with the proviso that if the antibody has a residue selected from the group consisting of: Lys, Ala, Thr, Met and Leu at the position corresponding to 409, then the antibody does not comprise a Cys-Pro-Pro-Cys sequence (SEQ ID NO:50) in the hinge region.

In one embodiment, the antibody, comprises a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions, but does not comprise a Cys-Pro-Pro-Cys sequence (SEQ ID NO:50) in the hinge region.

The numbers 405 and 409 refer to the Phe and Lys residues at positions 405 and 409, respectively, using the numbering according to the EU index, see also Example 38 and FIG. 22.

In a further main aspect, the invention relates to an isolated stabilized IgG4 antibody, comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises further substitutions, deletions and/or insertions, but does not comprise a Cys-Pro-Pro-Cys sequence (SEQ ID NO:50) in the hinge region and does not comprise both a Lys at position 409 and a Leu at position 309.

In one embodiment, said antibody comprises a Lys, Ala, Thr, Met or Leu residue at the position corresponding to 409.

In another embodiment, said antibody comprises a Lys, Thr, Met or Leu residue at the position corresponding to 409.

In a further embodiment, said antibody comprises a Lys, Met or Leu residue at the position corresponding to 409.

In a yet other embodiment, the CH3 region of the antibody has been replaced by the CH3 region of human IgG1, of human IgG2 or of human IgG3.

In a further embodiment of the stabilized IgG4 antibody of the invention, the antibody has a residue which is has a lower mass (in Da) than Phe at the position corresponding to 405.

In a further embodiment, said antibody comprises an Ala, Val, Gly, Ile or Leu residue at the position corresponding to 405.

In an even further embodiment, said antibody comprises an Ala or Leu residue at the position corresponding to 405.

In a further embodiment of the stabilized IgG4 antibody of the invention, the antibody has a Thr residue at the position corresponding to 370.

In an even further embodiment, the stabilized IgG4 antibody of the invention does not comprise a substitution of the Leu residue at the position corresponding to 235 by a Glu.

However, in another embodiment, said antibody does comprise a substitution of the Leu residue at the position corresponding to 235 by a Glu.

In a further embodiment, the antibody of the invention may have been further modified to even further reduce effector functions.

Accordingly, in one embodiment, the antibody of the invention comprises one or more of the following substitutions: an Ala at position 234, an Ala at position 236, an Ala at position 237, an Ala at position 297, an Ala or Val at position 318, an Ala at position 320, an Ala or Gln at position 322.

In another embodiment, the stabilized IgG4 antibody of the invention does not comprise a Cys-Pro-Pro-Cys sequence (SEQ ID NO:50) in the hinge region.

In one embodiment, the stabilized IgG4 antibody of the invention comprises a CXPC or CPXC sequence in the hinge region, wherein X can be any amino acid except for proline.

In a further embodiment, the antibody of the invention does not comprise a CPRC sequence in the core hinge region and/or does not comprise an extended IgG3-like hinge region, such as the extended hinge region as set forth in FIG. 22 (between positions 228 and 229 in IgG3).

In one embodiment, the stabilized IgG4 antibody of the invention comprises a CPSC sequence (SEQ ID NO:51) in the hinge region.

As explained above, the antibody of the invention may contain further modifications. In one embodiment, the stabilized IgG4 antibody of the invention comprises a constant heavy chain region comprising an amino acid sequence selected from the group consisting of: SEQ ID NO:39, 40 and 41 or a variant of said amino acid sequence having less than 25, such as less than 10, e.g. less than 9, 8, 7, 6, 5, 4, 3, or 2 substitutions, deletions and/or insertions compared to said amino acid sequence.

Typically, the stabilized IgG4 antibody of the invention has a lower ability to activate effector functions as compared to IgG1 and IgG3, Thus, in one embodiment, said antibody is less efficient in mediating CDC and/or ADCC than a corresponding IgG1 or IgG3 antibody having the same variable regions. Assays for measuring CDC or ADCC activity are well known in the art.

In one embodiment, the stabilized IgG4 antibody of the invention comprises a constant heavy chain region comprising the amino acid sequence set forth in SEQ ID NO:40.

In one embodiment of the invention, the stabilized IgG4 antibody is selected from the group consisting of: a human antibody, a humanized antibody and a chimeric antibody.

In one further embodiment, the antibody of the invention comprises a human kappa light chain. In another embodiment, said antibody comprises a human lambda light chain.

Typically, the stabilized IgG4 antibody of the invention is a bivalent antibody, for example an antibody which is bivalent even in the presence of excess of irrelevant antibodies, as explained in Example 38. Furthermore, the stabilized IgG4 antibody of the invention is preferably a full-length antibody, i.e. not a fragment.

Methods for the production of antibodies are well-known in the art. In a preferred embodiment, antibodies of the invention are monoclonal antibodies. Monoclonal antibodies may e.g. be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., 3. Mol. Biol. 222, 581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

Further modifications, such as amino acid substitutions, deletions or insertion as described above, may be performed using standard recombinant DNA techniques well-known in the art.

In one embodiment, the antibody of the invention is a human antibody. Human monoclonal antibodies directed may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice".

The HuMAb mouse contains a human immunoglobulin gene miniloci that encodes unrearranged human heavy (µ and γ) and κ light chain immunoglobulin sequences, together with targeted mutations that inactivate the endogenous µ and κ chain loci (Lonberg, N. et al., Nature 368, 856-859 (1994)). Accordingly, the mice exhibit reduced expression of mouse IgM or K and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., 3. Immunol. 152, 2912-2920 (1994), Taylor, L. et al., International Immunology 6, 579-591 (1994), Fishwild, D. et al., Nature Biotechnology 14, 845-851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7 mice have a JKD disruption in their endogenous light chain (kappa) genes (as described in Chen et al., EMBO 3. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo7 human heavy chain transgene (as described in U.S. Pat. No. 5,770,429).

The HCo12 mice have a JKD disruption in their endogenous light chain (kappa) genes (as described in Chen et al., EMBO 3. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo12 human heavy chain transgene (as described in Example 2 of WO 01/14424).

In the KM mouse strain, the endogenous mouse kappa light chain gene has been homozygously disrupted as described in Chen et al., EMBO 3. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478.

Splenocytes from these transgenic mice may be used to generate hybridomas that secrete human monoclonal antibodies according to well known techniques. Such transgenic non-human animals, non-human animals comprising an operable nucleic acid sequence coding for expression of antibody used in the invention, non-human animals stably transfected with one or more target-encoding nucleic acid sequences, and the like, are additional features of the present invention.

Human monoclonal or polyclonal antibodies to be used in the present invention, or antibodies used in the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. Nos. 5,827,690, 5,756,687, 5,750,172 and 5,741,957.

Further, human or other antibodies to be used in the present invention may be generated through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., 3. Mol. Biol. 227, 381 (1991) (phage display), Vaughan et al., Nature Biotech 14, 309 (1996) (phage display), Hanes and Pluckthun, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russel et al., Nucl. Acids Research 21, 1081-1085 (1993), Hoogenboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized.

In a further main aspect, the invention relates to a method for producing a stabilized IgG4 antibody of the invention, said method comprising expressing a nucleic acid construct encoding said antibody in a host cell and optionally purifying said antibody. In one embodiment of this method, said stabilized IgG4 antibody does not comprise both a Lys at position 409 and a Leu at position 309.

In one embodiment, the antibody of the invention is linked to a compound selected from the group consisting of: a cytotoxic agent; a radioisotope; a prodrug or drug, such as a taxane; a cytokine; and a chemokine. Methods for linking (conjugating) such compounds to an antibody are well-known in the art. References to suitable methods have been given in WO 2004/056847 (Genmab).

In a further main aspect, the invention relates to a pharmaceutical composition comprising a stabilized IgG4 antibody as defined herein above. The pharmaceutical compositions may be formulated with pharmaceutically acceptable carriers or diluents as well as any other known adjuvants and excipients in accordance with conventional techniques, such as those disclosed in Remington: The Science and Practice of Pharmacy, 19th Edition, Gennaro, Ed., Mack Publishing Co., Easton, Pa., 1995.

The pharmaceutically acceptable carriers or diluents as well as any other known adjuvants and excipients should be suitable for the chosen compound of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.) on antigen binding.

A pharmaceutical composition of the present invention may also include diluents, fillers, salts, buffers, detergents (e.g., a nonionic detergent, such as Tween-80), stabilizers, stabilizers (e.g., sugars or protein-free amino acids), preservatives, tissue fixatives, solubilizers, and/or other materials suitable for inclusion in a pharmaceutical composition.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be intravenous, intramuscular, intraperitoneal, by inhalation or subcutaneous. If desired, the effective daily dose of a therapeutic composition may be administered as two, three, four, five, six or more sub-doses administered separately at appropriate intervals throughout the day, optionally, in unit dosage forms.

In one embodiment, a pharmaceutical composition of the present invention is administered parenterally. The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

Stabilized IgG4 antibodies of the invention can be used in the treatment and/or prevention of a number of diseases, and be directed to an antigen selected from a broad variety of suitable target molecules. In one embodiment of the invention, the antibody binds an antigen selected from the group consisting of: erythropoietin, beta-amyloid, thrombopoietin, interferon-alpha (2a and 2b), interferon-beta (1b), interferon-gamma, TNFR I (CD120a), TNFR II (CD120b), IL-1R type 1 (CD121a), IL-1R type 2 (CD121b), IL-2, IL2R (CD25), IL-2R-beta (CD123), IL-3, IL-4, IL-3R (CD123), IL-4R (CD124), IL-5R (CD125), IL-6R-alpha (CD126), -beta (CD130), IL-8, IL-10, IL-11, IL-15, IL-15BP, IL-15R, IL-20, IL-21, TCR variable chain, RANK, RANK-L, CTLA4, CXCR4R, CCR5R, TGF-beta 1, -beta2, -beta3, G-CSF, GM-CSF, MIF-R (CD74), M-CSF-R (CD115), GM-CSFR (CD116), soluble FcRI, sFcRII, sFcRIII, FcRn, Factor VII, Factor VIII, Factor IX, VEGF, VEGFxxxb, alpha-4 integrin, Cd11a, CD18, CD20, CD38, CD25, CD74, FcalphaRI, FcepsilonRI, acetyl choline receptor, fas, fast, TRAIL, hepatitis virus, hepatitis C virus, envelope E2 of hepatitis C virus, tissue factor, a complex of tissue factor and Factor VII, EGFr, CD4, CD28, VLA-1, 2, 3, or 4, LFA-1, MAC-1, 1-selectin, PSGL-1, ICAM-I, P-selectin, periostin, CD33 (Siglec 3), Siglec 8, TNF, CCL1, CCL2, CCL3, CCL4, CCL5, CCL11, CCL13, CCL17, CCL18, CCL20, CCL22, CCL26, CCL27, CX3CL1, LIGHT, EGF, VEGF, TGFalpha, HGF, PDGF, NGF, complement or a related components such as: C1q, C4, C2, C3, C5, C6, C7, C8, C9, MBL, factor B, a Matrix Metallo Protease such as any of MMP1 to MMP28, CD32b, CD200, CD200R, Killer Immunoglobulin-Like Receptors (KIRs), NKG2D and related molecules, leukocyte-associated immunoglobulin-like receptors (LAIRs), ly49, PD-L2, CD26, BST-2, ML-IAP (melanoma inhibitor of apoptosis protein), cathepsin D, CD40, CD40R, CD86, a B cell receptor, CD79, PD-1, and a T cell receptor.

In one embodiment of the invention, the antibody binds an alpha-4 integrin and is for use in the treatment of inflammatory and autoimmune diseases, such as rheumatoid arthritis, multiple sclerosis, inflammatory bowel disease, asthma and sepsis.

In another embodiment of the invention, the antibody binds VLA-1, 2, 3, or 4 and is for use in the treatment of inflammatory and autoimmune diseases, such as rheumatoid arthritis, multiple sclerosis, inflammatory bowel disease, asthma, type-1 diabetes, SLE, psoriasis, atopic dermatitis, COPD and sepsis.

In another embodiment of the invention, the antibody binds a molecule selected from the group consisting of: LFA-1, MAC-1, 1-selectin and PSGL-1 and is for use in the treatment of inflammatory and autoimmune diseases, such as rheumatoid arthritis, multiple sclerosis, inflammatory bowel disease, asthma, type-1 diabetes, SLE, psoriasis, atopic dermatitis, and COPD.

In another embodiment of the invention, the antibody binds a molecule selected from the group consisting of: LFA-1, MAC-1, 1-selectin and PSGL-1 and is for use in the treatment of a disease selected from the group consisting of ischemia-reperfusion injury, cytic fibrosis, osteomyelitis, glomerulonepritis, gout and sepsis.

In another embodiment of the invention, the antibody binds CD18 and is for use in the treatment of inflammatory and autoimmune diseases, such as rheumatoid arthritis, multiple sclerosis, inflammatory bowel disease, asthma, type-1 diabetes, SLE, psoriasis, atopic dermatitis and COPD.

In another embodiment of the invention, the antibody binds Cd11a and is for use in the treatment of inflammatory and autoimmune diseases, such as rheumatoid arthritis, multiple sclerosis, inflammatory bowel disease, asthma, type-1 diabetes, SLE, psoriasis, atopic dermatitis and COPD.

In another embodiment of the invention, the antibody binds ICAM-1 and is for use in the treatment of inflammatory and autoimmune diseases, such as rheumatoid arthritis, multiple sclerosis, inflammatory bowel disease, asthma, type-1 diabetes, SLE, psoriasis, atopic dermatitis and COPD.

In another embodiment of the invention, the antibody binds P-selectin and is for use in the treatment of cardiovascular diseases, post-thrombotic vein wall fibrosis, ischemia reperfusion injury, inflammatory diseases or sepsis.

In another embodiment of the invention, the antibody binds periostin and is for use in the treatment of malignant diseases and/or metastising diseases, such as ovary cancer, endometrial cancer, NSCLC, glioblastoma, brain-related tumors, breast cancer, OSCC, colon cancer, pancreatic cancer, HNSCC, kidney cancer, thymoma, lung cancer, skin cancer, larynx cancer, liver cancer, parotid tumors, gastric cancer, esophagus cancer, prostate cancer, bladder cancer and cancer of the testis.

In another embodiment of the invention, the antibody binds CD33 (Siglec 3), is optionally coupled to a toxin, cytotoxic or cytostatic drug, and is for use in the treatment of tumors expressing CD33 or acute myeloid leukemia.

In another embodiment of the invention, the antibody binds Siglec 8 and is for use in the treatment of: asthma, inflammatory or autoimmune diseases, such as rheumatoid arthritis, multiple sclerosis, inflammatory bowel disease, asthma, type-1 diabetes, SLE, psoriasis, atopic dermatitis and COPD.

In another embodiment of the invention, the antibody binds nucleolin and is for use in the treatment of malignant diseases and/or metastising diseases, such as ovary cancer, cervical cancer, endometrial cancer, NSCLC, glioblastoma, brain-related tumors, breast cancer, OSCC, colon cancer, pancreatic cancer, HNSCC, kidney cancer, thymoma, lung cancer, skin cancer, larynx cancer, liver cancer, parotid tumors, gastric cancer, oesophagus cancer, prostate cancer, bladder cancer, cancer of the testis and lymphomas.

In another embodiment of the invention, the antibody binds TNF and is for use in the treatment of: inflammatory and autoimmune diseases, such as rheumatoid arthritis, multiple sclerosis, inflammatory bowel disease, asthma, type-1 diabetes, SLE, psoriasis, atopic dermatitis, COPD and sepsis.

In another embodiment of the invention, the antibody binds CCL1, CCL2, CCL3, CCL4, CCL5, CCL11, CCL13, CCL17, CCL18, CCL20, CCL22, CCL26, CCL27 or CX3CL1 and is for use in the treatment of: atopic dermatitis, inflammatory and autoimmune diseases, such as rheumatoid arthritis, multiple sclerosis, inflammatory bowel disease, asthma, type-1 diabetes, SLE, psoriasis, COPD and sepsis.

In another embodiment of the invention, the antibody binds PD-1 and is for use in restoring T cell function in HIV-1 infection and therapy of AIDS.

In another embodiment of the invention, the antibody binds LIGHT and is for use in the treatment of a disease selected from the group consisting of: hepatitis, inflammatory bowel disease, graft-versus-host disease (GVHD) and inflammation.

In another embodiment of the invention, the antibody binds EGF, VEGF, TGFalpha or HGF and is for use in the treatment of: malignant diseases, such as solid cancers.

In another embodiment of the invention, the antibody binds PDGF and is for use in the treatment of: diseases in which abnormal cell proliferation cell migration and/or angiogenesis occurs, such as atherosclerosis, fibrosis, and malignant diseases.

In another embodiment of the invention, the antibody binds NGF and is for use in the treatment of: neurological diseases, neurodegenerative diseases, such as Alzheimer's disease and Parkinson's disease, or cancer, such as prostate cancer.

In another embodiment of the invention, the antibody binds complement or a related components such as: C1q, C4, C2, C3, C5, C6, C7, C8, C9, MBL, or factor B and is for use in: diseases in which complement and related components play a detrimental role, such as organ transplant rejection, multiple sclerosis, Guillain-Barré syndrome, hemolytic anemia, Paroxysmal Nocturnal Hemoglobinuria, stroke, heart attacks, burn injuries, age-related macular degeneration, asthma, lupus, arthritis, myasthenia gravis, anti-phospholipid syndrome, sepsis and ischemia reperfusion injury.

In another embodiment of the invention, the antibody binds a Matrix Metallo Protease such as any of MMP1 to MMP28 and is for use in the treatment of: inflammatory and autoimmune diseases, cancer, including metastatic cancer; arthritis, inflammation, cardiovascular diseases, cerebrovascular diseases such as stroke or cerebral aneurysms, pulmonary diseases such as asthma, ocular diseases such as corneal wound healing or degenerative genetic eye diseases, gastrointestinal diseases such as inflammatory bowel disease or ulcers, oral diseases such as dental caries, oral cancer or periodontitis, ischemia reperfusion injury or sepsis.

In another embodiment of the invention, the antibody binds CD32b and is for use in enhancement of T-cell responses to tumor antigens and ADCC/phagocytosis by macrophages, in combination with another therapeutic antibody; vaccination, immunotherapy of B-cell lymphoma's, asthma or allergy.

In another embodiment of the invention, the antibody binds CD200 or CD200R and is for use in the treatment of: asthma, rheumatoid arthritis, GVHD, other autoimmune diseases, or cancer, such as solid tumors or lymphomas.

In another embodiment of the invention, the antibody binds Killer Immunoglobulin-Like Receptors (KIRs), NKG2D or related molecules, leukocyte-associated immunoglobulin-like receptors (LAIRs), or ly49 and is for use in the treatment of: cancer, such as solid tumors or lymphomas; asthma, rheumatoid arthritis, GVHD or other autoimmune diseases.

In another embodiment of the invention, the antibody binds PD-L2 and is for use in the treatment of: cancer, asthma, or for use in vaccine enhancement.

In another embodiment of the invention, the antibody binds CD26 and is for use in the treatment of: atherosclerosis, GVHD, or auto-immune diseases.

In another embodiment of the invention, the antibody binds BST-2 and is for use in the treatment of: asthma, atherosclerosis, rheumatoid arthritis, psoriasis, Crohn's disease, ulcerative cholitis, atopic dermatitis, sepsis or inflammation.

In another embodiment of the invention, the antibody binds ML-IAP (melanoma inhibitor of apoptosis protein) and is for use in the treatment of melanoma.

In another embodiment of the invention, the antibody binds cathepsin D and is for use in the treatment of: malignant diseases such as breast cancer, ovarian cancer, glioma, NSCLC, bladder cancer, endometrial cancer, liver cancer, sarcoma, gastric cancer, SCCHN, prostate cancer or colorectal cancer.

In another embodiment of the invention, the antibody binds CD40 or CD40R and is for use in the treatment of: cancer, in particular B-cell lymphomas, B-cell-related or -mediated diseases, autoimmune diseases such as psoriatic arthritis, rheumatoid arthritis, multiple sclerosis, psoriasis, Crohn's disease or ulcerative cholitis.

In another embodiment of the invention, the antibody binds CD86 and is for use in conjunction with organ transplantation.

In another embodiment of the invention, the antibody binds a B cell receptor and is for use in the treatment of: B-cell-related or -mediated diseases, such as B cell lymphoma's, leukemia, autoimmune diseases, inflammation or allergy.

In another embodiment of the invention, the antibody binds CD79 and is for use in the treatment of B-cell-related or -mediated diseases, such as B-cell lymphomas, leukemia, autoimmune diseases, inflammation or allergy.

In another embodiment of the invention, the antibody binds a T cell receptor and is for use in the treatment of T-cell-related or -mediated diseases, such as T-cell lymphomas, leukemia, autoimmune diseases, inflammation or allergy.

In another embodiment of the invention, the antibody binds FcalphaRI and is for use in the treatment of a disease or disorder selected from: allergic asthma or other allergic diseases such as allergic rhinitis, seasonal/perennial allergies, hay fever, nasal allergies, atopic dermatitis, eczema, hives, urticaria, contact allergies, allergic conjunctivitis, ocular allergies, food and drug allergies, latex allergies, or insect allergies, or IgA nephropathy, such as IgA pemphigus.

In another embodiment of the invention, the antibody binds CD25 and is for use in the treatment of a disease or disorder selected from the group consisting of: transplant rejection, graft-versus-host disease, inflammatory, immune or autoimmune diseases, inflammatory or hyperproliferative skin disorders, lymphoid neoplasms, malignancies, hematological disorders, skin disorders, hepato-gastrointestinal disorders, cardiac disorders, vascular disorders, renal disorders, pulmonary disorders, neurological disorders, connective tissue disorders, endocrinological disorders, viral infections.

In another embodiment of the invention, the antibody binds IL-15 or the IL15 receptor and is for use in the treatment of a disease or disorder selected from the group consisting of: arthritides, gout, connective disorders, neurological disorders, gastrointestinal disorders, hepatic disorders, allergic disorders, hematological disorders, skin disorders, pulmonary disorders, malignant disorders, endocrinological disorders, vascular disorders, infectious disorders, kidney disorders, cardiac disorders, circulatory disorders, metabolic disorders, bone, disorders and muscle disorders.

In another embodiment of the invention, the antibody binds IL-8 and is for use in the treatment of a disease or disorder selected from the group consisting of: palmoplantar pustulosis (PPP), psoriasis, or other skin diseases, inflammatory, autoimmune and immune disorders, alcoholic hepatitis and acute pancreatitis, diseases involving IL-8 mediated angiogenesis.

In another embodiment of the invention, the antibody binds CD20 and is for use in the treatment of a disease or disorder selected from the group consisting of: rheumatoid arthritis, (auto)immune and inflammatory disorders, non-Hodgkin's lymphoma, B-CLL, lymphoid neoplasms, malignancies and hematological disorders, infectious diseases and connective disorders, neurological disorders, gastrointestinal disorders, hepatic disorders, allergic disorders, hematological disorders, skin disorders, pulmonary disorders, malignant disorders, endocrinological disorders, vascular disorders, infectious disorders, kidney disorders, cardiac disorders, circulatory disorders, metabolic disorders, bone and muscle disorders, and immune mediated cytopenia.

In another embodiment of the invention, the antibody binds CD38 and is for use in the treatment of a disease or disorder selected from the group consisting of: tumorigenic disorders, immune disorders in which CD38 expressing B cells, plasma cells, monocytes and T cells are involved, acute respiratory distress syndrome and choreoretinitis, rheumatoid arthritis, inflammatory, immune and/or autoimmune disorders in which autoantibodies and/or excessive B and T lymphocyte activity are prominent, skin disorders, immune-mediated cytopenias, connective tissue disorders, arthritides, hematological disorders, endocrinopathies, hepato-gastrointestinal disorders, nephropathies, neurological disorders, cardiac and pulmonary disorders, allergic disorders, ophthalmologic disorders, infectious diseases, gynecological-obstetrical disorders, male reproductive disorders, transplantation-derived disorders, In another embodiment of the invention, the antibody binds EGFr and is for use in the treatment of a disease or disorder selected from the group consisting of: cancers (over)expressing EGFr and other EGFr related diseases, such as autoimmune diseases, psoriasis, inflammatory arthritis.

In another embodiment of the invention, the antibody binds CD4 and is for use in the treatment of a disease or disorder selected from the group consisting of: rheumatoid arthritis, (auto)immune and inflammatory disorders, cutaneous T cell lymphomas, non-cutaneous T cell lymphomas, lymphoid neoplasms, malignancies and hematological disorders, infectious diseases, and connective disorders, neurological disorders, gastrointestinal disorders, hepatic disorders, allergic disorders, hematologic disorders, skin disorders, pulmonary disorders, malignant disorders, endocrinological disorders, vascular disorders, infectious disorders, kidney disorders, cardiac disorders, circulatory disorders, metabolic disorders, bone disorders, muscle disorders, immune mediated cytopenia, and HIV infection/AIDS.

In another embodiment of the invention, the antibody binds CD28 and is for use in the treatment of a disease or disorder selected from the group consisting of: an inflammatory disease, autoimmune disease and immune disorder.

In another embodiment of the invention, the antibody binds tissue factor, or a complex of Factor VII and tissue factor and is for use in the treatment of a disease or disorder selected from the group consisting of: vascular diseases, such as myocardial vascular disease, cerebral vascular disease, retinopathy and macular degeneration, and inflammatory disorders.

In a further aspect, the invention relates to the use of a stabilized IgG4 antibody that binds any of the antigen mentioned herein above for the preparation of a medicament for the treatment of a disease or disorder as mentioned herein above in connection with said target antigen.

The present invention is further illustrated by the following examples which should not be construed as further limiting.

EXAMPLES

Example 1: Oligonucleotide Primers and PCR Amplification

Oligonucleotide primers were synthesized and quantified by Isogen Bioscience (Maarssen, The Netherlands). Primers were dissolved in H$_2$O to 100 pmol/μl and stored at −20° C. A summary of all PCR and sequencing primers is given below. For PCR, PfuTurbo® Hotstart DNA polymerase (Stratagene, Amsterdam, The Netherlands) was used according to the manufacturer's instructions. Each reaction mix contained 200 μM mixed dNTPs (Roche Diagnostics, Almere, The Netherlands), 6.7 pmol of both the forward and reverse primer, 100 ng of genomic DNA or 1 ng of plasmid DNA and 1 unit of PfuTurbo® Hotstart DNA polymerase in PCR reaction buffer (supplied with polymerase) in a total volume of 20 μl. PCR reactions were carried out with a TGradient Thermocycler 96 (Whatman Biometra, Goettingen, Germany) using a 32-cycle program: denaturing at 95° C. for 2 min; 30 cycles of 95° C. for 30 sec, a 60-70° C. gradient (or another specific annealing temperature) for 30 sec, and 72° C. for 3 min; final extension at 72° C. for 10 min. If appropriate, the PCR mixtures were stored at 4° C. until further analysis or processing.

Example 2: Agarose Gel Electrophoresis

Agarose gel electrophoresis was performed according to Sambrook (Sambrook, Russell et al. 2000 Molecular cloning. A laboratory manual (third edition), Cold Spring Harbor Laboratory Press) using gels of 50 ml, in 1×Tris Acetate EDTA buffer. DNA was visualized by the inclusion of ethidium bromide in the gel and observation under UV light. Gel images were recorded by a CCD camera and an image analysis system (GeneGnome; Syngene, via Westburg B.V., Leusden, The Netherlands).

Example 3: Analysis and Purification of PCR Products and Enzymatic Digestion Purification of desired PCR fragments was carried out using a MinElute PCR Purification Kit (Qiagen, via Westburg, Leusden, The Netherlands; product #28006), according to the manufacturer's instructions. Isolated DNA was quantified by UV spectroscopy and the quality was assessed by agarose gel electrophoresis.

Alternatively, PCR or digestion products were separated by agarose gel electrophoresis (e.g. when multiple fragments were present) using a 1% Tris Acetate EDTA agarose gel. The desired fragment was excised from the gel and recovered using the QIAEX II Gel Extraction Kit (Qiagen; product #20051), according to the manufacturer's instructions.

Example 4: Quantification of DNA by UV Spectroscopy

Optical density of nucleic acids was determined using a NanoDrop ND-1000 Spectrophotometer (Isogen Life Science, Maarssen, The Netherlands) according to the manufacturer's instructions. The DNA concentration was measured by analysis of the optical density (OD) at 260 nm (one OD$_{260nm}$ unit=50 μg/ml). For all samples, the buffer in which the nucleic acids were dissolved was used as a reference.

Example 5: Restriction Enzyme Digestions

Restriction enzymes and supplements were obtained from New England Biolabs (Beverly, Mass., USA) or Fermetas (Vilnius, Lithuania) and used according to the manufacturer's instructions.

DNA (100 ng) was digested with 5 units of enzyme(s) in the appropriate buffer in a final volume of 10 μl (reaction volumes were scaled up as appropriate). Digestions were incubated at the recommended temperature for a minimum of 60 min. For fragments requiring double digestions with restriction enzymes which involve incompatible buffers or temperature requirements, digestions were performed sequentially. If necessary digestion products were purified by agarose gel electrophoresis and gel extraction.

Example 6: Ligation of DNA Fragments

Ligations of DNA fragments were performed with the Quick Ligation Kit (New England Biolabs) according to the manufacturer's instructions. For each ligation, vector DNA was mixed with approximately three-fold molar excess of insert DNA.

Example 7: Transformation of E. coli

Plasmid DNA (1-5 µl of DNA solution, typically 2 µl of DNA ligation mix) was transformed into One Shot DH5α-T1R or MACH-1 T1R competent E. coli cells (Invitrogen, Breda, The Netherlands; product #12297-016) using the heat-shock method, according to the manufacturer's instructions. Next, cells were plated on Luria-Bertani (LB) agar plates containing 50 µg/ml ampicillin. Plates were incubated for 16-18 h at 37° C. until bacterial colonies became evident.

Example 8: Screening of Bacterial Colonies by PCR

Bacterial colonies were screened for the presence of vectors containing the desired sequences via colony PCR using the HotStarTaq Master Mix Kit (Qiagen; product #203445) and the appropriate forward and reverse primers. Selected colonies were lightly touched with a 20 µl pipette tip and touched briefly in 2 ml LB for small scale culture, and then resuspended in the PCR mix. PCR was performed with a TGradient Thermocycler 96 using a 35-cycle program: denaturation at 95° C. for 15 min; 35 cycles of 94° C. for 30 sec, 55° C. for 30 sec and 72° C. for 2 min; followed by a final extension step of 10 min at 72° C. If appropriate, the PCR mixtures were stored at 4° C. until analysis by agarose gel electrophoresis.

Example 9: Plasmid DNA Isolation from E. coli Culture

Plasmid DNA was isolated from E. coli cultures using the following kits from Qiagen (via Westburg, Leusden, The Netherlands), according to the manufacturer's instructions. For bulk plasmid preparation (50-150 ml culture), either a HiSpeed Plasmid Maxi Kit (product #12663) or a HiSpeed Plasmid Midi Kit (product #12643) was used. For small scale plasmid preparation (±2 ml culture) a Qiaprep Spin Miniprep Kit (product #27106) was used and DNA was eluted in 50 µl elution buffer (supplied with kit).

Example 10: DNA Sequencing

Plasmid DNA was sequenced using standard procedures known in the art. Sequences were analyzed using Vector NTI software (Informax, Oxford, UK).

Example 11: Transient Expression in HEK-293F Cells

Freestyle™ 293-F (a HEK-293 subclone adapted to suspension growth and chemically defined Freestyle medium, e.g. HEK-293F) cells were obtained from Invitrogen and transfected according to the manufacturer's protocol using 293fectin (Invitrogen).

Example 12: Construction of pTomG4; a Vector for the Expression of Variable Heavy Chain Regions with the Constant Region of Human IgG4

Genomic DNA was isolated from a blood sample of a volunteer and used as a template in a PCR with primers IGG4gene2f and IGG4gene2r (see table below), amplifying the complete genomic constant region of the heavy chain of IgG4 and introducing suitable restriction sites for cloning into the mammalian expression vector pEE6.4 (Lonza Biologics). The PCR fragment was purified and cloned into pEE6.4. For this the PCR product was digested with HindIII and EcoRI, followed by heat inactivation of the restriction enzymes. The pEE6.4 vector was digested HindIII and EcoRI, followed by heat inactivation of the restriction enzymes and dephosphorylation of the vector fragment with shrimp alkaline phosphatase, followed by heat inactivation of the phosphatase. The IgG4 fragment and the pEE6.4HindIII/EcoRI dephosphorylated vector were ligated and transformed into competent MACH1-T1$^R$ cells (Invitrogen). Three clones were grown in LB and plasmid DNA was isolated from a small culture (1.5 mL). Restriction digestion revealed a pattern consistent with the cloning of the IgG4 fragment in the pEE6.4 vector. Plasmid DNA from two clones was transformed in DH5α-T1R E. coli and plasmid DNA was isolated and the constructs were checked by sequence analysis of the insert and one clone was found to be identical to a genomic IgG4 clone from the Genbank database, apart from some minor differences in introns. These differences are presumably either polymorphisms or sequence faults in the Genbank sequence. The plasmid was named pTomG4.

TABLE 1 primer sequences

| Name | Oligonucleotide Sequence |
| --- | --- |
| VLexbetv1rev | AGCCACCGTACGTTTGATTTCCAGCTTGGTGCCTCC (SEQ ID NO: 1) |
| VLex betv1for | GATGCAAGCTTGCCGCCACCATGGAGTCACAGATTC AGGCATTT (SEQ ID NO: 2) |
| VHexbetv1rev | CGATGGGCCCTTGGTGCTGGCTGAGGAGACGGTGAC TGAGGT (SEQ ID NO: 3) |
| VHexbetV1for | GATGCAAGCTTGCCGCCACCATGAAATGCAGCTGGG TTATCTTC (SEQ ID NO: 4) |
| VLexfeld1rev | AGCCACCGTACGTTTTATTTCCAACTTTGTCCCCGA (SEQ ID NO: 5) |
| VLex feld1for | GATGCAAGCTTGCCGCCACCATGGAATCACAGACTC AGGTCCTC (SEQ ID NO: 6) |
| VHexfeld1rev | CGATGGGCCCTTGGTGCTGGCTGCAGAGAAAGTGAC CAGAGT (SEQ ID NO: 7) |
| VHexfeld1for | GATGCAAGCTTGCCGCCACCATGGGATGGAGCTATA TCATCCTC (SEQ ID NO: 8) |
| IGG4gene2r | TGAGAATTCGGTGGGTGCTTTATTTCCATGCT (SEQ ID NO: 9) |
| IGG4gene2f | GTAGAAGCTTACCATCGCGGATAGACAAGAACC (SEQ ID NO: 10) |
| RACEKmm1 | TGTTAACTGCTCACTGGATGGTGGGA (SEQ ID NO: 11) |
| RACEG1mm1 | TCCCTGGGCACAATTTTCTTGTCCACC (SEQ ID NO: 12) |
| ShortUPMH3 | TGAAAGCTTCTAATACGACTCACTATAGGGC (SEQ ID NO: 13) |
| LongUPMH3 | TGAAGCTTCTAATACGACTCACTATAGGGCAAGCAG TGGTATCAACGCAGAGT (SEQ ID NO: 14) |

Example 13: Cloning of the Variable Regions of the Mouse Anti-Betv1 and Anti-Feld1 Antibodies Total RNA was prepared from 0.3×10$^5$ (Betv1) or 0.9×10$^5$ (Feld1) mouse hybridoma cells (For Betv1: clone 2H8 from Akkerdaas, van Ree et al. 1995 Allergy 50(3), 215-220 and for Feld1: clone 4F7 from de Groot et al. 1988 3. Allergy Clin. Immunol. 82, 778) with the RNeasy kit (Qiagen, Westburg, Leusden, Netherlands) according to the manufacturer's protocol.

5'-RACE-Complementary DNA (cDNA) of RNA was prepared from approximately 100 ng total RNA, using the SMART RACE cDNA Amplification kit (BD Biosciences Clontech, Mountain View, Calif., USA), following the manufacturer's protocol. The VL and VH regions of the Betv1 and Feld1 antibody were amplified by PCR. For this PfuTurbo® Hotstart DNA polymerase (Stratagene) was used according to the manufacturer's instructions. Each reaction mix contained 200 μM mixed dNTPs (Roche Diagnostics), 12 pmol of the reverse primer (RACEG1mm1 for the VH region and RACEKmm1 for the VL region), 7.2 pmol UPM-Mix (UPM-Mix: 2 μM ShortUPMH3 and 0.4 μM LongUPMH3 oligonucleotide), 0.6 μl of the 5'RACE cDNA template as described above, and 1.5 unit of PfuTurbo® Hotstart DNA polymerase in PCR reaction buffer (supplied with polymerase) in a total volume of 30 μl.

PCR reactions were carried out with a TGradient Thermocycler 96 (Whatman Biometra) using a 35-cycle program: denaturing at 95° C. for 2 min; 35 cycles of 95° C. for 30 sec, a 55° C. for 30 sec, and 72° C. for 1.5 min; final extension at 72° C. for 10 min. The reaction products were separated by agarose gel electrophoresis on a 1% TAE agarose gel and stained with ethidium bromide. Bands of the correct size were cut from the gels and the DNA was isolated from the agarose using the QiaexII gel extraction kit (Qiagen).

Gel isolated PCR fragments were A tailed by a 10 min 72° C. incubation with 200 μM dATP and 2.5 units Amplitaq (Perkin Elmer) and purified using minielute columns (Qiagen). A-tailed PCR fragments were cloned into the pGEMTeasy vector (Promega) using the pGEMT easy vector system II kit (Promega), following the manufacturer's protocol. 2 μl of the ligation mixture was transformed into OneShot DH5αT1R competent *E. coli* (Invitrogen) and plated on LB/Amp/IPTG/Xgal plates. Four, insert containing, white colonies each for the VH and VL sequences were picked and the inserts were sequenced. The deduced amino acid sequences of the VH and VL of Betv1 are given in SEQ ID NO:15 and 16 and the deduced amino acid sequences of Feld1 are depicted in SEQ ID NO:17 and 18.

```
VH sequence Betv1 (SEQ ID NO: 15):
mkcswvifflmavvtgvnsevqlqqsgaelvkpgasvkisctasgfnikd
tyihwvkqrpeqglewvgridpatgntrydpkfqgkatitadtssntayl
qissltsedtavyycasfrpgyaldywgqgtsvtvss VL sequence Betv1 (SEQ ID NO: 16):
mesqiqafvfvflwlsgvdgdivmtqshkfmstsvgdrvsftckasqdvf
tavawyqqkpgqspklliywastrrtgvpdrftgsgsgtdytltissvqa
edialyycqqhfstpptfgggtkleik VH sequence Feld1 (SEQ ID No: 17):
mgwsyiillflvatatdvhsqvqlqqpgaelvkpgasvkisckasgysfts
ywmhwlkqrpgqglewlgeinpnngrtyynekfktkatitvdkssstaym
qlnsltsedsavyycarritmvesfaywgqgtlvtfsa VL sequence Feld1 (SEQ ID NO: 18):
mesqtqvlmsllfwvsgtcgdivmtqspssltvtagekvtmsckssqsll
nsgnqknyltwyqqkpgqppklliywastresgvpdrftgsgsgtdfslt
issvqaedlaiyycqndysypftfgsgtkleik
```

Example 14: Construction of pConG1fBetV1: A Vector for the Production of the Heavy Chain of Betv1-IgG1

The $V_H$ coding region of mouse anti-BetV1 antibody was amplified by PCR from a plasmid containing this region (example 13) using the primers VHexbetv1 for and VHexbetv1rev, introducing suitable restriction sites for cloning into pConG1f0.4 and an ideal Kozak sequence. The VH fragment was gel purified and cloned into pConG1f0.4. For this the PCR product and the pConKappa0.4 vector were digested with HindIII and ApaI and purified. The VH fragment and the pConG1f0.4HindIII-ApaI digested vector were ligated and transformed into competent DH5α-T1R cells. A clone was selected containing the correct insert size and the correct sequence was confirmed. This plasmid was named pConG1fBetv1.

Example 15: Construction of pConKBetv1: A Vector for the Production of the Light Chain of Betv1

The $V_L$ coding region mouse anti-BetV1 antibody was amplified from a plasmid containing this region (example 13) using the primers VLexbetv1for and VLexbetv1rev, introducing suitable restriction sites for cloning into pConK0.4 and an ideal Kozak sequence. The PCR product and the pConKappa0.4 vector were digested with HindIII and BsiWI and purified. The $V_L$ fragment and the pConKappa0.4HindIII-BsiWI digested vector were ligated and transformed into competent DH5a T1R *E. coli*. A clone was selected containing the correct insert size and the sequence was confirmed. This plasmid was named pConK-Betv1.

Example 16: Construction of pTomG4Betv1: A Vector for the Production of the Heavy Chain of Betv1-IgG4

To construct a vector for expression of Betv1-IgG4, the VH region of BetV1 was cloned in pTomG4. For this, pTomG4 and pConG1fBetv1 were digested with HindIII and ApaI and the relevant fragments were isolated. The Betv1 VH fragment and the pTomG4HindIII-ApaI digested vector were ligated and transformed into competent DH5α-T1R cells. A clone was selected containing the correct insert size and the sequence was confirmed. This plasmid was named pTomG4Betv1.

Example 17: Construction of pConG1fFeld1: A Vector for the Production of the Heavy Chain of Feld1-IgG1

The $V_H$ coding region of mouse anti-Feld1 antibody was amplified by PCR from a plasmid containing this region (example 13) using the primers VHexfeld1for and VHexfeld1rev, introducing suitable restriction sites for cloning into pConG1f0.4 and an ideal Kozak sequence. The VH fragment was gel purified and cloned into pConG1f0.4. For this the PCR product and the pConKappa0.4 vector were digested with HindIII and ApaI and purified. The $V_H$ fragment and the pConG1f0.4HindIII-ApaI digested vector were ligated and transformed into competent DH5α-T1R cells. A clone was selected containing the correct insert size and the correct sequence was confirmed. This plasmid was named pConG1fFel1.

Example 18: Construction of pConKFeld1: A Vector for the Production of the Light Chain of Feld1

The $V_L$ coding region mouse anti-' Feld1 antibody was amplified from a plasmid containing this region (example 13) using the primers VLexfeld1for and VLexfeld1rev, introducing suitable restriction sites for cloning into pConK0.4 and an ideal Kozak sequence. The PCR product and the pConKappa0.4 vector were digested with HindIII and BsiWI and purified. The $V_L$ fragment and the pConKappa0.4HindIII-BsiWI digested vector were ligated and transformed into competent DH5α T1$^R$ E. coli. A clone was selected containing the correct insert size and the sequence was confirmed. This plasmid was named pConK-Feld1.

Example 19: Construction of pTomG4Feld1: A Vector for the Production of the Heavy Chain of Feld1-IgG4

To construct a vector for expression of Feld1-IgG4, the VH region of Feld1 was cloned in pTomG4. For this, pTomG4 and pConG1f Feld1 were digested with HindIII and ApaI and the relevant fragments were isolated. The Feld1 VH fragment and the pTomG4HindIII-ApaI digested vector were ligated and transformed into competent DH5α-T1R cells. A clone was selected containing the correct insert size and the sequence was confirmed. This plasmid was named pTomG4Feld1.

Example 20: Construction of Antibody Expression Vectors for the Expression of 2F8-IgG4 and 7D8-IgG4

Expression vectors for the expression of HuMab 2F8 (IgG1-EGFR) and HuMab 7D8 (IgG1-CD20) were constructed. The VH and VL coding regions of HuMab 2F8 (WO 02/100348) and HuMab 7D8 (WO 04/035607) were cloned in the expression vector pConG1f (Lonza Biologics) for the production of the IgG1 heavy chain and pConKappa for the production of the kappa light chain, yielding the vectors pConG1f2F8, pConG1f7D8, pConKappa2F8 and pConKappa7D8. The VH regions of pConG1f2F8 and pConG1f7D8 were removed from these vectors by a HindIII/ApaI digestion and inserted into a HindIII/ApaI digested pTomG4 vector, resulting in pTomG42F8 and pTomG47D8 respectively.

Example 21: Production of Betv1-IgG1, Betv1-IgG4, Feld1-IgG1 and Feld1-IgG4 by Transient Expression in HEK-293F Cells Antibodies were produced from all constructs by cotransfecting the relevant heavy and light chain vectors in HEK-293F cells using 293fectin according to the manufacturer's instructions. For Betv1-IgG1, pConG1Betv1 and pConK-Betv1 were coexpressed. For Betv1-IgG4, pTomG4Betv1 and pConKBetv1 were coexpressed. For Feld1-IgG1, pConG1Feld1 and pConKFeld1 were coexpressed. For Feld1-IgG4, pTomG4Feld1 and pConKFeld1 were coexpressed. For IgG1-EGFr, pConG1f2F8 and pConKappa2F8 were coexpressed. For IgG4-EGFr, pTomG42F8 and pConKappa2F8 were coexpressed. For IgG1-CD20, pConG1f7D8 and pConKappa7D8 were coexpressed. For IgG4-CD20, pTomG47D8 and pConkappa7D8 were coexpressed.

Example 22: Purification of IgG1 and IgG4 Antibodies

IgG1 and IgG4 antibodies were purified by protein A affinity chromatography. The cell culture supernatants were filtered over a 0.20 μM dead-end filter, followed by loading on a 5 ml Protein A column (rProtein A FF, GE Healthvcare) and elution of the IgG with 0.1 M citric acid-NaOH, pH 3. The eluate was immediately neutralized with 2 M Tris-HCl, pH 9 and dialyzed overnight to 12.6 mM sodium phosphate, 140 mM NaCl, pH 7.4 (B. Braun, Oss, The Netherlands). After dialysis, samples were sterile filtered over a 0.20 μM dead-end filter. Concentration of the purified IgGs was determined by nephelometry and absorbance at 280 nm. Purified proteins were analyzed by SDS-PAGE, IEF, Mass spectrometry and Glycoanalysis.

Example 23: SDS-PAGE Analysis of Purified IgGs

After purification, the Betv1 and Feld1, IgG1 and IgG4 antibodies were analyzed on non-reducing SDS-PAGE. The Bis-Tris electrophoresis method used is a modification of the Laemmli method (Laemmli 1970 Nature 227(5259): 680-5), where the samples were run at neutral pH. The SDS-PAGE gels were stained with Coomassie and digitally imaged using the GeneGenius (Synoptics, Cambridge, UK).

Figure 1:
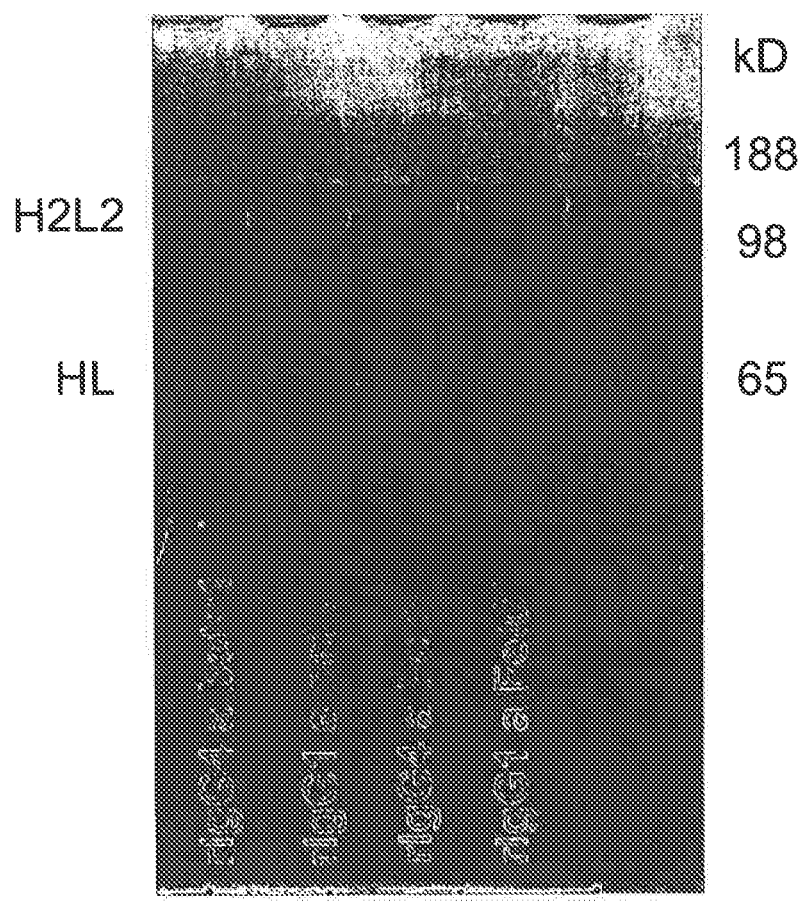
FIG. 1. SDS-Page analysis of purified recombinant IgG1 and IgG4. After purification, the Betv1 and Feld1, IgG1 and IgG4 antibodies were analyzed on non-reducing SDS-PAGE.

As can be seen in FIG. 1, Betv1 and Feld1 IgG1 showed 1 major band representing the full length tetrameric (2 heavy and two light chains) Feld1 and Betv1 IgG1 molecules. Betv1 and Feld1 IgG4 showed to have, besides the major band representing the tetrameric IgG4 molecule, substantial amounts of half-molecules (i.e. one heavy band one light chain).

Example 24: Evaluation of IgG4 Fab Arm Exchange in Mice

Five nu/nu Balb/c mice 6-8 weeks of age were used to follow the exchange of IgG4 half molecules. The mice were housed in a barrier unit of the Central Laboratory Animal Facility (Utrecht, The Netherlands) and kept in filter-top cages with water and food provided ad libitum. All experiments were approved by the Utrecht University animal ethics committee.

Chimeric antibodies were administered intraperitoneally. Blood samples (75-100 μl) were drawn at 4.25 hours, 24 hours, 48 hours and 72 hours after administration. Blood was collected in heparin-containing vials and centrifuged for 5 minutes at 10,000 g to separate plasma from cells. Plasma was stored at −20° C. for determination of antigen specific antibody and bispecific antibody levels.

In this experiment the exchange of chimeric IgG4 half molecules (n=2) was compared with the exchange of IgG1 half molecules (n=3). Mixtures of Bet v 1 and Fel d 1 specific antibodies (IgG1 or IgG4) were administered to the mice at a dose of 600 μg (300 μg of each antigen specific antibody) in 200 μl per mouse.

Plasma concentrations of Bet v 1 or Fel d 1 binding antibodies were measured in the antigen binding test. To this end, plasma samples were incubated with 0.75 mg of protein G Sepharose (Amersham Biosciences, Uppsala, Sweden) in 750 μl PBS-IAT (PBS supplemented with 1 μg/ml IVIg, 0.3% bovine serum albumin, 0.1% Tween-20 and 0.05% (w/v) NaN$_3$) in the presence of $^{125}$I-labeled Bet v 1 or $^{125}$I-labeled Fel d 1 for 24h. Next, the Sepharose was washed with PBS-T (PBS supplemented with 0.1% Tween-20 and 0.05% (w/v) NaN3) and the amount of radioactivity bound relative to the amount of radioactivity added was measured. The concentration of Bet v 1 or Fel d 1 specific IgG was calculated using purified Bet v 1 specific antibodies or Fel d 1 specific antibodies as a standard (range 0-200 ng per test as determined by nephelometer). The concentration of bispecific IgG was measured in two variants of the heterologous cross-linking assay. In the first assay, plasma was incubated for 24 h with Sepharose-coupled Bet v 1 (0.5 mg) in a total volume of 300 μl in PBS-IAT. Subsequently, the Sepharose was washed with PBS-T and incubated for 24 h with $^{125}$I-labeled Fel d 1, after which the Sepharose was washed with PBS-T and the amount of radioactivity bound relative to the amount of radioactivity added was measured. The concentration of bispecific IgG (Bet v 1-Fel d 1) was calculated using the calibration curve of the Fel d 1 binding test, which was obtained from purified Fel d 1 binding rIgG. In the second assay Fel d 1-Bet v 1 cross-linking activity was measured in a similar procedure using Sepharose-coupled rFel d 1 (0.5 mg) and $^{125}$I-labeled Bet v 1. The concentration of bispecific IgG (Fel d 1-Bet v 1) was calculated using purified Bet v 1 specific rIgG as a standard (same curve as in Bet v 1 binding test).

Figure 2:
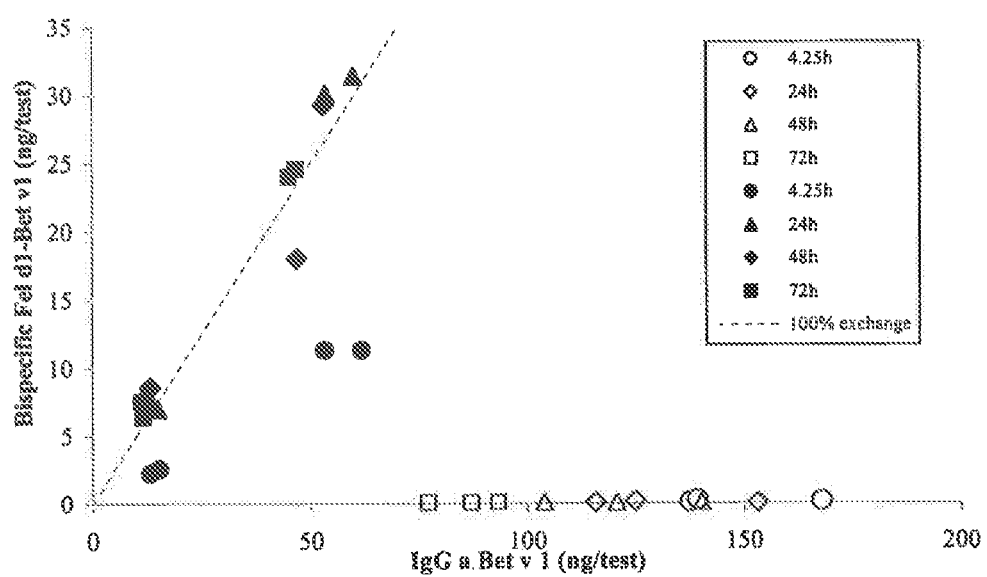
FIG. 2. Bispecific IgG levels in nu/nu Balb/c mice at different time points. The amount of bispecific IgG as determined in the heterologous cross-linking assay was plotted versus the amount of Bet v 1 specific IgG as determined in the Bet v 1 binding test. Data from IgG1 and IgG4 containing plasma samples are represented by open symbols and closed symbols, respectively. The dashed line represents the calculated amount of bispecific IgG, if the exchange of IgG half molecules is random and complete.

In FIG. 2 the concentration of bispecific IgG (Fel d 1-Bet v 1) is plotted versus the concentration of Bet v 1 binding IgG at different time points. No bispecific IgG was observed in the mice dosed with IgG1 mixes in contrast to the mice dosed with IgG4. After 24 h the generation of bispecific IgG4 was maximal and corresponded to an exchange of 100%.

Figure 3A:
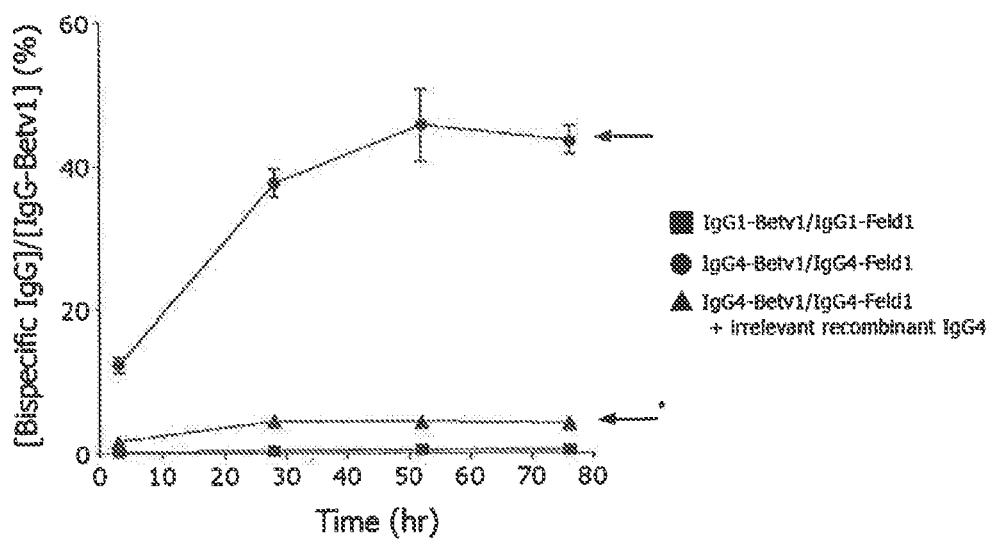
FIGS. 3A and 3B. Bispecific human IgG4 molecules are generated in vivo.

In FIG. 3A the formation of bispecific IgG4 is followed in time. Bispecific antibodies appeared in time in the plasma of mice injected with mixtures of IgG4, but not IgG1, with bispecific reactivity achieving a maximum of almost 50% after 1-2 days incubation (note: if equal amounts of IgG4-Betv1 and IgG4-Feld1 are exchanged, maximal 50% of the IgG4-Betv1 half-antibodies will be incorporated in the bispecific fraction after random and complete exchange of half-antibodies). A random Fab arm exchange between equal amounts of IgG4-Betv1 and IgG4-Feld1, would be consistent with approximately half of the IgG4 molecules acquiring bispecificity. As a control, a 20-fold-excess of an additional IgG4 directed against an irrelevant antigen (IgG4 generated from anti-EGFr antibody 2F8) was injected in mice together with IgG4-Betv1 and IgG4-Feld1. The excess irrelevant IgG4 competed with the generation of Betv1-Feld1-bispecific IgG4.

Figure 3B:
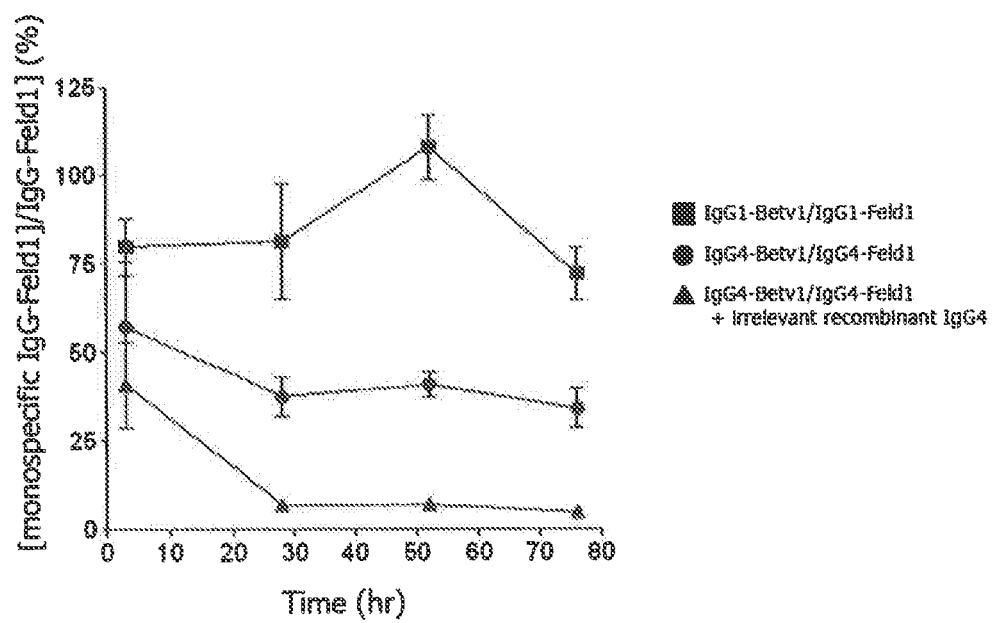

In another experiment (FIG. 3B) the same murine plasma samples were tested for their ability to cross-link radiolabeled soluble Fel d 1 to Sepharose-immobilized Fel d 1. It was found that the monospecific cross-linking activity was decreased in mice dosed with an equal mixture of IgG4s but not IgG1s, indicating a loss of monospecific cross-linking activity. A maximal reduction of ~50% was reached after about one day. In mice dosed with the additional excess of irrelevant IgG4, monospecific cross-linking activity almost completely disappeared with similar kinetics.

Figure 4:
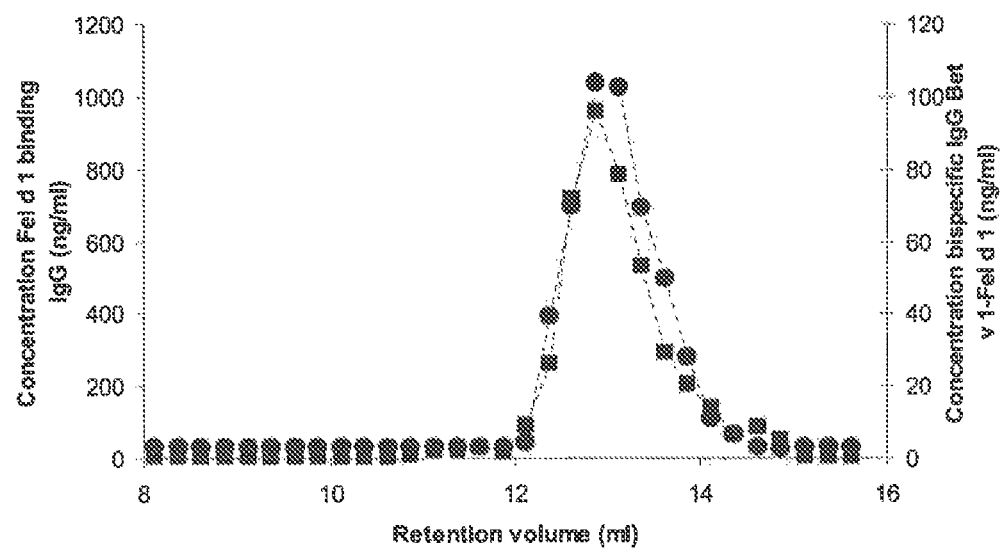
FIG. 4. SEC analysis of bispecific activity in murine plasma Plasma (10 μl) drawn at t=24 h from a mouse dosed with an IgG4 mix was fractionated on a Superdex200 column. The mouse was dosed with a mix containing 300 μg of Bet v 1 binding IgG4 and 300 μg of Fel d 1 binding IgG4. In the fractions, the concentration of Fel d 1 specific IgG (■) was measured in the antigen binding test and the concentration of bispecific IgG Bet v 1-Fel d 1 (●) was determined in the Bet v 1-Fel d 1 cross-linking assay. Calibration of this column using IVIg has revealed that monomeric, dimeric and aggregated IgG elute at 12.9, 11.0 and 8.4 ml, respectively (data not shown).

Size-exclusion chromatography was performed to exclude the possibility that bispecific activity observed in the mice dosed with IgG4 was the result of IgG aggregation (FIG. 4). For this purpose, a plasma sample (drawn at t=24h) was fractionated on a Superdex200 column, after which Fel d 1 binding IgG and Bet v 1-Fel d 1 cross-linking IgG were measured in the fractions. Fel d 1 binding antibodies eluted in one peak with a retention volume of ~12.9 ml, which corresponds to the retention volume of monomeric IgG. The heterologous Bet v 1-Fel d 1 cross-linking activity was detected in the same fractions indicating that bispecific activity was associated with monomeric IgG. In the rIgG1 containing plasma no Bet v 1-Fel d 1 cross-linking activity was present before fractionation. Also in the eluted fractions no heterologous cross-linking activity was measured (data not shown).

Example 25: Evaluation of Fab Arm Exchange Activity by Whole Blood (Components)

Chimeric antibodies were mixed and subsequently incubated with whole blood, blood cells, plasma or serum to investigate the exchange activity of whole blood (components).

In this experiment the exchange of IgG4 half molecules was evaluated in whole blood from two healthy blood donors, A and B, in which the endogenous plasma level of IgG4 was determined by nephelometry (being 346 and 554 μg/ml, respectively). Whole blood was obtained in vacutainers supplemented with TFPI (Tissue Factor Pathway Inhibitor from Chiron Corporation, Emeryville, Calif.) in a final concentration of 40 μg/ml. Blood cells and plasma were obtained by centrifugation of whole blood. The cellular fraction was washed 3 times with Optimem (Invitrogen, Breda, The Netherlands) and subsequently resuspended in Optimem. Serum was obtained by incubating whole blood in a glass vacutainer with clot activator for 30 min at 37° C., after which the clotted blood was spinned down. The exchange of IgG4 half molecules was evaluated and compared to the exchange of IgG1 half molecules. As a control the blood samples were also incubated in the absence of chimeric antibodies. The following antibodies mixtures were prepared in PBS:
1. Bet v 1 specific IgG4 (10 μg) and Fel d 1 specific IgG4 (10 μg)
2. Bet v 1 specific IgG1 (10 μg) and Fel d 1 specific IgG1 (10 μg)

These antibody mixtures were incubated with blood, blood cells, plasma or serum in a total volume of 100 μl (final concentration for each antibody was 0.1 μg/ml) on a horizontal orbital shaker (125 rpm) at 37° C. Final hematocrit in the incubation mixtures with whole blood and blood cells was around ~40%. After 24 h the incubation mixtures were centrifuged for 1 min at 2800 rpm in an Eppendorf centrifuge, after which a sample of 10 μl was drawn in 500 μl PBS-AT (PBS supplemented with 0.3% bovine serum albumin, 0.1% Tween-20 and 0.05% (w/v) NaN$_3$). Samples were stored, if necessary, at 4° C.

Bispecific activity (i.e. Fel d 1-Bet v 1 cross-linking activity) was measured in the heterologous cross-linking assay. In this assay, a sample was incubated for 24 h with 0.5 mg Sepharose-coupled recombinant Fel d 1 in a total volume of 300 μl in PBS-IAT (PBS-AT supplemented with 1 μg/ml IVIg). Subsequently, the Sepharose was washed with PBS-T and incubated for 24 h with $^{125}$I-labeled Bet v 1, after which the Sepharose was washed with PBS-T and the amount of radioactivity bound relative to the amount of radioactivity added was measured.

Figure 5A:
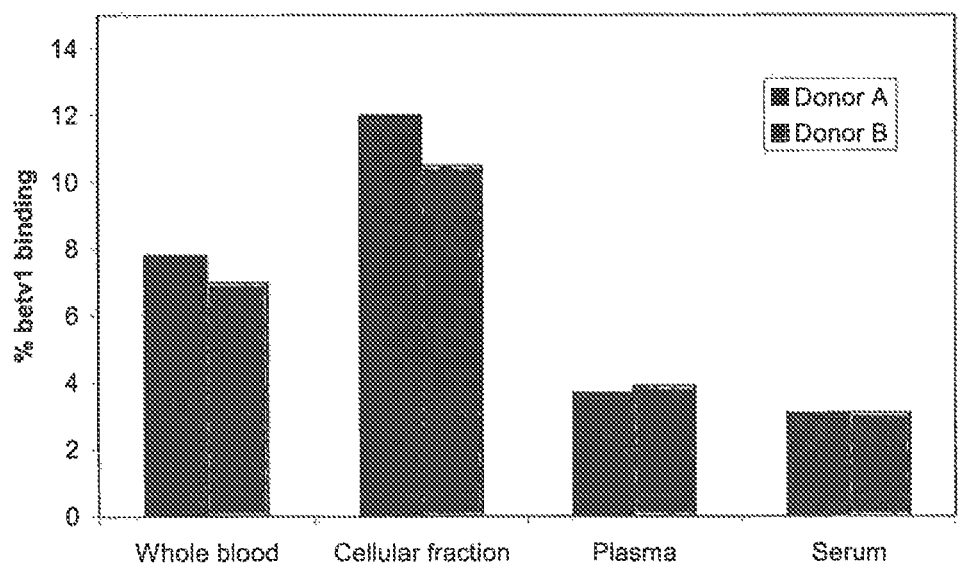
FIGS. 5A-C. Fab arm exchange of IgG in whole blood components
Figure 5B:
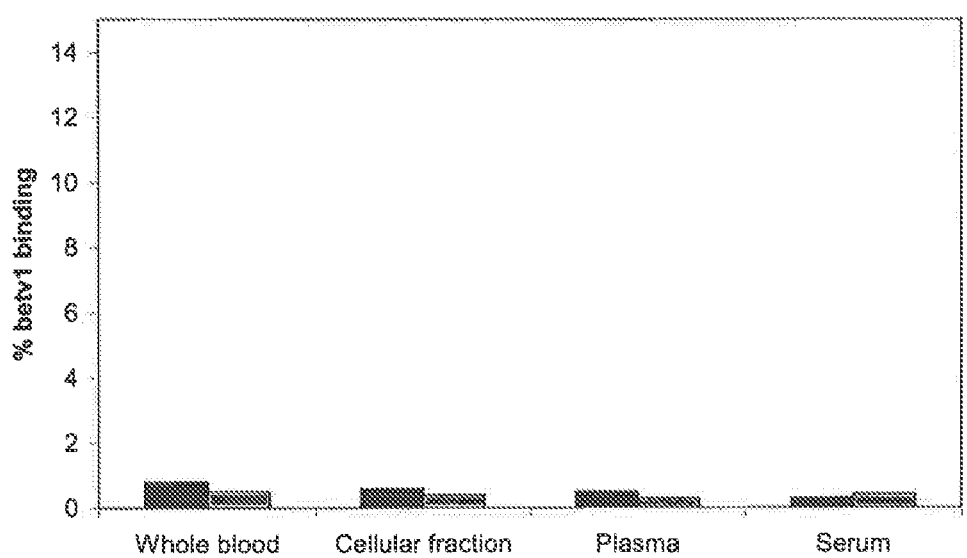
Figure 5C:
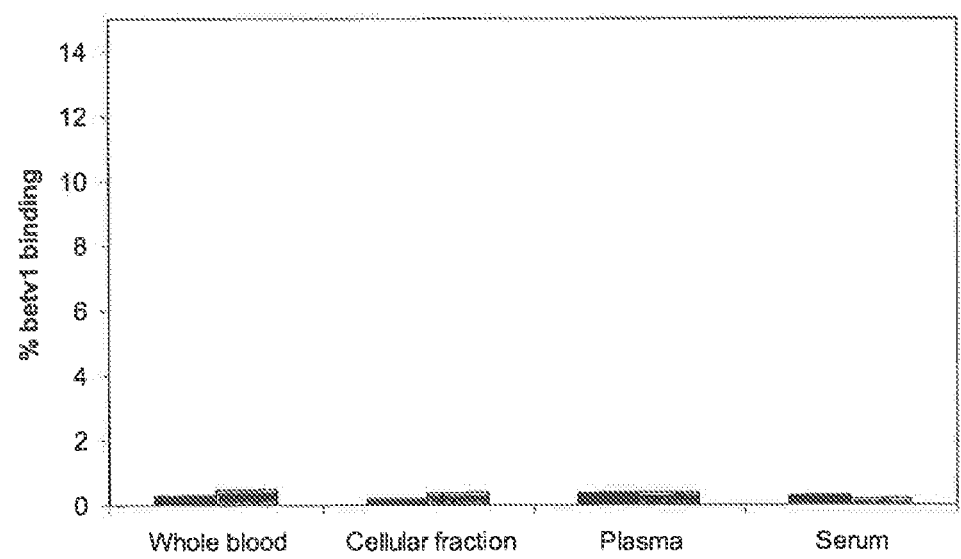

In FIGS. 5A-C bispecific activity is represented as percentage bound $^{125}$I-labeled Bet v 1, which was determined in the heterologous cross-linking assay. Bispecific activity is a measure for the exchange of IgG4 half molecules, which was primarily observed in whole blood and the cellular fraction of whole blood (FIG. 5a). Bispecific levels in the cellular fraction were even higher than in whole blood. This is most likely explained by the fact that in the cellular fraction endogenous IgG4, which can also be exchanged with the added chimeric IgG4 antibodies, is no longer present. Some bispecific activity was also observed in plasma and serum, but this activity was much lower than observed in whole blood and only slightly higher than background level, being 1.7%, which was obtained by incubating the IgG4 mixture in Optimem. No bispecific activity was observed in any of the incubations containing IgG1 (FIG. 5B). Also in the control incubations without chimeric antibodies no bispecific activity was observed (FIG. 5C). Size-exclusion chromatography was performed to exclude the possibility that bispecific activity observed in the IgG4 mix was the result of IgG aggregation. For this purpose, a sample (drawn at t=24h) was fractionated on a Superdex200 column, after which Fel d 1 binding IgG and Bet v 1-Fel d 1 cross-linking IgG were measured in the fractions. Fel d 1 binding antibodies eluted in one peak with a retention volume of ~12.9 ml, which corresponds to the retention volume of monomeric IgG. The heterologous Bet v 1-Fel d 1 cross-linking activity was detected in the same fractions indicating that bispecific activity was associated with monomeric IgG (data not shown).

Example 26: Evaluation of Blood Cell Mediated IgG4 Fab Arm Exchange Activity

Chimeric antibodies were mixed and subsequently incubated with three different types of human blood cells (i.e. mononuclear cells (MNC), erythrocytes and platelets) to investigate IgG4 exchange activity.

Whole blood from an anonymous donor was drawn in a heparin containing vacutainer and subsequently centrifuged in Percoll (Pharmacia Fine Chemicals, Uppsala, Sweden) to isolate MNCs. The isolated MNCs were resuspended in Optimem serum free culture medium (Invitrogen, Breda, The Netherlands) before use. Freshly purified erythrocytes and platelets (provided by the Blood Cell Research Department of Sanquin) were obtained from two different anonymous donors. These cells were also resuspended in Optimem after being washed 3 times. In addition, platelets were supplemented with 10 mM glucose.

The exchange of IgG4 half molecules was evaluated and compared to the exchange of IgG1 half molecules. The following antibodies mixtures were prepared in PBS:

Bet v 1 specific IgG4 (10 μg) and Fel d 1 specific IgG4 (10 μg)

Bet v 1 specific IgG1 (10 μg) and Fel d 1 specific IgG1 (10 μg)

These antibody mixtures were incubated with $1.8 \times 10^4$ MNCs, $4.0 \times 10^8$ erythrocytes or $3.5 \times 10^4$ platelets in a total volume of 100 μl (final concentration for each antibody was 0.1 μg/ml) on a horizontal orbital shaker (125 rpm) at 37° C. After 48 h the incubation mixtures were centrifuged for 1 min at 2800 rpm in an Eppendorf centrifuge, after which a sample of 10 μl was drawn in 500 μl PBS-AT (PBS supplemented with 0.3% bovine serum albumin, 0.1% Tween-20 and 0.05% (w/v) NaN$_3$). Samples were stored, if necessary, at 4° C.

Bispecific activity (i.e. Fel d 1-Bet v 1 cross-linking activity) was measured in the heterologous cross-linking assay. In this assay, a sample was incubated for 24 h with 0.5 mg Sepharose-coupled recombinant Fel d 1 in a total volume of 300 μl in PBS-IAT (PBS-AT supplemented with 1 μg/ml IVIg). Subsequently, the Sepharose was washed with PBS-T and incubated for 24 h with $^{125}$I-labeled Bet v 1, after which the Sepharose was washed with PBS-T and the amount of radioactivity bound relative to the amount of radioactivity added was measured.

In FIG. 6 bispecific activity is shown as percentage bound $^{125}$I-labeled Bet v 1, which was determined in the heterologous cross-linking assay. All three cell types were able to induce bispecific activity. Some bispecific activity was also observed in Optimem serum free medium, but this activity was much lower than observed in the presence of blood cells. None of the tested cells was able to exchange IgG1 half molecules.

Example 27: Evaluation of IgG4 Fab Arm Exchange by Human and Murine Cell Lines

Chimeric IgG4 antibodies were mixed and subsequently incubated with three different cell lines (i.e. Human Embryo Kidney (HEK) cells, murine B cells or hybridomas) to investigate IgG4 exchange activity.

Cell line 3558 (provided by the Antigen Presentation Research Group of Sanquin) was chosen as a source of murine B cells. Hybridomas, which produce an anti-C1 esterase inhibitor, were obtained from the Autoimmune Research Group of Sanquin. Suspension HEK (293F) cells were from Invitrogen, Breda, The Netherlands. All cells were washed three times with PBS, after which the cells were resuspended in PBS.

The exchange of IgG4 half molecules was evaluated by incubating an IgG4 antibody mixture consisting of Bet v 1 specific IgG4 (2 μg) and Fel d 1 specific IgG4 (2 μg) with the aforementioned cells. The antibody mixture was incubated with $24 \times 10^5$ HEK cells, $25 \times 10^5$ murine B cells or $21 \times 10^5$ hybridomas in a total volume of 50 μl (final concentration for each antibody was 80 μg/ml) on a horizontal orbital shaker (125 rpm) at 37° C. After 0 h and 24 h the incubation mixtures were centrifuged for 1 min at 2800 rpm in an Eppendorf centrifuge, after which a sample was drawn in PBS-AT (PBS supplemented with 0.3% bovine serum albumin, 0.1% Tween-20 and 0.05% (w/v) NaN$_3$). Samples were stored, if necessary, at 4° C.

Bispecific activity (i.e. Fel d 1-Bet v 1 cross-linking activity) was measured in the heterologous cross-linking assay. In this assay, sample dilutions were incubated for 24h with 0.5 mg Sepharose-coupled recombinant Fel d 1 in a total volume of 300 μl in PBS-IAT (PBS-AT supplemented with 1 μg/ml IVIg). Subsequently, the Sepha rose was washed with PBS-T and incubated for 24 h with $^{125}$I-labeled Bet v 1, after which the Sepharose was washed with PBS-T and the amount of radioactivity bound relative to the amount of radioactivity added was measured.

In FIG. 7 bispecific activity is shown as percentage bound $^{125}$I-labeled Bet v 1, which was determined in the heterologous cross-linking assay. All three cell types were able to exchange IgG4 half molecules.

Example 28: Evaluation of IgG4 Fab Arm Exchange by Erythrocytes

Chimeric antibodies were mixed and subsequently incubated with human erythrocytes to investigate the exchange of IgG4 half molecules. Erythrocytes were purified from a single donor and stored at 4° C. in SAGM (Saline Adenine Glucose Mannitol) buffer. Before use the cells were washed three times with PBS.

In this experiment the exchange of IgG4 half molecules was compared with the exchange of IgG1. Also, the exchange of IgG4 in the presence of excess irrelevant IgG4 was evaluated. The following antibodies mixtures were prepared in PBS:

Bet v 1 specific IgG4 (4 μg) and Fel d 1 specific IgG4 (4 μg)

Bet v 1 specific IgG1 (4 μg) and Fel d 1 specific IgG1 (4 μg)

Bet v 1 specific IgG4 (4 μg), Fel d 1 specific IgG4 (4 μg) and irrelevant IgG4 specific for antigen X (80 μg)

These mixtures were incubated with erythrocytes in PBS supplemented with 0.05% (w/v) NaN$_3$ in a total volume of 100 μl (final hematocrit was around ~40%) and subsequently incubated on a horizontal orbital shaker (125 rpm) at 37° C. At indicated time points the erythrocytes were centrifuged for 1 min at 2800 rpm in an Eppendorf centrifuge, after which a sample of 10 μl was drawn in 500 μl PBS-AT (PBS supplemented with 0.3% bovine serum albumin, 0.1% Tween-20 and 0.05% (w/v) NaN$_3$). Samples were stored at 4° C. before measuring bispecific activity, bivalency and antigen binding. As a control the same mixtures were also incubated in PBS without erythrocytes.

Levels of Bet v 1 binding antibodies were measured in the antigen binding test. To this end, samples were incubated with 0.75 mg of protein G Sepharose (Amersham Biosciences, Uppsala, Sweden) in 750 μl PBS-IAT (PBS-AT supplemented with 1 μg/ml IVIg) in the presence of $^{125}$I-labeled Bet v 1 for 24h. Next, the Sepharose was washed with PBS-T (PBS supplemented with 0.1% Tween-20 and 0.05% (w/v) NaN$_3$) and the amount of radioactivity bound relative to the amount of radioactivity added was measured. The concentration of Bet v 1 specific IgG was calculated using purified Bet v 1 specific antibodies as a standard (range 0-200 ng per test as determined by nephelometer). Bispecific activity in experiments using Fel d 1 and Bet v 1 specific antibodies was measured in the Feld1-Betv1 cross-linking assay. In this assay, IgG containing sample was incubated for 24 h with Sepharose-coupled cat extract (0.5 mg) in a total volume of 300 μl in PBS-AT. Subsequently, the Sepharose was washed with PBS-T and incubated for 24 h with $^{125}$I-labeled Bet v 1, after which the Sepharose was washed with PBS-T and the amount of radioactivity bound relative to the amount of radioactivity added was measured. The concentration of bispecific IgG (Feld1-Betv1) was calculated using purified IgG1-Betv1 as a standard (obtained in Bet v 1 binding test using Prot G sepharose).

In FIG. 8 data obtained from the erythrocyte-mediated exchange are presented. No exchange of IgG1 half molecules was observed in the presence of erythocytes, whereas about maximum exchange of IgG4 half molecules was observed after 72 h (panel A) (note: if equal amounts of IgG4-Betv1 and IgG4-Feld1 are exchanged, at most 50% of the IgG4-Betv1 half-antibodies will be incorporated in the bispecific fraction after random and complete exchange of half molecules). In the presence of excess irrelevant IgG4 almost no exchange of IgG4 half molecules was measured, which is in line with the expected exchange of Bet v 1 and Fel d 1 specific IgG4 with irrelevant IgG4. Size-exclusion chromatography was performed to exclude the possibility that bispecific activity observed in the IgG4 mix was the result of IgG aggregation. For this purpose, a sample (drawn at t=72h) was fractionated on a Superdex200 column, after which Fel d 1 binding IgG and Bet v 1-Fel d 1 cross-linking IgG were measured in the fractions. Fel d 1 binding antibodies eluted in one peak with a retention volume of ~12.9 ml, which corresponds to the retention volume of monomeric IgG. The heterologous Bet v 1-Fel d 1 cross-linking activity was detected in the same fractions indicating that bispecific activity was associated with monomeric IgG (data not shown).

In theory, the exchange of IgG4 half molecules is also associated with a decrease in bivalency. To test this, bivalency in the incubation mixtures was measured. Almost no reduction of Fel d 1 bivalency was observed in the IgG1 mix, whereas a reduction of ~50% was observed in the IgG4 mix. This reduction is in agreement with the maximal exchange of two different IgG4 molecules mixed in a 1 to 1 ratio. As expected, the reduction of bivalency in the IgG4 mix with excess irrelevant IgG4 was higher (~80%), which is due to the low probability of rehybridisation of two homologous half molecules (Bet v 1 or Fel dl specific) in the presence of excess irrelevant IgG4 half molecules. The strong reduction in bivalency was not the result of loss of antigen binding during the incubation, because the antigen binding was only slightly (~10%) decreased after 72 h of incubation (data not shown).

The exchange of IgG in PBS (supplemented with 0.05% (w/v) NaN$_3$) was also evaluated to investigate whether IgG4 half molecules can be exchanged spontaneously. The set-up of this experiment was similar to the exchange in the presence of erythrocytes with the exception that no erythrocytes were added. No spontaneous exchange of IgG1 or IgG4 half molecules was observed during the incubation in PBS at 37° C. as is demonstrated FIG. 9A. However, some background was observed in the IgG4 mix, which was also present during the incubation with erythrocytes. No decrease of bivalency was observed during the incubation in PBS (FIG. 9B).

Example 29: Evaluation of IgG4 Fab Arm Exchange by Erythrocyte Lysate

Chimeric IgG4 antibodies were mixed and subsequently incubated with increasing dilutions of erythrocyte lysate. Erythrocytes were isolated from a healthy donor and stored at 4° C. in SAGM (Saline Adenine Glucose Mannitol) buffer with a hematocrit of 60.7%. To obtain lysate the cells were washed three times with PBS-Azide (PBS supplemented with 0.05% (w/v) NaN$_3$) and resuspended in water with a volume that was two fold higher than the volume of the storage buffer. As a result, undiluted erythrocyte lysate was equivalent to a hematocrit of 30%.

The exchange of IgG4 half molecules was evaluated by incubating an IgG4 antibody mixture consisting of Bet v 1 specific IgG4 (1 μg) and Fel d 1 specific IgG4 (1 μg) with 50 μl of freshly prepared lysate (supplemented with PBS/Azide to a total volume of 100 μl) at 37° C. Final concentration of each antibody was 10 μg/ml. At indicated time points a sample was drawn from the incubation mix in PBS-AT (PBS supplemented with 0.3% bovine serum albumin, 0.1% Tween-20 and 0.05% (w/v) NaN$_3$) to measure bispecific activity. Samples were stored, if necessary, at 4° C.

Bispecific activity (i.e. Bet v 1-Fel d 1 cross-linking activity) was measured in the heterologous cross-linking assay. In this assay, sample dilutions were incubated for 24h with 0.5 mg Sepharose-coupled birch extract in a total volume of 300 μl in PBS-IAT (PBS-AT supplemented with 1 μg/ml IVIg). Subsequently, the Sepharose was washed with PBS-T and incubated for 24 h with $^{125}$I-labeled Fel d 1, after which the Sepharose was washed with PBS-T and the amount of radioactivity bound relative to the amount of radioactivity added was measured. The concentration of bispecific IgG (Bet v 1-Fel d 1) was calculated using the calibration curve of the Fel d 1 binding test, which was obtained from purified Fel d 1 binding rIgG.

In FIG. 10 generation of bispecific activity in time is shown as percentage bound $^{125}$I-labeled Fel d 1, which was determined in the heterologous cross-linking assay. From these data it is evident that lysate of erythrocytes contains exchange activity. Highest exchange rate was observed in undiluted lysate, whereas higher dilutions resulted in lower exchange rates. Practically no bispecific activity was observed in the control incubation in PBS.

Size-exclusion chromatography was performed to exclude the possibility that bispecific activity induced by erythrocyte lysate was the result of IgG aggregation (FIG. 11). For this purpose, an incubation mixture was prepared consisting of 10 µg Bet v 1 binding IgG4, 10 µg Fel d 1 binding IgG4 and 50 µl erythrocyte lysate, which was supplemented with PBS/Azide to final volume of 100 µl. This mixture was incubated at 37° C. for 24 h, after which 70 µl was fractionated on a Superdex200 column. In the fractions Bet v 1 binding IgG and Fel d 1-Bet v 1 cross-linking IgG were measured. Levels of Bet v 1 binding antibodies were measured in the antigen binding test. Samples were incubated with 0.75 mg of protein G Sepharose (Amersham Biosciences, Uppsala, Sweden) in 750 µl PBS-IAT (PBS supplemented with 1 µg/ml IVIg, 0.3% bovine serum albumin, 0.1% Tween-20 and 0.05% (w/v) NaN$_3$) in the presence of $^{125}$I-labeled Bet v 1 for 24h. Next, the Sepharose was washed with PBS-T (PBS supplemented with 0.1% Tween-20 and 0.05% (w/v) NaN$_3$) and the amount of radioactivity bound relative to the amount of radioactivity added was measured. The concentration of Bet v 1 specific IgG was calculated using purified Bet v 1 specific antibodies as a standard (range 0-200 ng per test as determined by nephelometer). The concentration of bispecific IgG (i.e. Fel d 1-Bet v 1 cross-linking activity) was measured in the heterologous cross-linking assay. In this assay, a sample was incubated for 24 h with 0.5 mg Sepharose-coupled cat extract, in which Fel d 1 antigen is present, in a total volume of 300 µl in PBS-IAT. Subsequently, the Sepharose was washed with PBS-T and incubated for 24 h with $^{125}$I-labeled Bet v 1, after which the Sepharose was washed with PBS-T and the amount of radioactivity bound relative to the amount of radioactivity added was measured. The concentration of bispecific IgG (Fel d 1-Bet v 1) was calculated using the same calibration curve as used in the Bet v 1 binding test, which was obtained from purified Bet v 1 binding rIgG.

Bet v 1 binding antibodies eluted in one peak with a retention volume of ~12.6 ml, which corresponds to the retention volume of monomeric IgG (FIG. 11). The heterologous Fel d 1-Bet v 1 cross-linking activity was detected in the same fractions indicating that bispecific activity was associated with monomeric IgG.

Example 30: Evaluation of IgG4 Fab Arm Exchange Activity in Dialyzed Erythrocyte Lysate Erythrocytes were isolated from a healthy donor and stored at 4° C. in SAGM (Saline Adenine Glucose Mannitol) buffer with a hematocrit of 60.7%. To obtain lysate the cells were washed three times with PBS-Azide (PBS supplemented with 0.05% (w/v) NaN$_3$) and resuspended in water with a volume that was two-fold higher than the volume of the storage buffer. Therefore, undiluted erythrocyte lysate was equivalent to a hematocrit of 30%. Part of the lysate was dialyzed against PBS-Azide using a dialysis membrane cassette from Pierce (3.5 kD cut-off). Ultrafiltrate was obtained by centrifugation of non-dialyzed lysate in an Amicon filter (3.5 kD cut-off).

The exchange of IgG4 half molecules was evaluated by incubating an IgG4 antibody mixture (Bet v 1 specific IgG4 (0.5 µg) and Fel d 1 specific IgG4 (0.5 µg) with freshly prepared erythrocyte lysate (25 µl) or dialyzed lysate (25 µl) at 37° C. Total volume of each incubation was 50 µl resulting in a final concentration of 10 µg/ml for each antibody. The following supplements were used: reduced glutathione (GSH) from Sigma, Glucose-6-phosphate (G-6-P) and NADPH (both from Roche). These compounds were dissolved in water before use. After 24 h of incubation a sample was drawn from the incubation mix in PBS-AT (PBS supplemented with 0.3% bovine serum albumin, 0.1% Tween-20 and 0.05% (w/v) NaN$_3$) to measure bispecific activity. Samples were stored, if necessary, at 4° C.

Bispecific activity (i.e. Fel d 1-Bet v 1 cross-linking activity) was measured in the heterologous cross-linking assay. In this assay, sample dilutions were incubated for 24h with 0.5 mg Sepharose-coupled cat extract in a total volume of 300 µl in PBS-IAT (PBS-AT supplemented with 1 µg/ml IVIg). Subsequently, the Sepharose was washed with PBS-T and incubated for 24 h with $^{125}$I-labeled Bet v 1, after which the Sepharose was washed with PBS-T and the amount of radioactivity bound relative to the amount of radioactivity added was measured.

The exchange levels were compared with the bispecific activity generated by freshly prepared lysate (Table 2).

TABLE 2

Overview of factors that restore bispecific activity in dialyzed erythrocyte lists. Exchange activity of dialyzed erythrocyte lysate was compared with freshly prepared lysate. Dialyzed lysate was supplemented with 5 □l of ultrafiltrate. Final concentrations of G-6-P, NADPH and GSH were 5 mM, 0.1 mM and 0.5 mM, respectively.

| Exchange source | Supplement | Exchange activity |
| --- | --- | --- |
| Lysate | — | ++ |
| Dialyzed lysate | — | − |
| Dialyzed lysate | Ultrafiltrate | + |
| Dialyzed lysate | G-6-P, NADPH, GSH | ++ |
| Dialyzed lysate | G-6-P | − |
| Dialyzed lysate | NADPH | − |
| Dialyzed lysate | GSH | ++ |

From these data it is evident that the activity of erythrocyte lysate was lost after dialysis. Addition of ultrafiltrate restored the exchange for a large part. This result suggested that during dialysis a component (<3.5 kD) was lost, which is essential for the exchange reaction. Such a component is likely to be involved in the redox cycle, because disulfide bridge reduction and oxidation is required for the exchange of IgG4 half molecules. Therefore, three "co-factors" (G-6-P, NADPH and GSH) of the redox cycle were added to dialyzed lysate to investigate whether these compounds could restore the exchange activity. The exchange activity could be restored if G-6-P, NADPH and GSH were supplemented together. Incubation of dialyzed lysate in the presence of separate factors revealed that the exchange activity was restored by GSH, but not by G-6-P or NADPH.

Example 31: Evaluation of IgG4 Half Molecule Exchange by Reduced Glutathione

Chimeric antibodies were mixed and subsequently incubated with reduced glutathione (GSH) to investigate the exchange of IgG4 half molecules. GSH (Sigma-Aldrich, St. Louis, Mo.) was solved in water before use.

In this experiment the exchange of IgG4 half molecules was evaluated by incubating an IgG4 antibody mixture consisting of Bet v 1 specific IgG4 (1 µg) and Fel d 1 specific IgG4 (1 µg) in PBS/Azide containing GSH at 37° C. Total incubation volume was 100 µl resulting in a final concentration of 10 µg/ml for each antibody. At indicated time points a sample was drawn from the incubation mixture in PBS-AT (PBS supplemented with 0.3% bovine serum albumin, 0.1% Tween-20 and 0.05% (w/v) $NaN_3$). Samples were stored at 4° C. for measuring of antigen binding and bispecific activity Levels of Bet v 1 binding antibodies were measured in the antigen binding test. Samples were incubated with 0.75 mg of protein G Sepharose (Amersham Biosciences, Uppsala, Sweden) in 750 µl PBS-IAT (PBS-AT supplemented with 1 µg/ml IVIg) in the presence of $^{125}$I-labeled Bet v 1 for 24h. Next, the Sepharose was washed with PBS-T (PBS supplemented with 0.1% Tween-20 and 0.05% (w/v) $NaN_3$) and the amount of radioactivity bound relative to the amount of radioactivity added was measured. The concentration of Bet v 1 specific IgG was calculated using purified Bet v 1 specific antibodies as a standard (range 0-200 ng per test as determined by nephelometer). The concentration of bispecific IgG (i.e. Fel d 1-Bet v 1 cross-linking activity) was measured in the heterologous cross-linking assay. In this assay, a sample was incubated for 24 h with 0.5 mg Sepharose-coupled cat extract, in which Fel d 1 antigen is present, in a total volume of 300 µl in PBS-IAT. Subsequently, the Sepharose was washed with PBS-T and incubated for 24 h with $^{125}$I-labeled Bet v 1, after which the Sepharose was washed with PBS-T and the amount of radioactivity bound relative to the amount of radioactivity added was measured. The concentration of bispecific IgG (Fel d 1-Bet v 1) was calculated using the same calibration curve as used in the Bet v 1 binding test, which was obtained from purified Bet v 1 binding IgG.

In FIG. 12 time courses of GSH mediated exchange of IgG4 half molecules are presented. From these data it is clear that IgG4 half molecules are exchanged in the presence of GSH. In this experiment optimal exchange was observed between 0.1 and 1 mM GSH and highest exchange (~90%) was reached after 24 h using 0.5 mM GSH.

Size-exclusion chromatography was performed to exclude the possibility that bispecific activity observed after GSH mediated exchange of IgG4 was the result of IgG aggregation (FIG. 13). For this purpose, a mixture of Bet v 1 binding IgG and Fel d 1 binding IgG (10 µg of each antibody) was incubated with 0.5 mM GSH in PBS/Azide. This mixture (final volume 100 µl) was incubated at 37° C. for 24 h, after which 70 µl was fractionated on a Superdex200 column. In the fractions Bet v 1 binding IgG and Fel d 1-Bet v 1 cross-linking IgG were measured. Bet v 1 binding antibodies eluted in one peak with a retention volume of ~12.6 ml, which corresponds to the retention volume of monomeric IgG. The heterologous Fel d 1-Bet v 1 cross-linking activity was detected in the same fractions indicating that bispecific activity was associated with monomeric IgG. The generation of bispecific IgG4 molecules in the presence of GSH was found to be temperature dependent, as exchange occurred more efficiently at 37° C. than at 4° C. (FIG. 14).

Example 32. Generation of Bispecific IgG in the Presence of Other Agents

IgG1-Betv1 and IgG1-Feld1 or IgG4-Betv1 and IgG4-Feld1 were mixed at a final concentration of 10 µg/ml for antibody and incubated with reducing agents in a total volume of 50 µl. Apart from GSH the following agents were tested (final concentration in incubation mixture): L-cysteine was from Sigma (100 µM), dithiothreitol (DTT) was from Biorad (50 µM), β-mercapto-ethanol (BME) was from Biorad (100 µM) and oxidized glutathione (GSSG, note that of the panel of agents this agent is not reducing, while all others are) was from Sigma (100 µM). The mixtures were incubated at 37° C. for 24 h and samples were drawn in PBS/AT, in which the (bi)specific IgG concentrations were measured. FIG. 15 shows that the addition of GSH or other reducing agents (but not of GSSG) to a mixture of purified IgG4-Betv1 and IgG4-Feld1 was sufficient to induce Fab arm exchange and the generation of bispecific IgG4. In contrast, no bispecific reactivity was induced in the control IgG1 mixture.

Example 33. Exchange of Fully Human IgG4 Antibodies Using GSH

IgG1-CD20, IgG4-CD20, IgG1-EGFr and IgG4-EGFr were mixed and incubated with GSH in a total volume of 1 ml. Final concentration of each antibody was 50 µg/ml; the final concentration of GSH was 0.5 mM. The mixtures were incubated at 37° C. for 24 h and samples were drawn in PBS-AT, in which the (bi)specific IgG concentrations were measured.

Bispecific activity was determined using a sandwich ELISA. For this assay an ELISA plate (Greiner bio-one, Frickenhausen, Germany) was coated overnight with 1 µg/ml (100 µl/well) of recombinant extracellular domain of EGFR in PBS at 4° C. The plate was washed 3 times with PBS/0.05% Tween 20 (PBT). Samples were diluted in PBT/0.2 BSA (PBTB) and transferred to the ELISA plate (100 µl/well). After incubation on a plate shaker (300 rpm) for 90 minutes at room temperature (RT), samples were discarded and the plate was washed 3 times with PBT. Next, 100 µl of the mouse anti-idiotypic monoclonal antibody 2F2 SAB1.1 (directed against the anti-CD20 antibody 7D8; Genmab) at 2 µg/ml in PBTB was added and incubated at RT for 90 minutes at a plate shaker (300 rpm). The anti-idiotypic antibody was discarded and the plate was washed 3 times with PBT, followed by the addition of 100 µl/well of a HRP conjugated goat anti-mouse IgG (Jackson ImmunoResearch Laboratories, Westgrove, Pa., USA) at a 1000× dilution in PBTB and incubation at RT for 90 minutes at a plate shaker (300 rpm). The detection antibody was discarded and the plate was washed 3 times with PBT. A 50 mg ABTS tablet (Roche Diagnostics GmbH, Mannheim, Germany) was dissolved in ABTS buffer (Roche) and added to the ELISA plate (100 µl/well). The ELISA plate was incubated for 30 min (or longer if desired) at RT on a plate shaker (300 rpm) covered with aluminum foil and the reaction was stopped with 100 µl oxalic acid (Riedel de Haen Seelze, Germany) per well. The ELISA plate was left at RT for 10 minutes before reading absorbance at 405 nm in an ELISA plate reader.

FIG. 16A shows that bispecific anti-EGFR/CD20 antibodies formed in time upon incubation of the mixture of IgG4-EGFr and IgG4-CD20 in the presence, but not in the absence, of GSH. Fab arm exchange did not occur in a mixture of IgG1 antibodies, neither in the presence or absence of GSH.

To explore the dynamic range of GSH mediated exchange of IgG4 half molecules, a full concentration curve of GSH (0.5-1,000 µM) was used to analyze exchange. IgG4-CD20 and IgG4-EGFr were mixed and incubated with GSH in a total volume of 1 ml. Final concentration of each antibody was 50 µg/ml; the final concentration of GSH were as indicated in FIG. 16B. The mixtures were incubated at 37° C. for 24 h and samples were drawn in PBS-AT, in which the (bi)specific IgG concentrations were measured.

FIG. 16B shows a clear GSH-dose dependence of IgG4 half molecule exchange. To explore how reaction components influence the GSH-mediated IgG4 half molecule exchange, exchange was tested in PBS and serum- and protein free, chemically defined medium (FreeStyle 293 expression medium, GIBCO/Invitrogen Corporation). It was found that in this tissue culture medium, GSH-mediated exchange occurs at lower GSH-concentrations (FIG. 16C). It was also found that there is an optimum in GSH-mediated IgG4 half molecule exchange, as incubation with 5 mM GSH clearly resulted in lower exchange that with 0.5 mM GSH (FIG. 16D).

A mixture of IgG4-EGFr and IgG4-CD20 was incubated for 24 h in the absence or presence of GSH and evaluated by mass spectrometry (ESI-TOF MS). Fifty µl samples containing 200 µg/ml of each antibody were deglycosylated overnight with 1 µl N-glycosidase F (Roche Diagnostics NL BV, Almere, The Netherlands). Samples were desalted on an Acquity UPLC™ (Waters, Milford, USA) with a BEH C8, 1.7 µm, 2.1×50 mm column at 60° C. Five µl was injected and eluted with a gradient from 5% to 95% eluent B. Eluent A was MilliQ water (Millipore Synthesis A10 apparatus) and eluent B was LC-MS grade acetonitrile (Biosolve, Valkenswaard, The Netherlands). Both eluents contained 0.05% formic acid as organic modifier (Fluka Riedel-de Haên, Buchs, Germany). Time-of-flight electrospray ionization mass spectra were recorded on-line on a micrOTOF™ mass spectrometer (Bruker, Bremen, Germany) operating in the positive ion mode. In each analysis, a 500-5000 m/z scale was internally calibrated with ES tuning mix (Agilent Technologies, Santa Clara, USA). Mass spectra were deconvoluted by using the Maximum Entropy algorithm, which is provided with DataAnalysis™ software v. 3.3 (Bruker).

FIG. 16E shows that the molecular weights of IgG4-CD20 (145.5 kD) and IgG4-EGFR (145.9 kD) remained unchanged in the absence of GSH. In the presence of GSH (FIG. 16F), however, a new peak with a mass corresponding to a Fab arm exchanged molecule appeared (145.7 kD). The novel mass corresponded to the expected mass of the bispecific anti-EGFR/CD20 antibody. Moreover, from the peak heights of the MS spectra it could be estimated that the bispecific antibody represented 50% of the total antibody mass in the mixture indicating a random exchange which reached equilibrium within 24 hours.

Example 34. Rhesus Monkey IVIg Participates in Fab Arm Exchange of Recombinant Human IgG4 Antibodies Mixtures of two recombinant human IgG4 antibodies (IgG4-CD20 and IgG4-EGFr, as described above) were incubated with GSH for 24 h at 37° C., in the presence or absence of rhesus monkey or human IVIg. The formation of bispecific antibodies through Fab arm exchange was measured in a sandwich ELISA as described above.

FIG. 17 shows that monkey polyclonal IVIg compares to human polyclonal IVIg in its ability to inhibit the exchange of Fab arms of the recombinant antibodies in vitro in the presence of reduced glutathione. This means that a component of rhesus IVIg, rhesus immunoglobulin, participates in Fab arm exchange. Rhesus immunoglobulin, presumably rhesus IgG4, can exchange Fab arm with recombinant human IgG4.

Example 35. Fab Arm Exchange of Hinge Region or CH3 Domain Mutants

Three IgG1 mutants were made: an IgG1 with an IgG4 core-hinge (IgG1-CPSC) and two CH3 domain swap mutants (IgG1-CH3(IgG4) and IgG1-CPSC-CH3(IgG4)).

All references to CPSC in Example 35 refer to SEQ ID NO:51.

Site directed mutagenesis was used to introduce a P228S mutation in the hinge of IgG1 using pEE-G1-wt a Bet v 1 as a template. Mutagenic primers, forward and reverse, were designed with Vector NTI Advance 10:

```
P228S Mut primer-F: SEQ ID NO: 23:
cttgtgacaa aactcacacc tgcccatcgt gcccaggtaa gccag P228S Mut primer-R: SEQ ID NO: 24:
ctggcttacc tgggcacgat gggcaggtgt gagttttgtc acaag
```

Quickchange site-directed mutagenesis kit (Stratagene) was used to create the pEE-G1-CPSC mutant. The polymerase chain reaction (PCR) mix consisted of 5 µl pEE-G1 a Betv1 DNA template (~35 ng), 1, 5 µl mutagenic primer-forward (~150 ng), 1.5 µl mutagenic primer-reverse (~150 ng), 1 µl dNTP mix, 5 µl reaction buffer (10×), 36 µl H2O and finally 1 µl Pfu Turbo DNA polymerase. Then the mix was applied to the PCR: 30" 95° C., 30" 95° C. (denaturating), 1' 55° C. (annealing) and 17 minutes 68° C. (elongating). This cycle was repeated 20 times.

DNA digesting and ligation was used to create CH3 domain swap mutant constructs IgG1-CH3(IgG4) and IgG1-CPSC-CH3(IgG4). Digestion reactions to obtain CH3 domains and vectors without CH3 domains were as follows: ~1500 ng DNA (pEE-G1-betv1, pEE-G1-CPSC and pEE-G4-betv1), 2 µl BSA, 2 µl Neb3 buffer, 1 µl SalI and H2O added to a volume of 20 µl. Incubation at 37° C. for 30'. DNA was purified and eluted with 30 µl H2O before 1 µl SanDI and 3 µl universal buffer was added and incubated at 37° C. for 30'. Fragments were subjected to gel electrophoresis on 1% agarose gels with ethidium bromide. Fragments were cut from the gel under ultraviolet light and dissolved using a DNA purification kit (Amersham). The pEE-G4-wt SalI/SanDI (which contained IgG4 CH3 domain) fragment was ligated into pEE-G1-wt and pEE-G1-CPSC using following procedure: 1 µl template DNA (SalI/SanDI digested pEE-G1-wt and pEE-G1-CPSC), 5 µl SalI/SanDI insert, 4 µl Ligate-it buffer, 9 µl H2O and 1 µl ligase in a total volume of 20 µl. Ligation was stopped after 5'.

DNA digestion (using ApaI and HindIII) and ligation was used to replace the VH domain of the bet v 1 mutant antibodies with that of pEE-G4-a-feld1 wt, following a similar procedure as above.

Also, one IgG4 mutant was made: IgG4-S228Pnew. In this mutant, the hinge is stabilized by replacing serine at position 228 for a proline (IgG1 core hinge). Site-directed mutagenesis was performed using the QuickChange II XL Site-Directed Mutagenesis Kit (Stratagene, Amsterdam, The Netherlands) according to the manufacturer's instructions. This method included the introduction of a silent extra XmaI site to screen for successful mutagenesis. Briefly, 5 µl 10× reaction buffer, 1 µl oligonucleotide S228Pfcorrect (100 pmol/µl), 1 µl oligonucleotide S228Prcorrect (100 pmol/µl), 1 µl dNTP mix, 3 µl Quicksolution, 1 µl plasmid pTomG42F8HG (50 ng/µl) (described in PCT application entitled "Recombinant monovalent antibodies and methods for production thereof", filed on 28 Nov. 2006 (RO/DK (Genmab)) and 1 µl PfuUltra HF DNA polymerase were mixed in a total volume of 50 µl and amplified with a TGradient Thermocycler 96 (Whatman Biometra, Goettingen, Germany; product #050-801) using an 18-cycle program: denaturing at 95° C. for 1 min; 18 cycles of 95° C. for 50 sec, 60° C. for 50 sec, and 68° C. for 10 min. PCR mixtures were stored at 4° C. until further processing. Next, PCR mixtures were incubated with 1 µl DpnI for 60 min at 37° C. to digest the pTomG42F8HG vector and stored at 4° C. until further processing. The reaction mixture was precipitated with 5 µl 3 M NaAc and 125 µl Ethanol, incubated for 20 minutes at −20° C. and spun down for 20 minutes at 4° C. at 14000×g. The DNA pellet was washed with 70% ethanol, dried and dissolved in 4 µl water. The total 4 µl reaction volume was transformed in One Shot DNH5α T1R competent *E. coli* cells (Invitrogen, Breda, The Netherlands) according to the manufacturer's instructions (Invitrogen). Next, cells were plated on Luria-Bertani (LB) agar plates containing 50 µg/ml ampicillin. Plates were incubated for 16-18 hours at 37° C. until bacterial colonies became evident.

After screening by colony PCR and XmaI (mutagenesis will result in the loss of a XmaI site) digestion, plasmid was isolated from the bacteria and the mutation was confirmed by DNA sequencing. To check if no unwanted extra mutations were introduced the whole HC coding region was sequenced and did not contain any additional mutations. The final construct was named pTomG42F8S228PNew.

| Name | Oligonucleotide Sequence |
|---|---|
| S228Pfcorrect (SEQ ID NO: 21) | CCCCCATGCCCACCATGCCCAGGTAAGCCAACCC AGGCCTCGC |
| S228Prcorrect (SEQ ID NO: 22) | GCGAGGCCTGGGTTGGCTTACCTGGGCATGGTGG GCATGGGGG |

Recombinant antibodies from these constructs were transiently expressed in HEK 293 cells in 3 ml, 6-wells plates (NUNC) or in 125 ml erlenmeyers (Corning) with 293 Fectin (Invitrogen) as transfection reagent.

The following mixtures of unpurified antibodies (FreeStyle 293 expression medium, GIBCO/Invitrogen Corporation) were incubated with 0.1 mM GSH at 37° C. for 24 h and samples were drawn in PBS-AT, in which the (bi) specific IgG concentrations were measured as described in previous examples:

IgG4 anti-feld1 wt with IgG4 anti-betv1 wt
IgG1 anti-feld1 wt with IgG4 anti-betv1 wt
IgG1 anti-feld1 CPSC with IgG1 anti-betv1 CPSC (indicated as IgG1 CPSC-IgG1 CPSC below)
IgG1 anti-feld1 CPSC with IgG1 anti-betv1 CH3(IgG4) (IgG1 CPSC-IgG1 CH3(IgG4))
IgG1 anti-feld1 CPSC with IgG1 anti-betv1 CPSC/CH3 (IgG4) (IgG1 CPSC-IgG1 CPSC/CH3(IgG4))
IgG1 anti-feld1 CH3(IgG4) with IgG1 anti-betv1 CH3 (IgG4) (IgG1 CH3(IgG4)-IgG1 CH3(IgG4))
IgG1 anti-feld1 CH3(IgG4) with IgG1 anti-betv1 CPSC/ CH3(IgG4) (IgG1 CH3(IgG4)-IgG1 CPSC/CH3 (IgG4))-IgG1 anti-feld1 CPSC/CH3(IgG4) with antibetv1 IgG1 CPSC/CH3(IgG4) (IgG1 CPSC/CH3 (IgG4)-IgG1 CPSC/CH3(IgG4))
IgG1 anti-feld1 CPSC/CH3(IgG4) with IgG4-antibetv1 wt (IgG1 CPSC/CH3(IgG4)-IgG4 wt)

IgG4 anti-bet1 S228Pnew with IgG4 wt

The results showed that under these in vitro conditions (0.1 mM GSH), half molecule exchange occurs when one of the antibodies contains the CPSC hinge (SEQ ID NO:51) and both antibodies contain an IgG4-like CH3. Also, half molecule exchange occurs between an IgG4 molecule containing an IgG1 hinge and IgG4 wt molecules:

|  | IgG1 wt | IgG4 wt | IgG1 CH3(IgG4) | IgG1 CPSC | IgG1 CPSC/ CH3(IgG4) |
|---|---|---|---|---|---|
| IgG1 wt | − | − | | | |
| IgG4 wt | − | + | + | − | + |
| IgG1 CH3(IgG4) | | + | − | − | ± |
| IgG1 CPSC | − | − | − | − | |
| IgG1 CPSC/CH3(IgG4) | | + | ± | − | + |
| IgG4 S228Pnew | − | + | | | |

− = no exchange
+ = exchange occurs
± = limited exchange (~5%)
Blank square = not tested The effect of GSH concentration on the half molecule exchange from the different mutants was tested using 0, 0.1, 1 and 10 mM GSH. Exchange was tested using the following mixtures:

IgG4 a-feld1 wt with IgG4 a-betv1 wt
IgG1 a-feld1 wt with IgG4 a-betv1 wt
IgG1 a-feld1 CPSC with IgG1 a-betv1 CPSC
IgG1 a-feld1 CH3(IgG4) with IgG1 a-betv1 CH3(IgG4)
IgG1 a-feld1 CPSC/CH3(IgG4) with a-betv1 IgG1 CPSC/ CH3(IgG4))

For GSH concentrations up to 1 mM, the results (FIG. 18) confirmed those described above. At 10 mM GSH, half molecule exchange was also seen in the reaction containing IgG1 a-feld1 CH3(IgG4) and IgG1 a-betv1 CH3(IgG4).

Size-exclusion chromatography was performed to exclude the possibility that bispecific activity observed after GSH mediated exchange of the appropriate IgG1 mutants was the result of IgG aggregation as described in previous examples. The heterologous Fel d 1-Bet v 1 cross-linking activity was detected in the fractions corresponding to the retention volume of monomeric IgG.

Example 36. Generation of IgG1 and IgG4 Antibodies with Hinge Region and/or CH3 Domain Mutations Five IgG1 mutants were made: an IgG1 with an IgG4 core-hinge (IgG1-P228S), two CH3 domain swap mutants (IgG1-CH3(γ4) and IgG1-P228S-CH3(γ4)), one CH3 point mutant in which lysine present at position 409 of IgG1 (within the CH3 domain) is replaced for arginine (IgG1-K409R), and one IgG1 with an IgG4 core hinge and K409R mutation (IgG1-P228S-K409R) (FIG. 19). These mutants were made with either Bet v 1 or Fel d 1 specificity.

Two IgG4 mutants were made: one CH3 point mutant in which arginine present at position 409 of IgG4 (within the CH3 domain) is replaced for lysine (IgG4-R409K), and one CH3 swap mutant (IgG4-CH3(γ1)) (FIG. 19). These were also made with either Bet v 1 or Fel d 1 specificity.

All references to CPSC in Example 36 refer to SEQ ID NO:51.

Site directed mutagenesis was used to introduce a P228S mutation in the hinge of IgG1 using pEE-G1-wt a Bet v 1 as a template. Mutagenic primers, forward and reverse, were designed with Vector NTI Advance 10:

P228S Mut primer-F: SEQ ID NO:23: cttgtgacaa aactcacacc tgcccatcgt gcccaggtaa gccag P228S Mut primer-R: SEQ ID NO:24: ctggcttacc tgggcacgat gggcaggtgt gagttttgtc acaag Quickchange site-directed mutagenesis kit (Stratagene) was used to create the pEE-G1-CPSC mutant. The polymerase chain reaction (PCR) mix consisted of 5 µl pEE-G1 a Betv1 DNA template (~35 ng), 1.5 µl mutagenic primer-forward (~150 ng), 1.5 µl mutagenic primer-reverse (~150 ng), 1 µl dNTP mix, 5 µl reaction buffer (10×), 36 µl H2O and finally 1 µl Pfu Turbo DNA polymerase. Then the mix was applied to the PCR: 30" 95° C., 30" 95° C. (denaturating), 1' 55° C. (annealing) and 17 minutes 68° C. (elongating). This cycle was repeated 20 times.

DNA digesting and ligation was used to create CH3 domain swap mutant constructs IgG1-CH3(γ4) and IgG1-P228S-CH3(γ4). Digestion reactions to obtain CH3 domains and vectors without CH3 domains were as follows: 1500 ng DNA (pEE-G1-betv1, pEE-G1-CPSC and pEE-G4-betv1), 2 µl BSA, 2 µl Neb3 buffer, 1 µl SalI and H2O added to a volume of 20 µl. Incubation at 37° C. for 30'. DNA was purified and eluted with 30 µl H2O before 1 µl SanDI and 3 µl universal buffer was added and incubated at 37° C. for 30'. Fragments were subjected to gel electrophoresis on 1% agarose gels with ethidium bromide. Fragments were cut from the gel under ultraviolet light and dissolved using a DNA purification kit (Amersham). The pEE-G4-wt SalI/SanDI (which contained IgG4 CH3 domain) fragment was ligated into pEE-G1-wt and pEE-G1-CPSC using following procedure: 1 µl template DNA (SalI/SanDI digested pEE-G1-wt and pEE-G1-CPSC), 5 µl SalI/SanDI insert, 4 µl Ligate-it buffer, 9 µl H2O and 1 µl ligase in a total volume of 20 µl. Ligation was stopped after 5'.

DNA digestion (using ApaI and HindIII) and ligation was used to replace the VH domain of the bet v 1 mutant antibodies with that of pEE-G4-a-feld1 wt, following a similar procedure as above.

Site-directed mutagenesis was used to introduce point mutations (K409R or R409K) into the pEE-γ4 wt, pEE-γ1 and PEE-γ1-P228S constructs. Mutagenic primers, forward and reverse, were designed with Vector NTI Advance 10:

G1-K409R Mut-F: SEQ ID NO: 25
G1-K409R Mut-R: SEQ ID NO: 26
G4-R409K Mut-F: SEQ ID NO: 27
G4-R409K Mut-R: SEQ ID NO: 28

Site-directed mutagenesis was performed using the QuickChange II XL Site-Directed Mutagenesis Kit (Stratagene, Amsterdam, The Netherlands) according to the manufacturer's instructions, with changes as indicated below to increase mutagenic efficiency. This method included the introduction of a silent extra AccI site to screen for successful mutagenesis. First, a prePCR mix was used containing 3 µl 10×pfu reaction buffer, 1 µl dNTP mix (10 mM), 275 ng forward or reverse primer, 50 ng template DNA and 0.75 µl Pfu turbo hotstart polymerase. A prePCR was run using a GeneAmp PCR system 9700 (Applied Biosystems): initial denaturation at 94° C. for 5 min; 4 cycles of 94° C. for 30 sec, 50° C. for 1 min and 68° C. for 14 min. 25 µl of forward primer containing prePCR mix was added to 25 µl of reverse primer containing prePCR mix. 0.5 µl Pfu turbo hotstart was added and amplification was performed: denaturing at 94° C. for 1 min; 14 cycles of 94° C. for 1 min, 50° C. for 1 min and 68° C. for 8 min; 12 cycles of 94° C. for 30 sec, 55° C. for 1 min and 68° C. for 8 min.

PCR mixtures were stored at 4° C. until further processing. Next, PCR mixtures were incubated with 1 µl DpnI for 60 min at 37° C. and stored at 4° C. until further processing. 2 µl of the digested PCR products was transformed in One Shot DNH5α T1$^R$ competent *E. coli* cells (Invitrogen, Breda, The Netherlands) according to the manufacturer's instructions (Invitrogen). Next, cells were plated on Luria-Bertani (LB) agar plates containing 50 µg/ml ampicillin. Plates were incubated for 16-18 hours at 37° C. until bacterial colonies became evident.

After screening by colony PCR and AccI digestion to check for successful mutagenesis, plasmid was isolated from the bacteria and the mutation was confirmed by DNA sequencing. To check if no unwanted extra mutations were introduced the whole HC coding region was sequenced and did not contain any additional mutations.

| Sequence Primer | sequence (5'-3') |
| --- | --- |
| CH1-Betv1-F: SEQ ID NO: 29 | TCTCCTCAGCCAGCACCAAG |
| CH1-Feld1-F: SEQ ID NO: 30 | GTTTGTCTGCAGCCAGCACCAAG |
| CH2-F: SEQ ID NO: 31 | CATCTCCAAAGCCAAAGGTGGGACC |
| CH2-R: SEQ ID NO: 32 | GGTCCCACCTTTGGCTTTGGAGATG |
| CH3-F: SEQ ID NO: 33 | CGACGGCTCCTTCTTCCTCTACAG |
| CH3-R: SEQ ID NO: 34 | CTGTAGAGGAAGAAGGAGCCGTCG |

| Mutagenic Primer | Sequence 5'-3' | Mutation | Restriction site |
| --- | --- | --- | --- |
| G1-K409R Mut-F | CCTTCTTCCTCTATAGCAGGCTCACCGTAGACAAGAGCAGGTGGC | Lys > Arg | AccI |
| G1-K409R Mut-R | GCCACCTGCTCTTGTCTACGGTGAGCCTGCTATAGAGGAAGAAGG | Lys > Arg | AccI |
| G4-R409K Mut-F | GGCTCCTTCTTCCTCTACAGCAAGCTAACCGTAGCACAAGAGCAGG | Arg > Lys | AccI |
| G4-R409K Mut-R | CCTGCTCTTGTCTACGGTTAGCTTGCTGTAGAGGAAGAAGGAGCC | Arg > Lys | AccI |

-continued

| Sequence Primer | sequence (5'-3') |
|---|---|
| Intron2-F: SEQ ID NO: 35 | CAAGAGCCATATCCGGGAGGACC |
| Intron2-R: SEQ ID NO: 36 | GGTCCTCCCGGATATGGCTCTTG |
| pEE-F: SEQ ID NO: 37 | GTCAGAGGTAACTCCCGTTG |
| pEE-R: SEQ ID NO: 38 | GTTGTGGTTTGTCCAAACTC |

Recombinant antibodies from these constructs were transiently expressed in HEK 293 cells in 3 ml, 6-wells plates (NUNC) or in 125 or 250 erlenmeyers (Corning) with 293 Fectin (Invitrogen) as transfection reagent.

Example 37. Fab Arm Exchange of IgG1 and IgG4 Hinge Region or CH3 Domain Mutants Antibodies were mixed and subsequently incubated with reduced glutathione (GSH) to investigate the exchange of half molecules. GSH (Sigma-Aldrich, St. Louis, Mo.) was dissolved in water before use.

The exchange of half molecules was evaluated by incubating an antibody mixture consisting of Bet v 1 specific antibody (200 ng) and Fel d 1 specific antibody (200 ng) in PBS/Azide containing GSH (1 or 10 mM) at 37° C. Total incubation volume was 50 µl. After 24 hours samples were drawn from the incubation mixture in PBS-AT (PBS supplemented with 0.3% bovine serum albumin, 0.1% Tween-20 and 0.05% (w/v) NaN$_3$). For samples containing 10 mM GSH an equimolar amount of iodine-acetamide, a strongly alkylating agent that inhibits the GSH activity, was added. Samples were stored at 4° C. for measuring of antigen binding and bispecific activity Levels of Bet v 1 binding antibodies were measured in the antigen binding test. Samples were incubated with 0.75 mg of protein G Sepharose (Amersham Biosciences, Uppsala, Sweden) in 750 µl PBS-IAT (PBS-AT supplemented with 1 µg/ml IVIg) in the presence of $^{125}$I-labeled Bet v 1 for 24h. Next, the Sepharose was washed with PBS-T (PBS supplemented with 0.1% Tween-20 and 0.05% (w/v) NaN$_3$) and the amount of radioactivity bound relative to the amount of radioactivity added was measured. The concentration of Bet v 1 specific IgG was calculated using purified Bet v 1 specific antibodies as a standard (range 0-200 ng per test as determined by nephelometer).

The concentration of bispecific IgG (i.e. Fel d 1-Bet v 1 cross-linking activity) was measured in the heterologous cross-linking assay. In this assay, a sample was incubated for 24 h with 0.5 mg Sepharose-coupled cat extract, in which Fel d 1 antigen is present, in a total volume of 300 µl in PBS-IAT. Subsequently, the Sepharose was washed with PBS-T and incubated for 24 h with $^{125}$I-labeled Bet v 1, after which the Sepharose was washed with PBS-T and the amount of radioactivity bound relative to the amount of radioactivity added was measured. The concentration of bispecific IgG (Fel d 1-Bet v 1) was calculated using the same calibration curve as used in the Bet v 1 binding test, which was obtained from purified Bet v 1 binding IgG. Tests were performed using antibody-containing supernatants in FreeStyle 293 expression medium, GIBCO/Invitrogen Corporation.

The following antibody mixtures were used:
Betv1-IgG1 wt with Feld1-IgG1 wt (indicated as IgG1 wt in FIG. 20)
Betv1-IgG1 P228S with Feld1-IgG1-P228S (IgG1-P228S in FIG. 20)
Betv1-IgG4-CH3(γ1) with Feld1-IgG4-CH3(γ1) (IgG4-CH3(γ1) in FIG. 20)
Betv1-IgG4-R409K with Feld1-IgG4-R409K (IgG4-R409K in FIG. 20)
Betv1-IgG1-CH3(γ4) with Feld1-IgG1-CH3(γ4) (IgG1-CH3(γ4) in FIG. 20)
Betv1-IgG1-K409R with Feld1-IgG1-K409R (IgG1-K409R in FIG. 20)
Betv1-IgG4 wt with Feld1-IgG4 wt (IgG4 wt in FIG. 20)
Betv1-IgG1-P228S-CH3(γ4) with Feld1-IgG1-P228S-CH3(γ4) (IgG1-P228S-CH3(γ4) in FIG. 20)
Betv1-IgG1-P228S-K409R with Feld1-IgG1-P228S-K409R (IgG1-P228S-K409R in FIG. 20)

The results (FIG. 20) showed that at 1 mM GSH, half molecule exchange occurs between IgG4 wt, IgG1-P228S-K409R or IgG1-P228S-CH3(γ4) antibodies. Under these conditions, IgG1 wt, IgG1-P228S, IgG4-CH3(γ1), IgG4-R409K, IgG1-CH3(γ4) or IgG1-K409R antibodies showed no or only minimal exchange of half molecules. At 10 mM GSH, half molecule exchange was also seen in the reactions containing IgG1-CH3(γ4) or IgG1-K409R antibodies.

Example 38. Additional CH3 Mutations to Stabilize Dimerization of Hingeless IgG4 Antibody Molecules in the Absence of IVIG Hingeless IgG4 antibody (HG) molecules form dimers by low affinity non-covalent interactions. WO/2007/059782 describes that this dimerization process can be inhibited by using HG IgG4 molecules in the presence of an excess of irrelevant antibodies. WO/2007/059782 describes a hingeless IgG4 anti-EGFR antibody 2F8-HG.

Construction of pHG-2F8: A vector for the expression of the heavy chain of 2F8-HG: The heavy chain cDNA encoding region of 2F8-HG was codon optimized and cloned in the pEE6.4 vector (Lonza Biologics, Slough, UK). The resulting vector was named pHG-2F8.

Construction of pKappa2F8: A vector for the production of the light chain of 2F8 antibodies: The VL region encoding antibody 2F8 was codon optimized and cloned in the pKappa2F2 vector (a vector encoding the codon optimized cDNA region of antibody 2F2 (described in WO2004035607) in vector pEE12.4 (Lonza)), replacing the 2F2 VL region with the 2F8 VL region. The resulting vector was named pKappa-2F8.

Hingeless IgG4 anti-EGFR antibody 2F8-HG has been described in WO/2007/059782. The additional mutations given in the Table below were introduced into the CH3 region of hingeless IgG4 antibody 2F8-HG by site-directed mutagenesis.

KABAT indicates amino acid numbering according to Kabat (Kabat et al., Sequences of Proteins of Immunological Interest, 5th Ed. Public Health Service, National Institutes of Health, Bethesda, Md. (1991)

EU index indicates amino acid numbering according to EU index as outlined in Kabat et al., Sequences of Proteins of Immunological Interest, 5th Ed. Public Health Service, National Institutes of Health, Bethesda, Md. (1991))

SEQ ID NO:39, 40, 41 indicates amino acid numbering as indicated in SEQ ID NO:39, 40 and 41 of this document.

See also FIG. 22 for comparison of numbering methods.

| Numbering of CH3 mutations | | |
|---|---|---|
| KABAT | EU index G4 | SEQ ID NO: 39, 40, 41 |
| 436 | F405A | F285A |
| 436 | F405L | F285L |
| 440 | R409A | R289A |
| 440 | R409K | R289K |

To make the constructs for the expression of the CH3 mutants, the mutations were introduced into pHG2F8 using site-directed mutagenesis, using the following primers:

| Name | nt | Sequence |
|---|---|---|
| HGF417Af | 48 | CCAGTGCTGGACAGCGACGGAAGCTTCGCCCTGTAC AGCAGGCTGACC (SEQ ID NO: 42) |
| HGF417Ar | 48 | GGTCAGCCTGCTGTACAGGGCGAAGCTTCCGTCGCT GTCCAGCACTGG (SEQ ID NO: 43) |
| HGF417Lf | 51 | CCAGTGCTGGACAGCGACGGATCCTTCTTACTGTAC AGCAGGCTGACCGTG (SEQ ID NO: 44) |
| HGF417Lr | 51 | CACGGTCAGCCTGCTGTACAGTAAGAAGGATCCGTC GCTGTCCAGCACTGG (SEQ ID NO: 45) |
| HGF421Af | 46 | GCTCCTTCTTCCTGTACAGCGCGTTAACCGTGGACA AGTCCAGGTG (SEQ ID NO: 46) |
| HGF421Ar | 46 | CACCTGGACTTGTCCACGGTTAACGCGCTGTACAGG AAGAAGGAGC (SEQ ID NO: 47) |
| HGF421Kf | 45 | CTCCTTCTTCCTGTACAGCAAGCTTACCGTGGACAA GTCCAGGTG (SEQ ID NO: 48) |
| HGF421Kr | 45 | CACCTGGACTTGTCCACGGTAAGCTTGCTGTACAGG AAGAAGGAG (SEQ ID NO: 49) |

The constructs were expressed transiently in HEK-293F cells by cotransfecting the heavy-chain- and light-chain-encoding plasmids and binding to purified EGFr was determined in the absence and presence of 200 μg/ml polyclonal human IgG (Intravenous Immunoglobulin, IVIG, Sanquin Netherlands).

Binding affinities were determined using an ELISA in which purified EGFr (Sigma, St Louis, Mo.) was coated to 96-well MicroIon ELISA plates (Greiner, Germany), 50 ng/well. Plates were blocked with PBS supplemented with 0.05% Tween 20 and 2% chicken serum. Subsequently, samples, serially diluted in a buffer containing 100 μg/ml polyclonal human IgG (Intravenous Immunoglobulin, IVIG, Sanquin Netherlands) were added and incubated for 1 h at room temperature (RT). Plates were subsequently incubated with peroxidase-conjugated rabbit-anti-human kappa light chain (DAKO, Glostrup, Denmark) as detecting antibody and developed with 2,2'-azino-bis (3-ethylbenzthiazoline-6-sulfonic acid) (ABTS; Roche, Mannheim, Germany). Absorbance was measured in a microplate reader (Biotek, Winooski, Vt.) at 405 nm.

FIG. 21 shows that the binding curve of 2F8-HG in the presence of IVIG (thick dotted line with closed boxes) clearly right-shifts with respect to the binding curve of 2F8-HG without IVIG (thick closed line with open boxes). This difference in avidity for the EGFr coat is consistent with the idea that, in the presence of IVIG, 2F8-HG binds monovalently. The binding curves of the tested mutations, 2F8-HG-F405L, 2F8-HG-F405A, 2F8-HG-R409A and 2F8-HG-R409KA, become insensitive to the addition of IVIG and were super-imposable on the bivalent binding curve of 2F8-HG in the absence of IVIG. These differences in avidity for the EGFr coat are consistent with the idea that the 2F8-HG-F405L, 2F8-HG-F405A, 2F8-HG-R409A and 2F8-HG-R409K mutations stabilize dimerization of the HG molecules.

Example 39. Additional CH3 Domain Mutations to Stabilize Dimerization of Human IgG4 Antibodies Mutations as given in the Table below were introduced into the CH3 domains of IgG4-CD20 and IgG4-EGFr by site-directed mutagenesis.

KABAT indicates amino acid numbering according to Kabat (Kabat et al., Sequences of Proteins of Immunological Interest, 5th Ed. Public Health Service, National Institutes of Health, Bethesda, Md. (1991)

EU index indicates amino acid numbering according to EU index as outlined in Kabat et al., Sequences of Proteins of Immunological Interest, 5th Ed. Public Health Service, National Institutes of Health, Bethesda, Md. (1991))

SEQ ID NO:39, 40, 41 indicates amino acid numbering as indicated in SEQ ID NO:39, 40 and 41 of this document. See also FIG. 22 for comparison of numbering methods.

| Numbering of CH3 mutations | | |
|---|---|---|
| KABAT | EU index G4 | SEQ ID NO: 39, 40, 41 |
| 376 | Q355R | Q235R |
| 393 | K370T | K250T |
| 436 | F405A | F285A |
| 436 | F405L | F285L |
| 440 | R409A | R289A |
| 440 | R409K | R289K |
| 440 | R409L | R289L |
| 440 | R409M | R289M |
| 440 | R409T | R289T |
| 450 | E419Q | E299Q |
| 476 | L445P | L325P |

IgG1-CD20 and IgG1-EGFr, IgG4-CD20 and IgG4-EGFr, or IgG4-CH3mutant-CD20 and IgG4-CH3mutant-EGFr were mixed and incubated with 0.5 mM GSH as described above. Bispecific activity was determined as described in Example 33.

FIG. 23 shows that bispecific anti-EGFr/CD20 antibodies were formed in mixtures of IgG4 antibodies as well as in mixtures of CH3 domain mutants Q355R, E419Q, L445P and R409A. No bispecific activity was measured in mixtures of CH3 domain mutants R409K, R409M, R409L and K370T, indicating that these mutations stabilized dimerization of human IgG4 antibodies. CH3 domain mutant R409T, F405A and F405L partially stabilized dimerization of human IgG4 antibodies.

The invention claimed is:

1. A stabilized homodimeric IgG4 antibody, comprising two heavy chains and two light chains, wherein the two heavy chains and the two light chains each comprise a variable region and a constant region,
  wherein the constant region in the two heavy chains is a human IgG4 constant region having a substitution of the Lys residue at EU index position 370 with a Thr residue, and optionally one or more additional amino acid substitutions to reduce Fab arm exchange, selected from: a Lys, Thr, Met, or Leu residue at EU index position 409, and an Ala or Leu residue at EU index position 405, and/or to reduce effector function, selected from: an Ala at EU index position 234, an Ala at EU index position 236, an Ala at EU index position 237, an Ala at EU index position 297, an Ala or Val at EU index position 318, an Ala at EU index position 320, and an Ala or Gln at EU index position 322; and
  wherein the antibody has a Cys-Pro-Ser-Cys sequence (SEQ ID NO: 51) in the hinge region at EU index positions 226-229.

2. The stabilized IgG4 antibody of claim 1, wherein the antibody comprises a Lys, Thr, Met, or Leu residue at EU index position 409.

3. The stabilized IgG4 antibody of claim 1, wherein the antibody comprises an Ala or Leu residue at EU index position 405.

4. The stabilized IgG4 antibody of claim 1, wherein the antibody has reduced effector functions.

5. The stabilized IgG4 antibody of claim 1, wherein the antibody is selected from the group consisting of: a human antibody, a humanized antibody, and a chimeric antibody.

6. The stabilized IgG4 antibody of claim 1, wherein the antibody comprises a human kappa light chain.

7. The stabilized IgG4 antibody of claim 1, wherein the antibody comprises a human lambda light chain.

8. The stabilized IgG4 antibody of claim 1, wherein the antibody is a full-length antibody.

9. The stabilized IgG4 antibody of claim 1, wherein the antibody is linked to a cytotoxic agent; a radioisotope; a prodrug; or a drug.

10. The stabilized IgG4 antibody of claim 1, wherein the antibody binds erythropoietin, beta amyloid, thrombopoietin, interferon-alpha (2a and 2b), interferon-beta (1 b), interferon gamma, TNFR I (CD120a), TNFR II (CD120b), IL-1R type 1 (CD121a), IL-1R type 2 (CD121b), IL-2, IL2R (CD25), IL-2R-beta (CD123), IL-3, IL-4, IL-3R (CD123), IL-4R (CD124), IL-5R (CD125), IL-6R-alpha (CD126), IL-6R-beta (CD130), IL-8, IL-10, IL-11, IL-15, IL-15BP, IL-15R, IL-20, IL-21, TCR variable chain, RANK, RANK-L, CTLA4, CXCR4R, CCR5R, TGF-beta1, TGF-beta2, TGF-beta3, G-CSF, GM-CSF, MIF-R (CD74), M-CSF-R (CD115), GM-CSFR (CD116), soluble FcRI, sFcRII, sFcRIII, FcRn, Factor VII, Factor VIII, Factor IX, VEGF, VEGFxxxb, alpha-4 integrin, Cd11a, CD18, CD20, CD38, CD25, CD74, FcalphaRI, FcepsilonRI, acetyl choline receptor, fas, fasL, TRAIL, hepatitis virus, hepatitis C virus, envelope E2 of hepatitis C virus, tissue factor, a complex of tissue factor and Factor VII, EGFr, CD4, CD28, VLA-1, VLA-2, VLA-3, VLA-4, LFA-1, MAC-1, I-selectin, PSGL-1, ICAM-I, P-selectin, periostin, CD33 (Siglec 3), Siglec 8, TNF, CCL1, CCL2, CCL3, CCL4, CCL5, CCL11, CCL13, CCL17, CCL18, CCL20, CCL22, CCL26, CCL27, CX3CL1, LIGHT, EGF, TGFalpha, HGF, PDGF, NGF, complement, C1q, C4, C2, C3, C5, C6, C7, C8, C9, MBL, factor B, a Matrix Metallo Protease, any of MMP1 to MMP28, CD32b, CD200, CD200R, Killer Immunoglobulin-Like Receptors (KIRs), NKG2D, leukocyte-associated immunoglobulin-like receptors (LAIRs), ly49, PD-L2, CD26, BST-2, ML-IAP (melanoma inhibitor of apoptosis protein), cathepsin D, CD40, CD4OR, CD86, a B cell receptor, CD79, PD-1, or a T cell receptor.

11. A pharmaceutical composition comprising the stabilized IgG4 antibody of claim 1.

* * * * *

UNITED STATES PATENT AND TRADEMARK OFFICE
CERTIFICATE OF CORRECTION

PATENT NO. : 10,752,695 B2
APPLICATION NO. : 15/197496
DATED : August 25, 2020
INVENTOR(S) : Jan Van De Winkel et al.

Page 1 of 1

It is certified that error appears in the above-identified patent and that said Letters Patent is hereby corrected as shown below:

In the Claims

Claim 10, Column 72, Line 56, "CD4OR" should read --CD40R--.

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*